United States Patent
Warnke et al.

(10) Patent No.: US 9,095,524 B2
(45) Date of Patent: Aug. 4, 2015

(54) CUSTOMIZED COMPOSITIONS AND USES THEREOF

(71) Applicant: Bond University Ltd., Gold Coast, QLD (AU)

(72) Inventors: Patrick Warnke, Robina (AU); Qin Liu, Queensland (AU)

(73) Assignee: Bond University LTD, Gold Coast, QLD (AU)

( * ) Notice: Subject to any disclaimer, the term of this patent is extended or adjusted under 35 U.S.C. 154(b) by 42 days.

(21) Appl. No.: 13/649,620

(22) Filed: Oct. 11, 2012

(65) Prior Publication Data

US 2013/0095167 A1    Apr. 18, 2013

(30) Foreign Application Priority Data

Oct. 11, 2011  (AU) ................. 2011904165

(51) Int. Cl.
| | |
|---|---|
| *A61K 9/70* | (2006.01) |
| *A61L 27/14* | (2006.01) |
| *A61L 27/38* | (2006.01) |
| *A61L 27/56* | (2006.01) |
| *A61L 27/60* | (2006.01) |
| *B82Y 5/00* | (2011.01) |

(52) U.S. Cl.
CPC ............... *A61K 9/7007* (2013.01); *A61L 27/14* (2013.01); *A61L 27/3834* (2013.01); *A61L 27/56* (2013.01); *A61L 27/60* (2013.01); *A61L 2400/12* (2013.01); *A61L 2430/16* (2013.01); *B82Y 5/00* (2013.01); *Y10S 977/788* (2013.01)

(58) Field of Classification Search
CPC .. A61K 9/7007; A61L 2400/12; A61L 27/14; A61L 27/3834; B82Y 5/00; Y10S 977/788
USPC .......... 424/93.7, 443, 484; 435/325, 375, 377
See application file for complete search history.

(56) References Cited

U.S. PATENT DOCUMENTS

| | | | |
|---|---|---|---|
| 6,245,345 B1 * | 6/2001 | Swanbom et al. | ............. 424/402 |
| 8,642,072 B2 * | 2/2014 | Coffey et al. | ................. 424/443 |
| 2011/0004304 A1 * | 1/2011 | Tao et al. | ..................... 623/6.63 |

FOREIGN PATENT DOCUMENTS

WO    WO2006109137 A1 *  10/2006

OTHER PUBLICATIONS

Stanzel et al. Invest. Ophthalmol. Vis. Sci. 2007, vol. 48, E-Abstract 5085.*

* cited by examiner

*Primary Examiner* — Janet Epps-Smith
(74) *Attorney, Agent, or Firm* — McHale & Slavin, P.A.

(57) ABSTRACT

The present invention relates to a customized composition comprising three-dimensional (3D) nanofiber webbing. The present invention further relates to the process of producing the composition comprising 3D nanofiber webbing and uses thereof such as treatment of age-related macular degeneration or regeneration/repair of tissue.

11 Claims, 37 Drawing Sheets

(A)

(B)

a)

b)

CUSTOMIZED COMPOSITIONS AND USES THEREOF

CROSS-REFERENCE TO RELATED APPLICATIONS

The present application claims priority of Australian provisional patent application No. 2011904165 filed Oct. 11, 2011 and is incorporated herein by reference in its entirety.

FIELD OF THE INVENTION

The present invention relates to a customized composition comprising three-dimensional (3D) nanofiber webbing. The present invention further relates to the process of producing the composition comprising 3D nanofiber webbing and uses thereof such as treatment of age-related macular degeneration or regeneration/repair of tissue.

BACKGROUND

The skin, which is the body's largest organ, is essential to an organism's survival as it forms a physical barrier that helps prevent harmful microorganisms and chemicals from entering the body. As well as resisting harmful elements from entering it, the skin has a role in secreting certain waste products from the body. In addition, the skin is a protective structure for internal organs as it softens potential blows to the body. Also, the skin prevents the loss of body fluids and shields the internal organs from damaging ultraviolet light from the sun.

The skin is between 1.4 to 4.0 mm thick. Generally, the skin is relatively thin in places that are most visible (e.g. thighs, forearms, face etc.) with the thickest areas being areas of the body that are subjected to rubbing or friction such as the palms of the hands and the soles of the feet.

Regardless of the thickness, the skin consists of two distinct layers, the epidermis and the dermis. The epidermis is the outer layer of the skin and is a tough, waterproof, protective layer. The dermis, or inner layer, is thicker than the epidermis and gives the skin its strength and elasticity. The two layers of the skin are anchored to one another by a thin but complex layer of tissue known as the basement membrane which is composed of a series of elaborately interconnecting molecules that serve to hold the skin together. Below the dermis is the subcutaneous layer, the hypodermis, which is a layer of tissue composed of protein fibers and adipose tissue. Although not technically part of the skin, the subcutaneous layer contains glands and other skin structures, as well as sensory receptors involved in the sense of touch.

Although very resilient, skin can be damaged in many ways, and sometimes permanently. The skin begins repair immediately upon injury.

Wound healing, or wound repair, is an intricate process in which the skin (or another organ-tissue) repairs itself after injury. In normal skin, the epidermis (outermost layer) and dermis (inner or deeper layer) exists in steady-state equilibrium, forming a protective barrier against the external environment. Once the protective barrier is broken, the normal (physiologic) process of wound healing is immediately set in motion. The classic model of wound healing is divided into three or four sequential, yet overlapping, phases: (1) hemostasis (not considered a phase by some authors), (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis).

In the inflammatory phase, bacteria and debris are phagocytosed and removed, and factors are released that cause the migration and division of cells involved in the proliferative phase.

The proliferative phase is characterized by angiogenesis, collagen deposition, granulation tissue formation, epithelialization, and wound contraction. In angiogenesis, new blood vessels are formed by vascular endothelial cells. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

In the maturation and remodeling phase, collagen is remodeled and realigned along tension lines and cells that are no longer needed are removed by apoptosis.

The wound healing or wound repair process occurs frequently with skin since there is a high incidence of injury to the skin. Severe injury due to invasive skin surgery (e.g. ablation of cancerous skin tissue) or accidental collision with an object or burns can involve all layers of the skin (full thickness wounds) in which wound repair may be lengthy and is likely to result in overt scarring. Skin deformities or permanent abnormalities are possible manifestations of deep wound healing and repair. The process of wound healing is fragile and susceptible to interruption or failure leading to the formation of chronic non-healing wounds. Factors which may contribute to this include diabetes, venous or arterial disease, old age, and infection.

A chronic wound is a wound that does not heal in an orderly set of stages and in a predictable amount of time the way most wounds do; wounds that do not heal within three months are often considered chronic. Chronic wounds seem to be detained in one or more of the phases of wound healing. For example, chronic wounds often remain in the inflammatory stage for too long. In acute wounds, there is a precise balance between production and degradation of molecules such as collagen; in chronic wounds this balance is lost and degradation plays too large a role.

Chronic wounds may never heal or may take years to do so. These wounds cause patients severe emotional and physical stress as well as creating a significant financial burden on patients and whole healthcare systems. The integrity and appearance of the skin associated with a chronic wound is unsatisfactory with the strength of skin around 50% or less. There is no effective treatment for chronic wound.

When it comes to skin appearance, there is deep emotional stress associated with physical abnormalities of the skin. These abnormalities could be congenital or environmentally triggered (e.g. from severe burns) and visually present as deep pockets or crevices in the face, for example. The approach to repairing and reshaping tissue is limited to skin grafts and poorly performing skin substitutes. However, most of these treatments are suboptimal as they are linked to various deficiencies, such as:

Limited availability of donor tissue;
Grafted dermis does not regenerate, resulting in scars that contract;

Larger donor sites are needed to compensate for graft shrinkage;

Harvested donor sites are painful, itchy and red;

The requirement for the donor skin or the skin substitute to be replaced numerous times during the healing process;

Scaled, rough, dry appearance in skin at the wound site;

Likelihood of tissue rejection;

Stiffness of graft area; and

Overall disappointing functional and cosmetic outcomes.

SUMMARY OF THE INVENTION

According to a first aspect of the invention, there is provided a composition to regenerate or repair tissue, wherein the composition comprises three-dimensional (3D) nanofiber webbing and at least one agent, wherein the webbing comprises at least a first layer and a second layer wherein the first and second layers are distinct from each other, and wherein the thickness of the composition corresponds to the thickness of the tissue when healthy, wherein the first and second layers of the webbing correspond to a first layer and a second layer of the tissue.

In one embodiment, the first layer and the second layer of the composition may correspond to the first layer and the second layer of the tissue by mimicking extracellular matrix or a layer of cells. In a further embodiment, a layer of the composition which corresponds to a layer of cells in the tissue is seeded with one or more cells. The seeded cells may be the same cell type as the cells in the tissue layer. Alternatively, the seeded cells may differ to the cell type of the cells in the tissue layer but allowed to differentiate into the same cell type through cultivation. The seeded cells may be stem cells. The stem cells may be human. Cultivation may occur prior to contacting the tissue that requires repair or regeneration with the composition.

In another embodiment, the composition comprises three, four or more layers. The composition is amendable and is contoured to the shape of the tissue.

In a further embodiment, the layers are interwoven.

In yet a further embodiment, the layers are in the form of sheets. The sheets may be interconnected by interweaving the sheets. The sheets may be rolled to form an open tube. In yet a further embodiment, the composition contains three or more layers, wherein three layers each comprise one of the following cell types: photoreceptor cells (rods, cones), various types of nerve cells or cells of neural origin and retinal pigmented epithelial cells. A fourth layer could contain cells similar to retinal pigmented epithelial cells. Additional layers with neural cells to connect to the optic nerve or cells to support and connect to cells of the other layers may be added.

In yet another embodiment, each layer may be applied by dispersing a liquid comprising a polymer or a mix of polymers through an electric field and onto another layer or onto the surface of a collector. The collector may be in the form of a cast or model.

In another embodiment, each of the first, second, third, fourth or more layers of the webbing may consists of one polymer or a mix of two or more polymers. One or more layers may be formed by a polymer or a mix of two or more polymers that differ to the polymer or mix of two or more polymers that form another one or more layers. Two or more layers may have the same polymer or mix of two or more polymers but placed in a different orientation. The polymer may be natural or synthetic and may be biodegradable.

In a further embodiment, the agent may be a physiochemical agent or a therapeutic agent. The agent may be encapsulated or coated for delayed release. The agent may be released from the composition upon insertion into the tissue that requires repair or regeneration. The agent may be ANTI-VEGF.

The composition may further comprise a material which may be synthetic or naturally derived and be in the form of a gel, gas, cream, salve or a solid.

In one embodiment, the tissue that requires regeneration or repair may belong to the body part or organ that is selected from the group comprising face, breast, ears, neck, axilla, groin, hands, elbows, arms, legs, feet, knees, genitals, eye lids, nose, lips, skin, eyes, including the cornea, retina (including Bruch's membrane (BM)), optic nerve and any other anatomical back wall of the eye not specifically mentioned here, liver, bile ducts and bile bladder, kidney, bowel, heart, pancreas, spleen, GALT, MALT, throat, esophagus, larynx, lungs, veins, arteries, stomach, small intestine, duodenum, ileum, jejunum, colon, large intestine, brain, spinal cord and nerves, muscles (smooth, skeletal and mixed muscles), vessels, uterus, bladder and urethra and ureters, ovaries, vagina, rectum, thyroid, tongue, oral, gastrointestinal and nasopharyngeal mucosa, periodontal and dental tissues, smooth and skeletal muscle, hair, nipples, apokrin, ekrin and endokrin glands, hair follicles, bone cartilage, tendons, periosteum, and perichondrium.

The composition may be large in scale and in the form of artificial skin. The composition may be small in scale and ultrathin for the retina, BM or any anatomical part of the back wall of the eye.

According to a second aspect of the invention, there is provided a method of regenerating or repairing tissue in a subject; the method comprising administration of a composition to the site of the body of the subject that contains the tissue, wherein the composition comprises a three-dimensional (3D) nanofiber webbing and at least one agent, wherein the webbing comprises at least a first layer and a second layer wherein the first and second layers are distinct from each other, and wherein the thickness of the composition corresponds to the thickness of the tissue when healthy, wherein the first and second layers of the webbing correspond to a first layer and a second layer of the tissue.

In one embodiment, the agent is one or more cells. The first layer and the second layer of the composition may correspond to the first layer and the second layer of the tissue by mimicking a layer of cells. The one or more cells may be the same cell type as cells in the tissue layer. Alternatively, the one or more cells may differ to the cell type of the cells in the tissue layer but allowed to differentiate into the same cell type through cultivation. The one or more cells may be stem cells. The stem cells may be human.

According to a third aspect of the invention, there is provided a method of treating macular degeneration in a subject, comprising administration of a composition to macula tissue in the retina of the subject, wherein the composition comprises a three-dimensional (3D) nanofiber webbing and at least one agent, wherein the webbing comprises at least a first layer and a second layer wherein the first and second layers are distinct from each other, and wherein the thickness or architecture of the composition corresponds to the thickness or architecture of the tissue when healthy, wherein the first and second layers of the webbing correspond to a first layer and a second layer of the tissue.

In one embodiment, the agent is one or more stem cells. The one or more stem cells are allowed to colonize the composition by culturing the cells in vitro. The composition that may be used in this method is an ultrathin membrane that comprises at least one polymer. The polymer may be any collagen type or a combination of various collagen types (e.g.

collagen I and IV) or any other polymer such as PLGA, PCL, Elastin and others. The membrane comprising stem cells is patched against or surgically integrated into the back wall of the eye. The membrane degrades over time which releases the cells and agents into the impaired macula. The stems cells differentiate into photoreceptor cells or other cells of the retina and underlying tissue resulting in regeneration of the macula.

According to a fourth aspect, the invention provides use of a composition to repair or regenerate tissue in a subject, use comprising administration of the composition to the site of the body of the subject that contains the tissue, wherein the composition comprises a three-dimensional (3D) nanofiber webbing and at least one agent, wherein the webbing comprises at least a first layer and a second layer wherein the first and second layers are distinct from each other, and wherein the thickness of the composition corresponds to the thickness of the tissue when healthy, wherein the first and second layers of the webbing correspond to a first layer and a second layer of the tissue.

In a further embodiment, the method of the third aspect and use of the fourth aspect optionally comprise the steps of the process of the fifth aspect and embodiments thereof.

Accordingly to a fifth aspect, the invention provides a process of producing a composition for regenerating or repairing tissue, wherein the composition comprises three-dimensional (3D) nanofiber webbing and at least one agent, wherein the webbing comprises at least a first layer and a second layer wherein the first and second layers are distinct from each other, and wherein the thickness of the composition corresponds to the thickness of the tissue when healthy, wherein the first and second layers of the webbing correspond to a first layer and a second layer of the tissue, wherein the process comprises the following steps: (a) Measuring thickness and/or architecture of the tissue that requires regeneration or repair, (b) Measuring thickness and/or architecture of the first and second layers of the tissue; (c) Determining the desired thickness and/or architecture of the composition based on the measurement steps of (a) and (b); (d) Placing a collector in an electric field of a nanofiber webbing machine; (e) Dispersing one or more polymers through an electric field to contact the collector for a time and under conditions sufficient to produce the first layer of the composition; (f) Adding one or more agents to the first layer after dispersion of the one or more polymers of (e); (g) Dispersing one or more polymers through an electric field to contact the collector for a time and under conditions sufficient to produce the second layer of the composition; (h) Optionally, repeating dispersion of one or more polymers to produce additional layers; (i) Removing the layers from the collector; and (j) Contouring the layers of the composition into the shape of tissue.

In one embodiment, the one or more agents are added to the second layer, in addition or alternatively to, the one or more agents previously added to the first layer. The one or more agents may be tissue specific or stem cells or progenitor cells.

In a further embodiment, the composition produced by the process comprises at least three layers. One layer is seeded with photoreceptor cells. Another layer is seeded with retinal pigmented epithelial cells. A third layer is seeded with one or more nerve cells or cells of neural origin. Alternatively, the composition is seeded with one or more stem cells that differentiate into photoreceptor cells, retinal pigmented epithelial cells and one or more nerve cells. A fourth layer could contain cells similar to retinal pigmented epithelial cells. Additional layers with neural cells to connect to the optic nerve or cells to support and connect to cells of the other layers may be added.

In another embodiment, dispersion occurs by spraying or spinning the one or more polymers.

In yet another embodiment, the collector is a cast prepared from an impression mould of a body part that requires tissue regeneration or repair. Alternative to preparing a cast from a mould, the following steps may be taken: (a) Measuring the contour of the body part that requires tissue regeneration or repair by 3D imaging techniques; (b) Inputting the measurements into a design based application to prepare a physical model of the body; and (c) Using the model as the collector.

In the above embodiment, the 3D imaging technique may be selected from the group comprising Scan x-ray, CT scan, cone beam x-ray, MRI and 3D photography. In a further embodiment, the design based application is selected from the group comprising computer aided design (CAD) and rapid-prototyping. In a further embodiment, rapid-prototyping may include 3D printing, 3D selective lasering, 3D selective sintering, 3D casting, 3D burring, 3D grinding or any combination thereof.

The electric field is generated when voltage is applied to the spinning electrode. The mould or model can either be placed between the electrode or it can be connected to earth, consequently be used as the collecting electrode.

The process may further comprise the step of hardening of the 3D nanofiber webbing. The step of hardening may comprise chemical or physical hardening. Hardening could occur by polymerization such as by light curing of a polymer.

According to a sixth aspect, there is provided a composition obtainable by the process of the fifth aspect.

According to a seventh aspect, there is provided a composition obtained by the process of the fifth aspect.

According to an eighth aspect, the invention provides the composition of the sixth or seventh aspect, when used to treat macular degeneration or correct deformities or abnormalities of the skin.

General embodiments of the above-listed aspects are provided below.

One or more agents is selected from the group comprising one or more antibiotics, antimicrobial peptides, antimicrobial defensins, cytokines, growth factors, hormones, cell influencing and interactive materials, signaling cues such as small molecules, surface adhesive molecules and proteins, that influence cell behavior, human cells, natural tissue fibers or any combination thereof.

The composition comprises additional material which may be in the form of a gel, gas, cream, salve or a solid. The additional material may be inorganic. An inorganic material may be selected from the group comprising carbon nanotubes (CNTs), a metal or alloy, hydroxyapatite and silver particles.

In another embodiment, the composition could contain at least one curable polymer or at least one curable resin or at least one self-hardening clay or their combination to provide structural stability to the composition.

In yet another embodiment, one or more polymers can be integrated into the layers of the composition by a electrospinning technique that is selected from the group comprising direct dispersion electrospinning, co-evaporation and emulsion electrospinning In a further embodiment, the thickness of the composition varies as it depends on the deformity or abnormality of the body part that requires treatment. Generally, the thickness of the composition is between about 5 um and about 4 mm. In another embodiment, the thickness may be at least 100 nm without an upper limit.

Other aspects are described infra.

BRIEF DESCRIPTION OF THE FIGURES

A preferred embodiment of the present invention will now be described, by way of examples only, with reference to the accompanying figures wherein:

FIG. 3.

FIG. 4.

DEFINITIONS

Figure 1:
FIG. 1. Pictorial representation of the steps for preparing a face mould. The steps include use of paper mache to create the mould.

Throughout this specification, unless the context requires otherwise, the word "comprise", or variations such as "comprises" or "compromising", will be understood to imply the inclusion of a stated step or element or integer or group of steps or elements or integers but not the exclusion of any one step or element or integer or group of elements or integers. As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

As used herein "layer" is distinct from another layer chemically, morphologically and/or mechanistically. Two or more layers comprise a composite. As used herein, the term "composite" as known to a person skilled in the art is the presence of two or more constituent materials with significantly different physical and/or chemical properties which remain distinct at the macroscopic or microscopic scale within the finished structure. In this case, the two or more constituent materials could be the two or more layers. Three or more layers comprise a composite that is in the form of a sandwich. Each layer has a thickness and is substantially less that its length and width. Layers can be amendable and form to any shape or contour. Layers may be hardened to maintain any shape or contour. Layers can be in the form of a sheet or sheets (e.g. square sheets, rounded sheets such as in a "tortilla" like structure, rectangular sheets and irregular shaped sheets). These sheets can be interconnected through interweaving them. The sheets may be rolled into an open tube which resembles a "burrito". Also, there is contemplation of closed tubes, sections of tubes (e.g. bands) spheres or any shape or form that enables the proper placement of the composition to the body part which contains the tissue that requires regeneration or repair. Layers can have any orientation relevant to another layer. For example, one layer may be parallel or perpendicular to another layer. Also, one layer could traverse one or more other layers or folded onto itself or around another layer. One or more layers can be repeated either sequentially or repeat after one or more differing layers are added. For example, if the first layer is A followed by layer B or C, there could be another layer with A again.

The term "composition" is known in the art and its broadest meaning is contemplated herein.

The term "matrice" or "matrix" of the composition is used interchangeably with the terms "webbing" and "membrane".

As used herein, the term "biodegradable" means that one or more polymers of one or more layers underwent bond cleavage in vivo. Cleavage could be via any chemical reaction that achieves the breaking of chemical bonds, e.g. hydrolysis, oxidation, enzymatic breakdown, etc.). Loss in mass of the polymer in vivo over time may be in the range of 40% to 80% to 93% to 98% to 99% or more of the original polymer mass prior to placing composition in vivo and time for complete biodegradation may be between minutes and years.

The term "distinct" or "distinction" herein means that each layer may differ from one another either chemically, mechanically and/or morphologically.

The term "chemical" is very broad and includes the chemical content, and thus potential chemical interaction, in a layer. The chemical content in a layer includes, but is not limited to, protons, neutrons, electrons, elements, different charges, ions, compounds, molecules, agents, proteins, peptides, cells. The interaction may occur via SN1, SN2 reactions. "Chemical distinction" means one layer differs to another layer in chemical content or interaction. "Chemical distinction" between layers is achieved by using different polymers and/or different agents. Two or more layers may comprise the same polymer but comprise a different agent or agents. Alternatively, two or more layers may comprise different polymers but comprise the same agent or agents. In one example, one layer may contain a polymer while another layer contains a polymer but seeded with a titre of cells for subsequent proliferation. These two layers are considered chemically distinct.

The term "morphology" means the shape, size, and/or texture of a layer. "Morphological distinction" means one layer differs to another layer in shape, size, and/or texture. "Morphological distinction" is achieved by varying voltage of the field and/or distance of electrodes that create the field and/or using different polymers and/or changing orientation of the same polymer or same mix of polymers.

The term "mechanical" means behavior of a polymer, agent, or material of a layer when subjected to forces or displacements. Mechanical aspects may include rigidity of a polymer to provide structural support. "Mechanical distinction" between layers may be achieved by using different polymers and/or different agents and/or varying voltage of the electric field and/or distance of electrodes that create the field.

The term "agent" can mean any substance that has an affect on the human body. This term includes "physiochemical agent" and "therapeutic agent". The term "physiochemical agent" means an agent that as an affect on any function of a living body including interaction of biomolecules that carry out the chemical or physical functions that exist in the body.

"Therapeutic agent," or "therapeutic agents," could mean and include "pharmaceutically active agents," "pharmaceutically active materials," "drugs," and "biologically active agents". Other related terms may be used interchangeably herein and include genetic therapeutic agents, non-genetic therapeutic agents and cells. Any agent or material in the composition may be encapsulated for delayed release.

A "material" is any synthetic or naturally derived substance that is added to any layer of the composition. The material may be used to (a) make the structure of the composition more rigid or more flexible; (b) capture molecules or cells into the 3D nanofibre webbing; (c) preserve one or more agents present in the 3D nanofibre webbing from degradation or postpone degradation, and/or (d) activate or inhibit one or more agents. The material may be in the form of a gel, gas, cream, salve or a solid. The material may be organic or inorganic. As contemplated herein, the material may include but not limited to, minerals, ceramics, nanodiamonds, crystals, amorphous minerals as well as hydroxyapatite, fluorapatite, tricalciumphosphate, calciumphosphate for bone and hard (calcified) tissue. Also metals and alloys such as gold, silver, copper, zinc, tin, platinum, titanium, magnesium alloys are contemplated herein and alkaline metals such as Na, Ca, F, Li, K, Mg, plus Cl, Br, and Iodine.

A "tissue" as described herein is an ensemble of cells, not necessarily identical, but from the same origin, that together carry out a specific function. These are called tissues because of their identical functioning. Organs are then formed by the functional grouping together of multiple tissues.

The term "drug" as used herein is defined as a compound which aids in the treatment of disease or medical condition or which controls or improves any physiological or pathological condition associated with the disease or medical condition.

The term "anticancer drug" as used herein is defined as a drug for the treatment of cancer, such as for a solid tumor. The anticancer drug preferably reduces the size of the tumor, inhibits or prevents growth or metastases of the tumor, and/or eliminates the tumor. The terms "anticancer drug," "anticancer drug," and "anti-cancer compound" are used interchangeably herein.

A person of ordinary skill in the art will recognize that morphological and/or chemical modifications can be made to the composition of the present invention, without departing from the spirit and scope of the present invention.

Throughout this application, the term "about" or "correspond" is used to indicate that two values or aspects that can be measured, such as thickness, are not necessarily identical and that a difference between values includes the inherent variation of error in the method being employed to determine the value (e.g. for measuring thickness), variation in the production process of the composition even though the aim is to have the thickness of the composition be the same as the tissue that requires regeneration or repair.

The use of the term "or" in the claims is used to mean "and/or" unless explicitly indicated to refer to alternatives only or the alternatives are mutually exclusive.

It is contemplated that any embodiment discussed in this specification can be implemented with respect to any method or composition of the invention, and vice versa. Furthermore, compositions of the invention can be used to achieve the methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The present invention is predicated on the discovery of a customized tissue regeneration composition comprising 3D nanofiber webbing that overcomes many, if not all, of the deficiencies of the current skin graft and skin substitute treatments currently available. The composition is made from a unique process of customizing the tissue composition to better treat the individual subject that presents with their particular skin deformity or abnormality.

The present invention is not only useful for cosmetic and medical applications on the surface of the body, but useful in regenerating tissue internally. There are many circumstances where internal organs and structures within the body require tissue regeneration. Apoptosis, or programmed cell death is a process that the body relies upon to kill unwanted cells such as cells that have reached the end of their life (e.g. red blood cells). However, if triggered unnecessarily, apoptosis can have deleterious effects. Nitric oxide is a compound that can over-stimulate apoptosis. Apoptosis that is overly stimulated at one time or stimulated over a long period of time has the ability to cause harm to the body and linked to various conditions. Apoptosis has been found to be the primary contributor to age-related macular degeneration (AMD). AMD is a medical condition which usually affects older adults and results in a loss of vision in the center of the visual field because of damage of anatomical parts in the back of the eye, for example in the retina or Bruch's membrane (BM). It occurs in "dry" and "wet" forms. It is a major cause of blindness and visual impairment in older adults (>50 years). Macular degeneration can make it difficult or impossible to read or recognize faces.

The macula is the central area of the retina, which provides the most detailed central vision. The retina is one of three main layers at the back of the eye. Starting from the inside of the eye and going towards the back, the three main layers are the retina; the choroid, which contains the blood supply; and the sclera, which is the white of the eye. The "dry" form of advanced AMD, results from atrophy of the retinal pigment epithelial layer below the retina, which causes vision loss through loss of photoreceptors (rods and cones) in the central part of the eye. No medical or surgical treatment is available for this condition.

Atrophy is the general physiological process of reabsorption and breakdown of tissues, involving apoptosis on a cellular level. When it occurs as a result of disease or loss of trophic support due to other disease, it is termed pathological atrophy, although it can be a part of normal body development and homeostasis as well. Accordingly, atrophy could be associated with loss of any tissue within the body.

In "wet" AMD, neovascularization occurs below the basement matrix layer (foundation) of the retina, which is called Bruch's membrane. Bruch's membrane is the innermost layer of the choroid. There is treatment currently available against wet AMD which is the administration of ANTI-VEGF.

The present invention is predicated on the discovery of a composition comprising 3D nanofiber webbing which has the ability to be customized through a novel nanofiber electrospinning process such that the composition could be used, for example, to regenerate tissue through the delivery and growth of certain cells or to repair tissue through the delivery of various agents.

Figure 7:
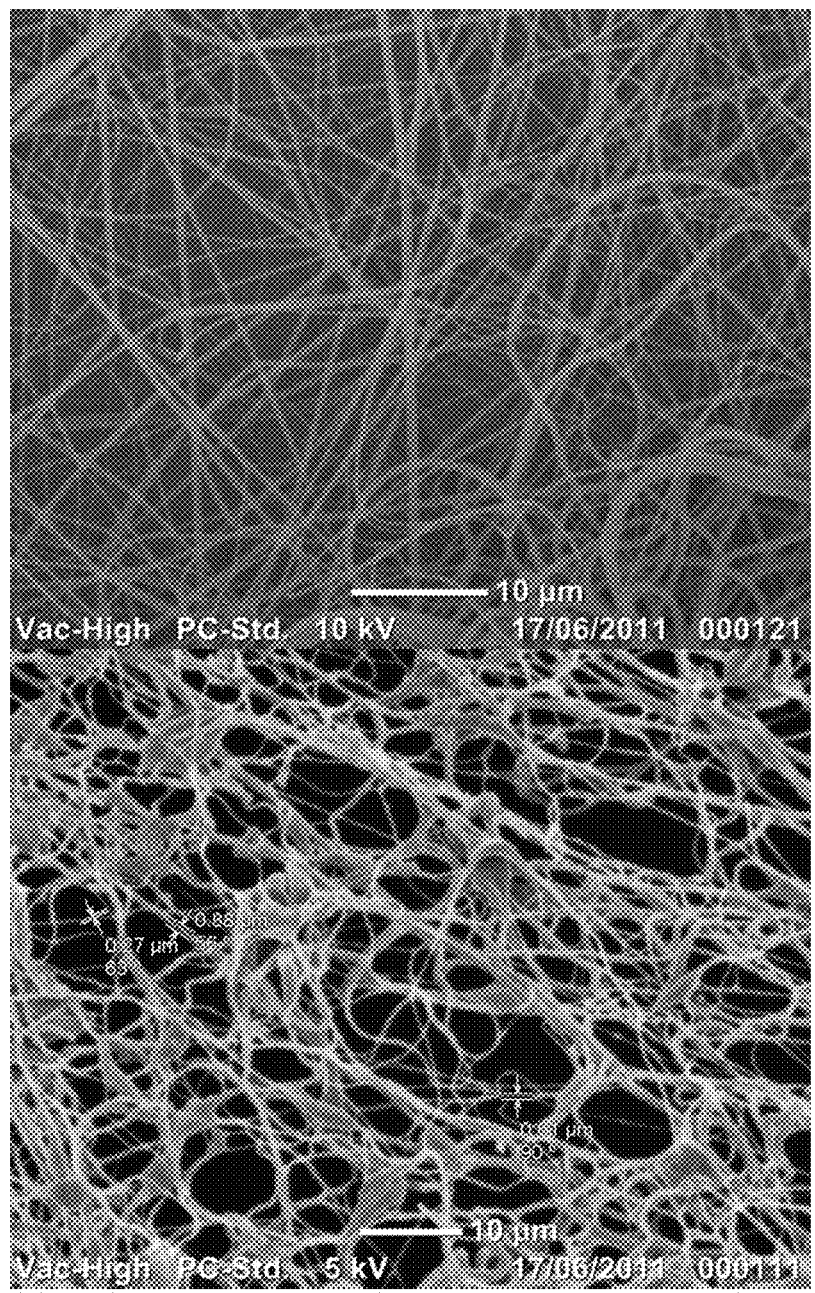
FIG. 7. Micrograph of a gelatine membrane (Top) and biodegradable polymer membrane (Bottom).
Figure 8:
FIG. 8. Pictures of full face replacement and which demonstrates peel of process. Nose and upper lip only (cut out from full face, but keeping its shape as a replacement part) is shown.
Figure 8:
Figure 8:
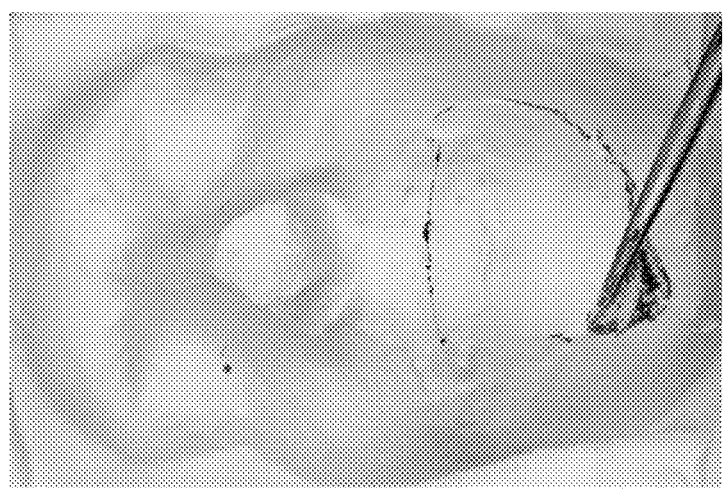
Figure 9:
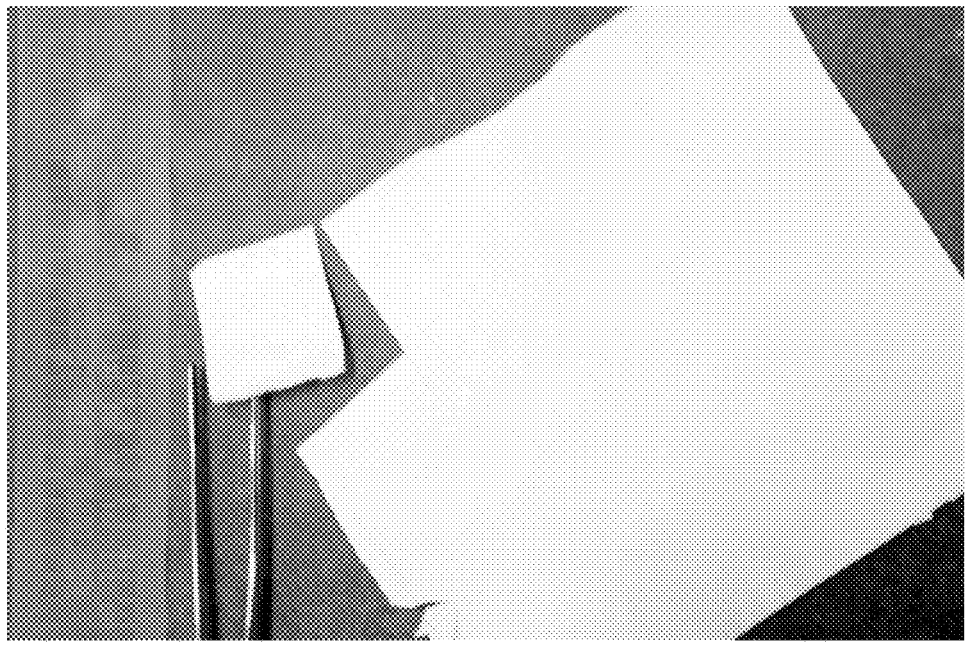
FIG. 9. Pictures of a flat membrane and its application to the jaw to cover bone.
Figure 9:
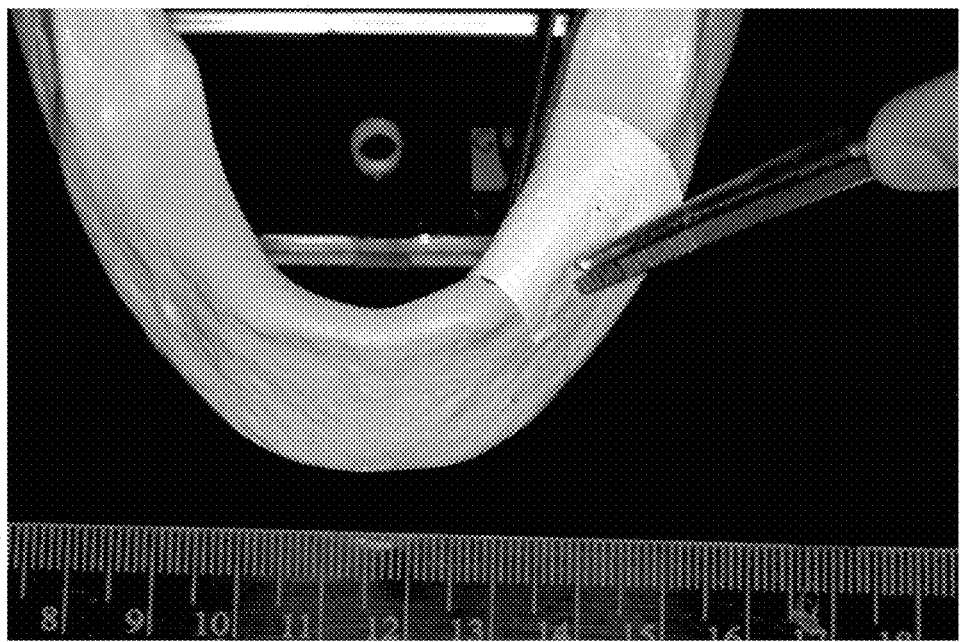

The inventor has discovered a customized tissue regeneration composition comprising three-dimensional (3D) nanofiber webbing (see FIG. 7) which can be applied to any body part that requires tissue regeneration or repair, including but not limited to, the face, breast, ears, neck, axilla, groin, hands, elbows, arms, legs, feet, knees, genitals, eye lids, nose, lips, skin, eyes, including the cornea, retina, BM, optic nerve or any other anatomical part in the back wall of the eye, liver, bile ducts and bile bladder, kidney, bowel, heart, pancreas, spleen, GALT, MALT, throat, esophagus, larynx, lungs, veins, arteries, stomach, small intestine, duodenum, ileum, jejunum, colon, large intestine, brain, spinal cord and nerves, muscles (smooth, skeletal and mixed muscles), vessels, uterus, bladder and urethra and ureters, ovaries, vagina, rectum, thyroid, tongue, oral, gastrointestinal and nasopharyngeal mucosa, periodontal and dental tissues, smooth and skeletal muscle, hair, nipples, apokrin, ekrin and endokrin glands, hair follicles, bone cartilage, tendons, periosteum, and perichondrium.

Embodiments of the invention includes within its scope use and methods of the composition for repairing or regenerating tissue. Any tissue that has been impaired as a result of a disease, condition, or genetic defect is contemplated herein and considered to be a tissue that would benefit from the application of the composition of the invention. For example, the composition may be used to treat macula degeneration by applying the composition, which would be in the form of a patch or membrane and comprising stem cells, to the macula. In one example, macula degeneration may be age-related macula degeneration.

The discovery includes within the scope of the invention a process of obtaining a customized tissue regeneration composition comprising three-dimensional (3D) nanofiber webbing. The unique process includes the steps of (a) Preparing an impression mould of at least the body part that requires tissue regeneration or repair; (b) Preparing a cast from the mould; (c) Placing the cast in an electric field of a nanofiber webbing machine; (d) Applying a 3D nanofiber webbing to the cast to a desired thickness; (e) Removing the 3D nanofiber webbing from the cast; and (f) Fitting the webbing to the body part that requires tissue regeneration or repair.

Figure 3A:
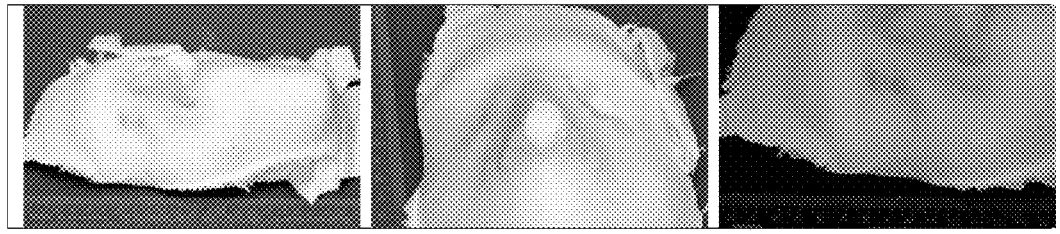
(FIG. 3A) Pictorial representation of the resulting composition of the nanofiber process in which the composition has been removed from the face cast.
Figure 3A:
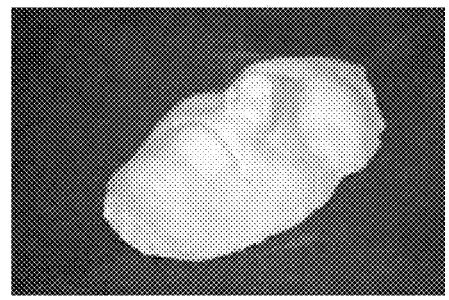
Figure 3B:
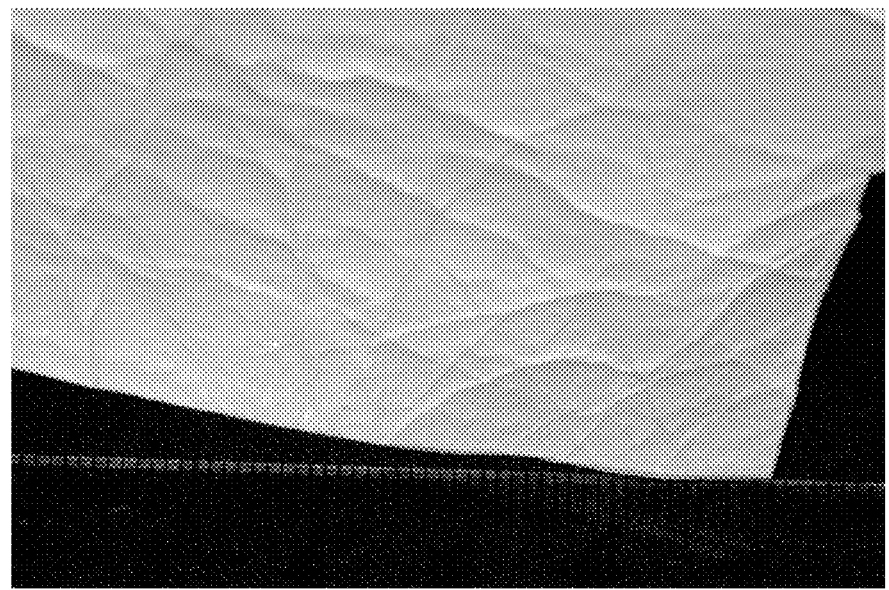
(FIG. 3B) Pictorial representation of artificial skin in a large scale.
Figure 3C:
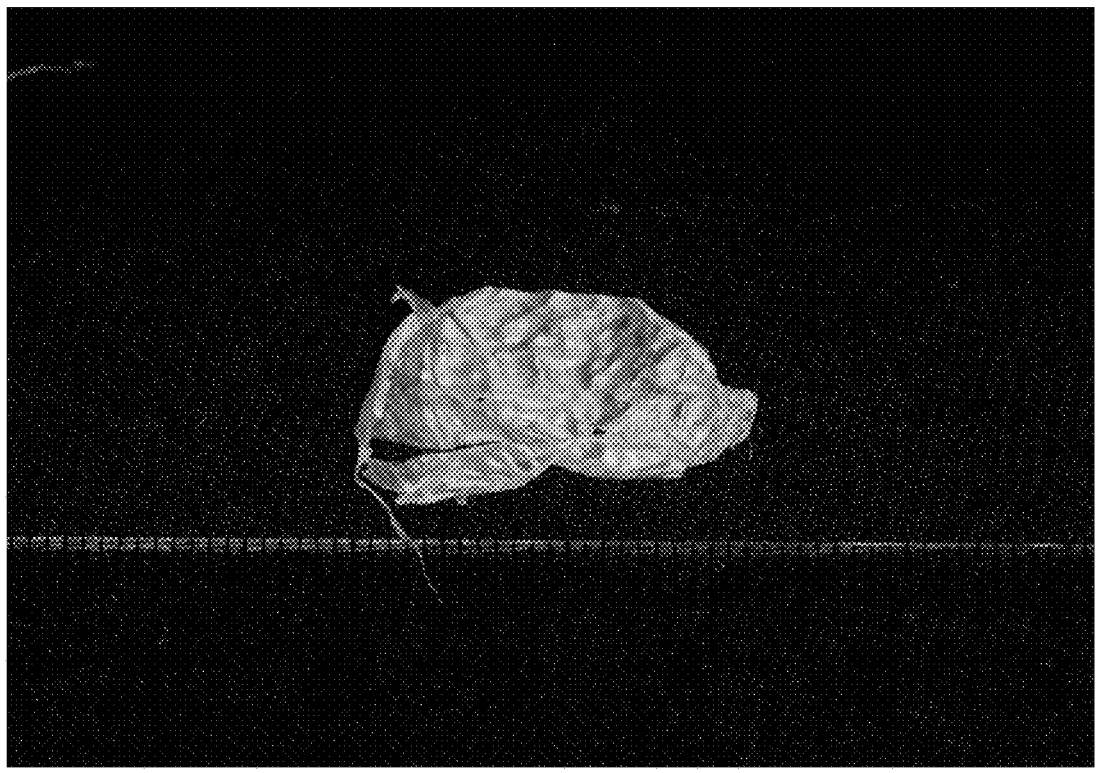
(FIG. 3C) Ultrathin membrane for use in the eye such as in the retina, BM or any anatomical part in the back wall of the eye.
Figure 3D:
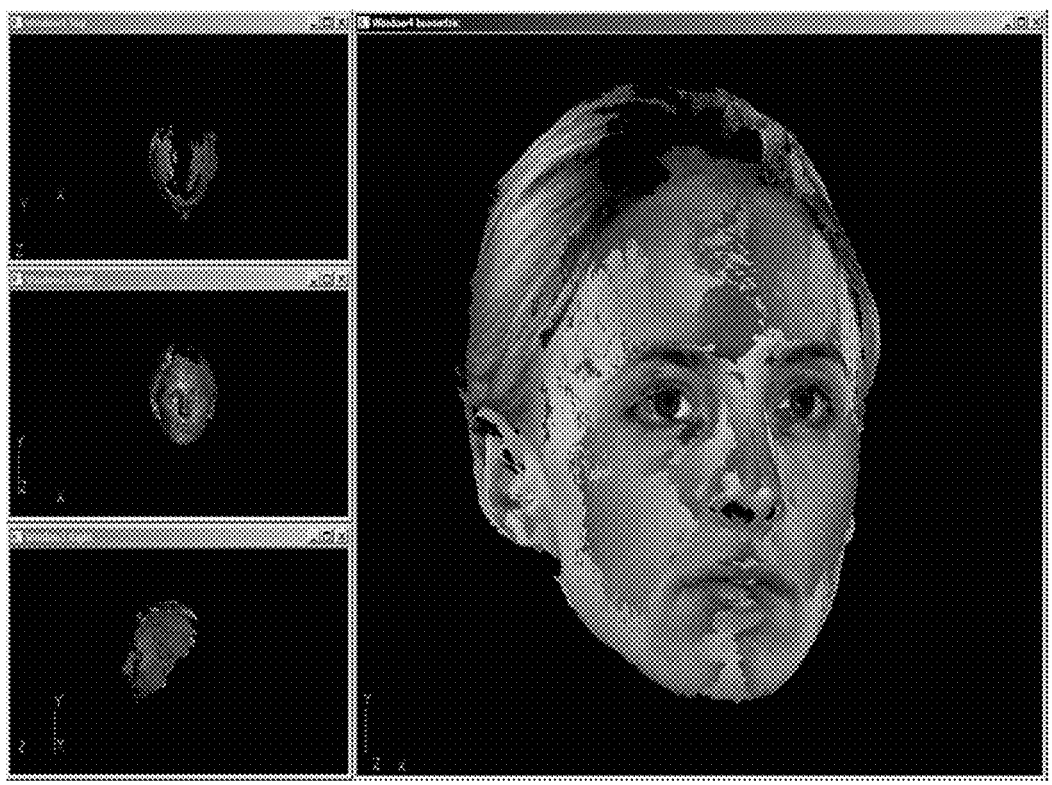
(FIGS. 3D to 3F) 3D photograph as a result of implementing 3D imaging techniques.
Figure 3E:
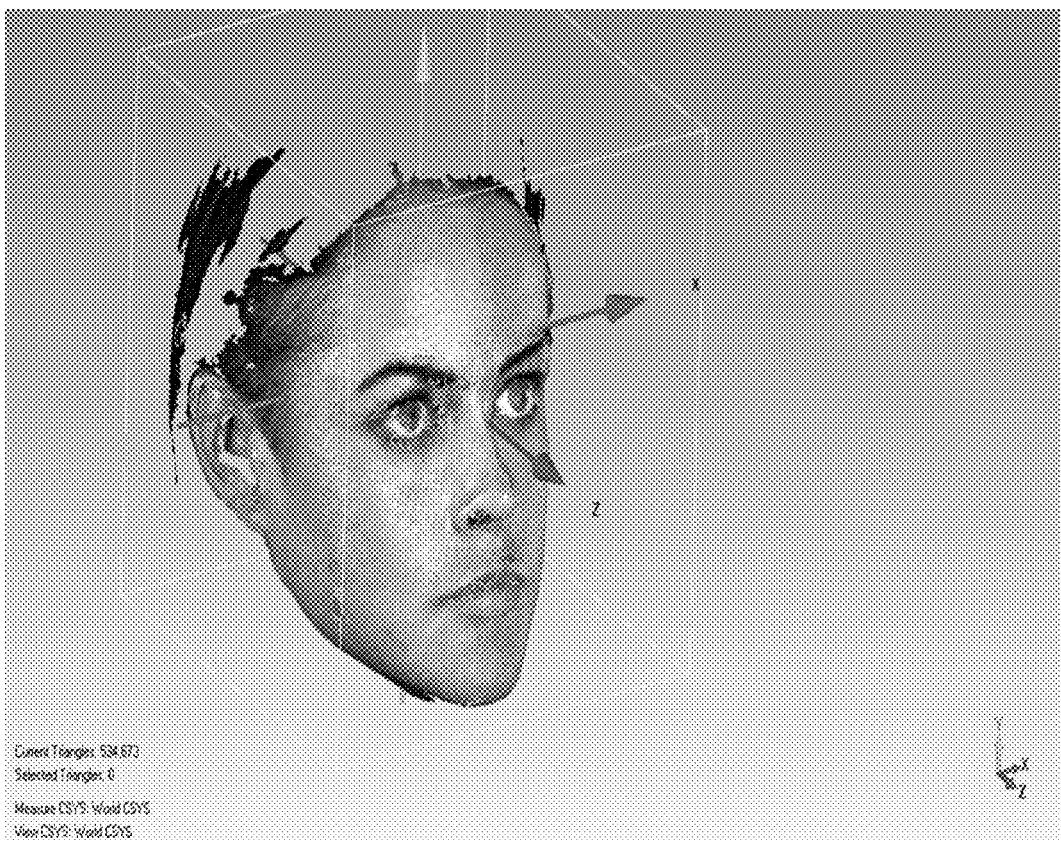
Figure 3F:
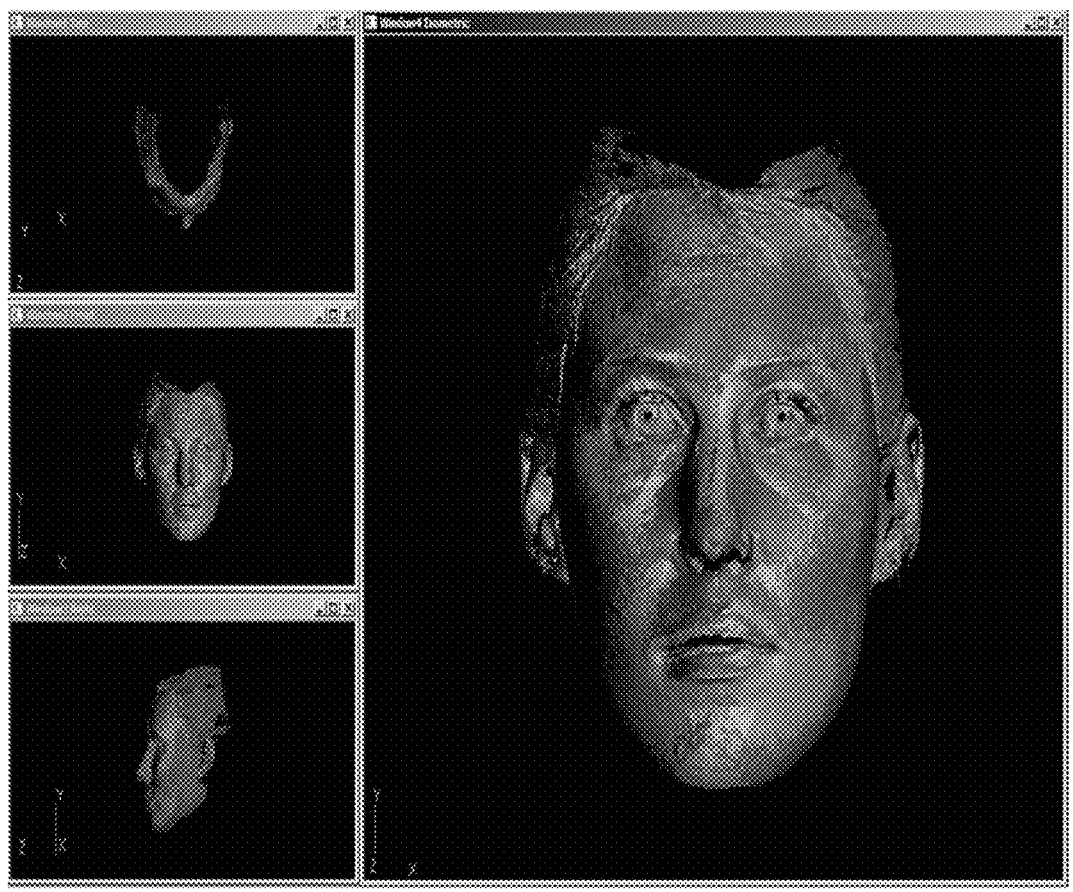

Steps (a) to (e) of the above described process can be replaced by the following steps: (g) Measuring the contour of the body part that requires tissue regeneration or repair by 3D imaging techniques; (f) Inputting the measurements into a design based application to prepare a physical model of the body; (h) Preparing the model; (i) Placing the model in an electric field of a nanofiber webbing machine; (j) Applying a 3D nanofiber webbing to the model to a desired thickness; and (k) Removing the 3D nanofiber webbing from the model. Any 3D imaging technique that has the ability to measure the contour of the body part that requires tissue regeneration or repair is contemplated herein. Non-limiting examples of 3D imaging techniques that are known in the art include Scan xray, CT scan, cone beam xray, MRI and 3D photography. Examples of 3D photograph are shown in FIGS. 3D to 3F. The inventor has contemplated the use of more than one type of 3D imaging technique. Any combination of 3D imaging techniques to achieve accurate measurements is contemplated herein. Any design based application which allows for the design of a model based on contour measurements gathered from the use of one or more 3D imaging techniques is contemplated herein. Non-limiting examples of a design based application include any design based application known in the art such as computer aided design (CAD) and rapid-prototyping. Non-limiting examples of rapid-prototyping include 3D printing, 3D selective lasering, 3D selective sintering, 3D casting, 3D burring, 3D grinding or any combination thereof.

Pre-Nanofiber Processing

To generate a customized tissue regeneration composition comprising three-dimensional (3D) nanofiber webbing for application to any body part that requires tissue regeneration or repair, a mould or model as described herein is prepared. In one example, the inventor used paper-mache to prepare a mould of a face (see FIG. 1 as an example), but any material that allows for the creation of a mould is contemplated. After the mould is created, it is filled with a material to make a cast. There are a variety of materials that are known in the art which are suitable for making a cast. In a non-limiting example, plaster-of-paris is one such material and is contemplated herein.

Nanofiber Processing

In a preferred embodiment, the cast (or the model as created by 3D imaging technique(s) and design based application(s)) is placed in a nanowebbing machine. Any machine that creates nanowebbing in a needleless fashion is contemplated herein. A non-limiting example of a nanowebbing machine is the NS Lab 200S (NANO-SPIDER®).

The cast or model is placed between two electrodes to create an electric field, but any design that creates a suitable electric field is contemplated herein and is within the scope of the invention. In a preferred embodiment, the distance between the electrodes is 21 cm.

Figure 2:
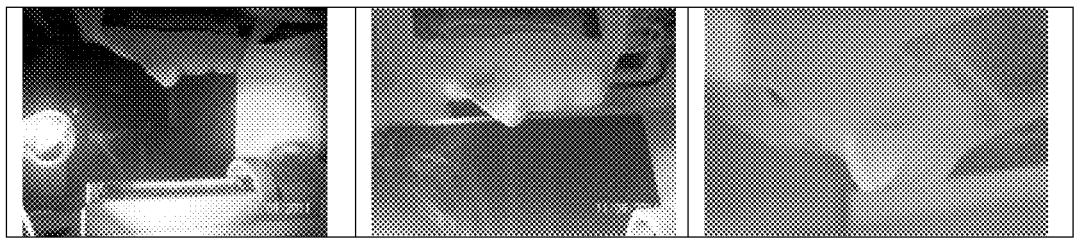
FIG. 2. Pictorial representation of the nanofiber processing. Formation of Taylor Cone is visible in left panel. Middle panel shows increase in the concentration of nanofibers travelling through the electric field. Right panel shows near completion of the nanofiber process with the cast completely covered by the nanofiber webbing.

In a preferred embodiment, the nanowebbing, which is a 3D structure of nanofibers, is created by spraying a biopolymer liquid onto the face of the cast or model during the nanowebbing process (see FIG. 2 as an example). The nanofibers travel though the electrical field against the cast or model. In one example, the applied voltage to create the electrical field is 35 kV but any voltage to allow travel of the nanofibers through the field is within the scope of the invention. The mechanical and chemical composition of the nanofibers can be altered during this process and is contemplated herein. Also, the morphology of the fibers will be affected by changing the processing conditions. The processing conditions have a lesser influence on producing the fibers than the solution properties; nevertheless, understanding these parameters is critical in obtaining the fibers with the specific morphology [Ramakrishna et. al. (2005)].

Some of the processing parameters that can influence the formation and morphology of the fibers are; applied voltage, the revolution of the spinning electrode, type of the electrodes used, distance between the two electrodes, and the type, the humidity, the temperature and the pressure of the atmosphere. Changing these parameters can influence the morphology of the fibers by changing the fly time, the speed of the acceleration, Taylor's cone stability, and the electric field strength [Ramakrishna et. al. (2005)].

Voltage

Generally, increasing the applied voltage will increases the electric field applied to the fibers. This will result in greater stretching of the fibers consequently decreasing the fiber diameter [Ramakrishna et. al. (2005); Jalili et. al. (2006)]. The stretching of the jet might be due to instability of the Taylor cone as the jet retreats to the tip of the syringe [Ramakrishna et. al. (2005)].

In the case of a polymer solution with a low viscosity, a high voltage may result in the formation of secondary jet, which results in the formation of fibers with a small diameter. However at lower viscosity, in some cases, reducing the voltage can also result in fibers of reduced diameter. In this case reducing the voltage, decreases the acceleration of the jet, as a result, the jet would have longer time to stretch and elongate before it is collected, thus reducing the fiber diameter [Ramakrishna et. al. (2005); Ki et. al. (2005)].

Electrode Rotation

The rotation of the electrode is set to deliver the solution at flow rate equal to the flow rate at which the electrified jet propels the polymer solution. As the charge reaches the critical point, a fluid jet will erupt from the solution. The erupted fluid jet forms a Taylor cone, moving toward the region of lower potential, which is the collecting electrode. To retain a stable Taylor cone for the corresponding voltage, the feed-rate of the solution can be adjusted by adjusting the revolution of the spinning electrode. Increasing the feed-rate will increase the amount of the polymers available to be drawn and will result in an increase in the diameter of the fibers formed. However due to an increase in the volume of the solution that is drawn, the jet might need a longer time for the solvent to evaporate [Ramakrishna et. al. (2005)].

Temperature

Large pores will be formed, if the temperature is high enough for the fibers to melt [Ramakrishna et. al. (2005)]. The high temperature could also affect the crystallinity of the electrospun fibers. A study where that used X-ray diffraction to assess the crystallinity of the electrospun nanofibers has been done.

An increase in temperature will decrease the viscosity of the solution. As well as speeding up the solvent evaporation [Ramakrishna et. al. (2005)].

Effect of the Collector

The collector can be conductive or non-conductive, depending on the packing density of the fibers required. Fibers deposited on a conductive collector will dissipate their charge allowing more fibers to be attracted to the collector. This results in a higher packing density. A scaffold with well-defined structure mimicking the native extra-cellular matrix has great potential in tissue engineering. The collector design can be used to change the resultant orientation of the collected fibers, aligned or randomly, to exhibit similar orientation to the extra-cellular matrix. Zhong and his group have used a rotating cylinder to fabricate aligned collagen scaffolds were they demonstrated it results in an increase in fibroblast proliferation [Zhong et. al. (2006)].

The Distance Between the Electrodes

Changing the distance between the electrodes will affect the flight time and electric field strength of the jet. At shorter distances, the flight time will be reduced. Furthermore the electric field will strengthen, increasing the acceleration of the jet. This will reduce the time for the solvent to evaporate, which might consequently result in merging of the fiber [Khil et. al. (2003)].

For some solvents, decreasing the distance between the needle and the collector might result in the formation of beads as result of the increase of the electric-field strength, which will result in acceleration of the jet consequently less time for the fibers to stretch [Ramakrishna et. al. (2005)].

Solution Properties

Although it is possible to electrospin molten polymer, polymer solutions are preferred. There are broad range of solvents that can be used for electrospinning; water, organic solvents, and oils. Also many polymers, co-polymers and mixtures of polymers can be electrospun. The choice of polymers and the solvents will influence the surface tension, conductivity, viscoelasticity and other properties of the solution. These solution properties have a major influence on the morphology, chemical and mechanical properties of the resultant fibers [Liang et. al. (2007)].

Surface Tension

For the electrospinning process to initiate, the charges applied to the solution must overcome the surface tension. The polymer solution's surface tension acts to decrease the surface area per unit mass of a fluid which tends to cause the formation of beads along the fiber length [Khil et. al. (2003)]. At low viscosity where there is high concentration of free solvent molecules, owing to surface tension, the affinity for the solvent molecule to adopt the spherical shape increases [Ramakrishna et. al. (2005)].

Viscosity

The molecular weight of the polymer affects the viscosity of the solution. In general, if a polymer with a higher molecular weight is dissolved in a solvent, it will result in a polymer solution with a higher viscosity than a polymer with a lower molecular weight. The solution must have polymers with a reasonable molecular weight, and has to have sufficient viscosity for electrospinning to occur. The entanglement of the molecule chains prevents the breaking of the polymer jet during the stretching of the jet [Ramakrishna et. al. (2005)].

A different way of increasing the viscosity is by increasing the concentration of the polymers within the solution. This will also result in an increase in the entanglement of the polymers, which is essential to retain the continuity of the jet during electrospinning [Ramakrishna et. al. (2005)].

As mentioned earlier, when the viscosity is too low, the surface tension has the dominant impact so it is common to find beads along the fiber length. As the viscosity increases there is a change in the bead's shape from spherical to a spindle-like until a smooth fiber is obtained. However at high viscosity, the fibers formed have a greater diameter, which is due to a greater resistance formed as result of increasing the amount of the entanglements [Ramakrishna et. al. (2005)].

At high viscosity there is a greater chance for the solution to dry and form an isolating layer between the spinning electrode and the solution, which will greatly affect the efficiency of the electrospinning The high viscosity of the solution also lessens the bending instability of the jet, which will result in smaller deposition area, and lesser stretching, which results in an even greater diameter [Ramakrishna et. al. (2005)].

Volatility (Evaporation Rate) of the Solution

As the jet travels toward the collector, the solvent will evaporate. If the rate of evaporation of the solvent is too low, and the solvent has not evaporated sufficiently by the time it reaches the collector, the fibers might merge and form inter and intra-layer bonding. This might be useful technique to provide additional strength to the resultant scaffold [Ramakrishna et. al. (2005)].

NS Lab200S uses the principle of free surface electrospinning. When using this method, one has to be watchful of using volatile solvent. It is recommended to use co-solvent when using volatile solvents. As a rule, the solvent must have: A boiling temperature between 80° C. to 200° C. at the atmospheric pressure; A saturation pressure between 0.35 to 10 kPa at 20° C.

Conductivity of the Solution

Electrospinning happens as a result of stretching of the solution caused by repulsion of the charges at the surface of the solution. As the conductivity of the solution increases, the jet will carry a greater charge. Thus an increase in the conductivity of the solution will result in greater stretching of the jet, resulting in smoother fibers with a smaller diameter. An increase in the amount of charge carried by the jet will also result in greater bending instability as a consequence of that greater deposition area will be achieved. However there are limits to the stretching of the fibers as result of the increase in the conductivity of the solution. This is due to the significance of the viscoelastic forces acting against the columbic forces of charges [Ramakrishna et. al. (2005)].

The increase in conductivity can be achieved by the addition of ions, or changing the pH of the solution. Natural polymers such as protein have high conductivity due to the formation of ions when mixed in solvent such as water [Ramakrishna et. al. (2005)].

Dielectric Effect of the Solvent

The dielectric constant of a solvent has significant effect on the stretching of the fibers. An increase in dielectric constant adds to the bending instability of the solution consequently increases the jet path. The outcome will be a larger deposition area and finer fibers [Ramakrishna et. al. (2005); Ki et. al. (2005)].

Curability

At least one curable biopolymer or resin or self-hardening clay could be added to provide shape stability and structural integrity to the composition.

Layers of Composition

The composition is multilayered. In a preferred embodiment, the composition is in the form of a membrane. The composition may comprise layers of differing polymers thus forming a composite. Two or more polymers may either be dispersed by the same liquid or contained in different liquids and dispersed separately, or even another method of applying the two or more polymers if the polymers are not in the form of a liquid. Each layer could have various mechanical, morphological or chemical characteristics. The polymer may be inert and provide support and rigidity to the overall structure of the composition. The layers may be interconnected through interweaving during the electrospinning process.

In addition, the composition may contain an agent. As a non-limiting example, the agent could be a physiochemical or therapeutic agent. As contemplated herein, the physiochemical agent covers any substance that has an affect on the human body, specifically, an affect on any function of a living body including interaction of biomolecules that carry out the chemical or physical functions that exist in the body. The physiochemical agent is natural, naturally derived, or synthetic. A therapeutic agent can be any therapeutic agent, for example, that has a medical purpose such as relieving or ameliorating inflammation at the site of the body part, functioning as a prophylactic in deterring any microbial infection, or assists in the general health of the tissues at or around the body part may be present in the 3D nanofiber webbing of the composition.

Therapeutic Agents

A wide variety of therapeutic agents can be employed including those used for the treatment of a wide variety of diseases and conditions associated with tissue such as skin tissue or tissue present within the body, i.e. internally. In one example, the internal tissue may be ocular tissue such as retinal tissue, BM, or any other tissue in the back wall of the eye for the treatment of AMD. Exemplary therapeutic agents include, but not limited to, cells, proteins, peptides, nucleic acid analogues, nucleotides, oligonucleotides, nucleic acids (DNA, RNA, siRNA), peptide nucleic acids, aptamers, antibodies or fragments or portions thereof, antigens or epitopes, hormones, hormone antagonists, growth factors or recombinant growth factors and fragments and variants thereof, cell attachment mediators (such as RGD), cytokines, enzymes, anti-inflammation agent, antifungals, antivirals, antiprion, toxins, nanodiamonds, prodrugs, chemotherapeutic agents, transcription inhibitory proteins, small molecules, drugs (e.g., drugs, dyes, amino acids, vitamins, antioxidants), other antimicrobial compounds, polyenes, guanine analogues, thymidine analogues, an organism such as a fungus, plant or animal, or a virus (including bacteriophage), neurotransmitters, hormones, intracellular signal transduction agents, pharmaceutically active agents, toxic agents, agricultural chemicals, chemical toxins, biological toxins, microbes, and animal cells such as neurons/nerve, liver cells, and immune system cells, pharmacological materials, vitamins, sedatives, hypnotics, prostaglandins and radiopharmaceuticals.

Antibiotics

Antibiotics or antimicrobial agents that can be embedded into the 3D nanofiber webbing of the composition of the present invention include, but are not limited to, actinomycin; aminoglycosides (e.g., neomycin, gentamicin, tobramycin); beta-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Methods of prevention and/or treatment of microbial contamination, particularly those caused by surgical site infection are encompassed by the present invention. Surgical site infections that may be treated or prevented by using the composition of the present invention, wherein the composition comprises one or more of any of the above listed antibiotics, include, but not limited to, the bacterial infections such as *Streptococcus pyogenes* (*S. pyogenes*), *Streprococcus viridian*, a-*Streptococcus, Pseudomonas aeruginosa* (*P. aeruginosa*), *Enterococcus faecalis* (*E. faecalis*), *Proteus mirabilis* (*P. mirabilis*), *Serratia marcescens* (*S. marcescens*), *Prevotella, Bacterioides, Enterobacter clocae* (*E. clocae*), *Acetinobacter anitratus* (*A. anitratus*), *Klebsiella pneumoniae* (*K. pneumonia*), *E. coli, S. aureus*, coagulase-negative *Staphylococci*, and *Enterococcus* spp, Clostridiae, Mycobacteriae, Fusiform bacteriae, Spirochaetes, Legionellae, Borreliae, spores and so forth. The composition of the invention is useful for any surgical site infection including, but not limited to, cosmetic, gynecologic, obstetrical, abdominal, orthopedic, oral and maxillofacial, head and neck generally, cardiothoracic, vascular, and colorectal surgeries.

Antimicrobial Substances or Peptides

The antibiotic agents may also be antimicrobial proteins or antimicrobial peptides such as defensins, magainin, nisin, lytic bacteriophage, indolicidin and protegrin-1. The antibiotic agents can also be the combinations of any of the agents listed above.

Cytokines

Any cytokine, such as an interferon or interleukin is contemplated as an agent that may be present in the 3D nanofiber webbing of the composition of the invention. As a non-limiting example, interleukin 1 to 33, 35 (IL-1 to IL-33, IL-35) and IFN-α, IFN-β, IFN-ω and IFN-γ are contemplated herein.

Growth and Morphogenic Factors

Growth and morphogenic factors are contemplated herein such as fibroblast growth factor (FGF), transforming growth factors (TGF) including transforming growth factor β (TGF-β), TGF-β1, TGF-β2, TGF-β3, vascular endothelial growth factor (VEGF), anti-VEGF such as Bevacizumab (AVASTIN™), epidermal growth factor (EGF), platelet derived growth factor (PDGF), PDGF-BB, insulin-like growth factors, bone morphogenetic growth factors, bone morphogenetic-like proteins, transforming growth factors, nerve growth factors, and related proteins (i.e. growth factors that are known in the art) are contemplated as an agent that may be present in the 3D nanofiber webbing of the composition of the invention.

Hormones

Any hormone is contemplated as an agent that may be present in the 3D nanofiber webbing of the composition of the invention. In a non-limiting example, a hormone may be a peptide hormone such as TRH, vasopressin, a insulin and growth hormone, glycoprotein hormones, a luteinizing hormone, a follicle-stimulating hormone and a thyroid-stimulating hormone; a lipid or phospholipid-derived hormone such as steroid hormones that derive from cholesterol and the eicosanoids e.g. testosterone and cortisol; or a monoamine derived from aromatic amino acids like phenylalanine, tyrosine, tryptophan by the action of aromatic amino acid decarboxylase enzymes. Calcitonin is also contemplated.

Anti-Inflammatory Agents

Anti-inflammatory agents that are steroid based such as corticosterone, budesonide, dexamethasone, prednisolone, estrogen, sulfasalazine and mesalamine are contemplated herein. Non-steroid anti-inflammatory agents contemplated herein include, but not limited to saliylates such as aspirin (acetylsalicylic acid), diflunisal, salsalate; propionic acid derivatives such as ibuprofen, naproxen, fenoprofen, ketoprofen, flurbiprofen, oxaprozin, loxoprofen; Acetic acid derivatives such as indomethacin, sulindac, etodolac, ketorolac, diclofenac, nabumetone; Enolic acid (Oxicam) derivatives such as piroxicam, meloxicam, tenoxicam, droxicam, lornoxicam, isoxicam; Fenamic acid derivatives (Fenamates) such as mefenamic acid, meclofenamic acid, flufenamic acid, tolfenamic acid; and selective COX-2 inhibitors (Coxibs) such as celecoxib, rofecoxib, valdecoxib, parecoxib, lumiracoxib and etoricoxib.

Kinase Inhibitors

Any protein kinase or tyrosine kinase inhibitor is contemplated as an agent that may be present in the 3D nanofiber webbing of the composition of the invention. Examples of kinase inhibitors include, but are not limited to, tyrphostins, genistein, and quinoxalines.

Anticancer Agents

Any anticancer is contemplated herein and include, but not limited to, tamoxifen, topotecan, LHRH, podophyllotoxin, colchicine, endostatin, raltitrexed, thiotepa, cyclophosphamide, busulfan, improsulfan, piposulfan, benzodopa, carboquone, meturedopa, uredopa, altretamine, triethylenemelamine, triethylenephosphoramide, triethylenethiophosphoramide, trimethylolomelamine, bullatacin, bullatacinone, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, a sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, calicheamicin, dynemicin, clodronate, an esperamicin, neocarzinostatin chromophore, an aclacinomysin, actinomycin, authrarnycin, azaserine, a bleomycin, cactinomycin, carabicin, caminomycin, carzinophilin, a chromomycin, dactinomycin, daunorubicin, detorubicin, 6-diazo-5-oxo-L-norleucine, epirubicin, esorubicin, idarubicin, marcellomycin, mycophenolic acid, nogalarnycin, an olivomycin, peplomycin, potfiromycin, puromycin, quelamycin, rodorubicin, streptonigrin, streptozocin, tubercidin, ubenimex, zinostatin, zorubicin, 5-fluorouracil (5-FU), denopterin, methotrexate, pteropterin, trimetrexate, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, a maytansinoid, mitoguazone, mopidanmol, nitraerine, pentostatin, phenamet, pirarubicin, losoxantrone, podophyllinic acid, 2-ethylhydrazide, procarbazine, PSK polysaccharide complex, razoxane, rhizoxin, sizofuran, spirogermanium, tenuazonic acid, triaziquone, 2,2',2"-trichlorotriethylamine, a trichothecene, urethan, vindesine, dacarbazine, mannomustine, mitobronitol, mitolactol, pipobroman, gacytosine, arabinoside, cyclophosphamide, thiotepa, doxetaxel, chlorambucil, 6-thioguanine, mercaptopurine, cisplatin, oxaliplatin, carboplatin, vinblastine, platinum, mitoxantrone, vincristine, vinorelbine, novantrone, teniposide, edatrexate, daunomycin, aminopterin, xeloda, ibandronate, irinotecan, retinoic acid, capecitabine, docetaxel, paclitaxel, 5-fluorouracil, cisplatin, vinblastine, vincristine, epothilones, endostatin, angiostatin, angiopeptin, monoclonal antibodies capable of blocking cell or tissue proliferation, and thymidine kinase inhibitors, RFS 2000 and difluoromethylornithine (DMFO); (l) anesthetic agents such as, bupivacaine and lidocaine ropivacaine; (m) anti-coagulants such as an RGD peptide-containing compound, heparin, D-Phe-Pro-Arg chloromethyl ketone, hirudin, antithrombin compounds, prostaglandin inhibitors, platelet inhibitors, platelet receptor antagonists, anti-thrombin and anti-platelet receptor antibodies and aspirin; (n) vascular cell growth promoters such as translational promoters, growth factors, and transcriptional activators.

Cells

As contemplated herein, the composition of the invention may contain cells that represent the cells that are required to regenerate the tissue. Representation means that cells in the composition are (a) of the same, (b) similar type that differentiates into the same type, (c) same origin, and/or (d) a different type that has the same function, to the cells of the tissue. For example, damage to retinal tissue may result in the loss of photoreceptor cells. The composition of the invention may be seeded with a number of photoreceptor cells or cells that differentiate into photoreceptor cells. Also, the composition may further comprise retinal pigmented cells and various types of nerve cells. There is contemplation herein that the cells are cultivated prior to the composition making contact with the body part or site that requires tissue regeneration.

Exemplary cells suitable for use herein may include, but are not limited to, progenitor cells or stem cells, adult or embryonic stem cells, adult differentiated cells, smooth muscle cells, skeletal muscle cells, cardiac muscle cells, epithelial cells, endothelial cells, urothelial cells, fibroblasts, myoblasts, skin cells, hair follicle cells, receptor cells, melanocytes, blood cells, all cells of muscles, bone, cartilage and vessels, endothelial cells, mucosal cells, immune cells, nerve cells, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, ocular cells such as corneal or retinal cells, retinal pigment epithelium, BM cells, any cells present in any anatomical part of the back wall of the eye and precursor cells. Stem cells may be various types of human stem cells, such as human mesenchymal stem cells (MSC), haemtopoetic stem cells, epithelial stem cells, neural stem cells, induced pluripotent stem cells (iPSC) or very small stem cells. Stem cells may also be from non-humans including any vertebrate such as a horse, pig, cow, chicken and sheep. The layers of the 3D nanofiber webbing may consist of more than one type of cell. For example, regeneration of retinal tissue or any other ocular tissue affected by AMD may require delivering photoreceptor cells including rods and cones, as well as neurons/nerves to a site in the eye that needs regeneration. In this example, it is contemplated herein that the composition of the invention would comprise at least three layers in the 3D nanofiber webbing, such as seven to eight layers, in which one layer would contain photoreceptor cells, another layer would contain retinal pigmented epithelial cells and a further layer would contain various nerve cells and the thickness of the composition is about the thickness of the tissue requiring regeneration.

Natural Tissue Fibers

Examples of natural tissue fibers contemplated herein include, but not limited to Elastin such as alpha-elastin, tropoelastin, any collagen type, matrigel, geltrex, laminin, poly-L-lysine, poly-D-lysine.

Enzymes

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

Cell Influencing and Interactive Substances

Substances such as purmorphamine, Activin A, Taurine, and Retionic Acid are contemplated herein as well as fibroblast growth factor (FGF), transforming growth factors (TGF) including transforming growth factor β (TGF-β), TGF-β1, TGF-β2, TGF-β3, vascular endothelial growth factor (VEGF), anti-VEGF such as Bevacizumab (AVASTIN™), epidermal growth factor (EGF), platelet derived growth factor (PDGF), PDGF-BB, insulin-like growth factors, bone morphogenetic growth factors, bone morphogenetic-like proteins, MTA (Mineral Trioxide Aggregate), transforming growth factors, nerve growth factors, and related proteins as known in the art.

Anesthetic Agents

Anesthetic agents contemplated herein include, but not limited to, lidocaine, articain, prilocaln, tetracain, bupivacaine and ropivacaine.

Thickness

The longer the nanowebbing process takes and the more nanofibers are layered on the cast or model, the thicker the webbing becomes. One or more additional biopolymers, one or more material and one or more substances may be applied to the model or cast either simultaneously or sequentially with the applying of the nanofiber webbing.

In a preferred embodiment, the completely formed 3D nanofiber webbing (with or without other materials and/or substances) undergoes a hardening process, so that the composition keeps the shape or contour of the body part that requires tissue regeneration or repair after removal (e.g. "peeling-off") of the composition from the cast or model. The nanofibers could be chemically or physically hardened or polymerized. Alternatively polymerization could be induced via light curing similar to the light curing of polymer filling at the dentist.

The thickness of the composition will vary as it depends on the deformity or abnormality of the body part that requires treatment. Generally, the thickness of the composition is between about 5 um and about 4 mm. In another embodiment, the thickness may be at least 100 nm without an upper limit.

The thickness of the nanofiber diameters (nanofiber diameter as opposed to layer diameter or thickness) may be between about 10 nm and about 2000 nm. In another embodiment, the thickness of the fibers in the composition may be between about 100 nm and about 100 um (macrofiber diameter, not layer diameter or thickness). The overall thickness of the resultant composition (layers) may be higher than 5 um. The thickness of the membrane could correspond to the thickness of the skin or other organ and be in between 1.4 to 4.0 mm, or it can be higher and reach other thicknesses of natural organs.

Material

Any material can be added to the composition which includes any synthetic or naturally derived substance that is added to any layer of the composition. It is contemplated that the material would be useful to (a) make the structure of the composition more rigid or more flexible; (b) capture molecules or cells into the 3D nanofibre webbing; (c) preserve one or more agents present in the 3D nanofibre webbing from degradation or postpone degradation, and/or (d) activate or inhibit one or more agents. The material can be gel, gas, cream, salve or a solid and be organic or inorganic. As contemplated herein, the material may include but not limited to minerals, ceramics, nanodiamonds, crystals, amorphous minerals as well as hydroxyapatite, fluorapatite, tricalciumphosphate, calciumphosphate for bone and hard (calcified) tissue. Also metals and alloys such as gold, silver, copper, zinc, tin, platinum, titanium, magnesium alloys are contemplated herein and alkaline metals such as Na, Ca, F, Li, K, Mg, plus Cl, Br, and Iodine. Specifically, the composition can contain at least one inorganic crystalline or amorphous mineral-like material; such as but not limited to fluorapatite, $(Ca_5(PO_4)_3(F,OH))$, hydroxyapatite, magnetite $(Fe_3O_4)$, and calcium carbonate $(CaCO_3)$. MTA (Mineral Trioxide Aggregate) to turn stem cells into dentine producing cells is also contemplated herein along with Calcitonin and Bisphosphonates.

The composition can contain at least one organic and inorganic nano-vesicles (nanoparticles). These nano-vesicles can be used to deliver at least one organic or inorganic therapeutic substance. The therapeutic agent can either be loaded within the nano-vesicles and/or nanoparticles, or they can form temporary or permanent chemical bond (covalent bond, polar covalent bond, ionic bond, metallic bond, hydrogen bond). Example of these organic and inorganic nano-vesicles can be micelles, polyelectrolyte capsules, aluminosilicate, aluminosilicate nanotubes, silk nanoparticles, clays nanoparticles, self-assembled monolayers, synthase capsid, or self assembled capsules prepared by layer by layer techniques using peptides, protein, and polymers and inorganic mineralize. Example of layer-by-layer capsules are poly(L-glutamic acid)/chitosan microcapsules used for drug delivery that can be incorporated with the nanowebbing. The composition containing at least one organic and inorganic nano-vesicles, nano-particle, nano-capsules, micro-capsules, can be prepared by co-electrospinning using the nanowebbing technique, or by combining needle-electrospinning along with the nanowebbing technique or emulsion electrospinning method or coaxial electrospinning or combination of these techniques.

Use

Figure 10:
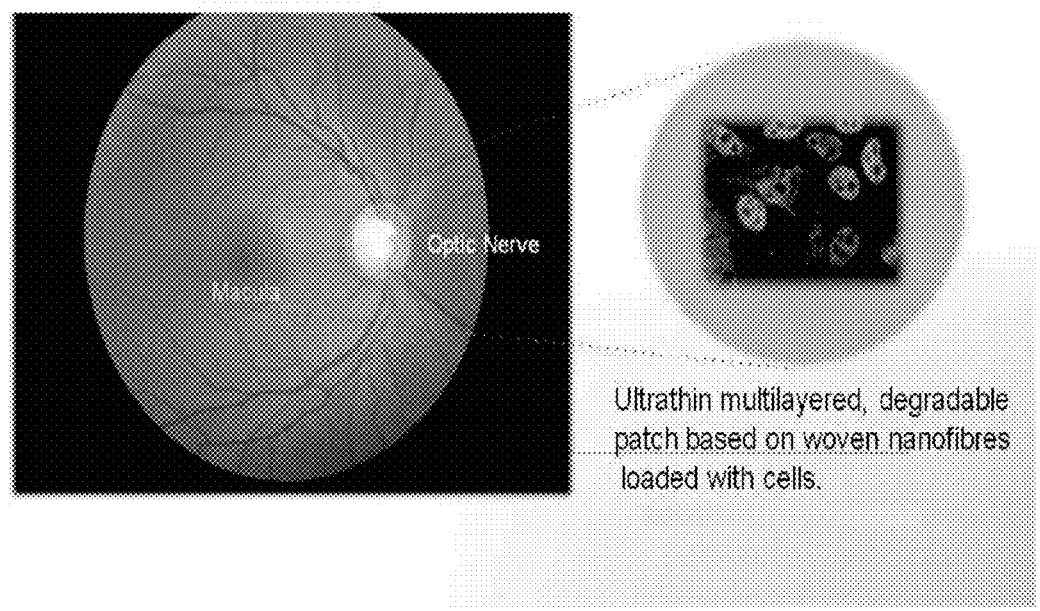
FIG. 10. Images of macula within the eye and the composition as a patch/membrane comprising stem cells.
Figure 11:
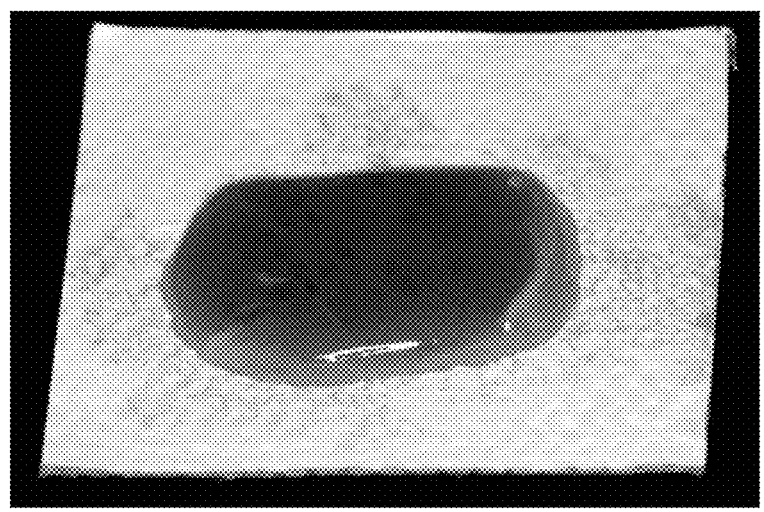
FIG. 11. Images of the composition as a nanofibrous membrane comprising collagen gel. In lower panel (B), the gel is compressed into the membrane thus forming a bilayer composition.
Figure 11:

Due to the presence of materials, substances and biopolymers in the composition, the composition has the ability to adequately protect the tissue against infection and heat loss. It also enables regeneration of blood supply and dermal skin cells while resisting rejection since there is no donor tissue component. The composition is biodegradable and thus allows the growth of any cells delivered by the composition to grow harmoniously with the cells of the natural skin which prevents scarring and contractures. Use of a customized skin tissue regeneration composition comprising 3D nanofiber webbing may be applied to any body part that requires tissue regeneration or repair. As contemplated herein, use of the composition can be for treating skin deformities or abnormalities. Abnormalities may include chronic wounds such as diabetic foot ulcers. The composition may be used to treat macula degeneration by applying the composition as a patch or membrane (with stem cells for example) to the back of the eye (i.e. retina, BM, optic nerve). See FIG. 10.

Surface and Shape

The present invention provides a customized tissue regeneration composition comprising three-dimensional (3D) nanofiber webbing. The surface of the composition may be porous or impermeable. The shape of the composition may be any form that contours to the body part that requires tissue regeneration or repair.

Polymers

Polymers which may be used to form the 3D nanofiber webbing for use in the invention include synthetic and natural polymers. Examples of synthetic polymers, include, but not limited to, Nylon 4,6 (PA-4,6), Nylon 6 (PA-6), Nylon 6,6 (PA-6,6), Polycrylic acid, Polyacrylonitrile, Polyamide-6 (PA), Poly(benzimidazol) (PBI), Polycarbonate, Polycarbonate Bisohenol-A, Poly(etherimide) (PEI), Poly(ethyl oxide) (PEO), Poly(ethylene terephtalate) (PET), Polystyrene (PS), Poly(styrene-butadiene-styrene), Polysulfone Bisphenol A, Poly(trimethylene terephthalate), Poly(urethane) (PU), Poly(urethane urea), Poly(vinyl alcohol) (PVA), Poly(vinyl carbazole) (PVK), Poly(vinyl chloride) (PVC), Poly(vinyl pyrrolidone) (PVP), Poly(vinylidene fluoride) (PVDF), Poly(vinylidene fluoride-co-hexafluoropropylene) (PVDF-HFP), Poly(ethylene-co-vinyl acetate) (PEVA), Poly(methacrylates) (PMMA), and polyacrylamide (PAAm). Synthetic or natural polymers may be biodegradable polymers. Synthetic biodegradable polymers include, but are not limited to, Poly(esterurethane), poly($\epsilon$-caprolactone) (PCL), Poly(dioxanone), Poly(glycolide) (PGL), Poly(L-lactic acid) (PLA), Poly(L-lactic-co-$\epsilon$-caprolactone), Poly(D,L-lactide-co-glycolide), Poly(L-lactide-co-glycolide), Poly(lactide-co-glycolic acid) (PLGA), Any homopolymer and co-polymer of Glycolide, lactide (L-lactide, D-lactide, D,L-lactide), $\epsilon$-caprolactone, Poly(glycerol sebatate) (PGS), Cellulose Acetate, Polyphosphazines, Polyanhydrides and Polyorthoesters. A natural polymer is contemplated herein and comprises proteins, lipids and/or polysaccharides. Natural biodegradable polymers include proteins, for example, selected from poly (amino acids), polyether imide (PEI), polyaniline, laminin, wheat gluten, silk, fibrin, fibrinogen, collagen type I, II, III and IV or any collagen type or sub-type that is known to the person skilled in the art, casein and elastin, and polysaccharides, for example selected from chitosan, gelatin, starch, cellulose acetate, and glycosaminoglycans such as chondroitin sulfate, dermatan sulfate, keratan sulfate, heparin, heparan sulfate, and hyaluronic acid. A mix or blend of the above natural and synthetic polymers may be used in forming the composition of the invention. It is also contemplated that the composition may be absent of a polymer, such as, silk.

Various preferred embodiments are discussed below in which the biodegradable polymer is or/and contain a protein such as collagen type I and/or laminin and/or matrigel and/or geltrex, or other therapeutic agents.

Collagen type I is the major constituent of the natural extra-cellular matrix. Because of its natural origin, non-immunogenicity, biocompatibility and its role in cell adhesion and migration, it plays a significant role as major component of the extra-cellular matrix. Type I collagen has wide application in designing a biological membranes such as BioGide.

In certain embodiment, the collagen and PLGA membranes at different composition (0% collagen: 100% PLGA, 25% collagen: 75% PLGA, 50% collagen: 50% PLGA, 75% collagen: 25% PLGA, 100% collagen: 0% PLGA and other concentrations) with at least 40 µm thickness have been electrospun and cross-link to form at least one layer of the final composition.

In certain embodiment, the type I collagen in the bioerodible polymer-containing layers of the invention is cross-linked, consequently reducing the degradation rate and solubility of the layer. Controlling the degradation rate consequently leads to controlling the release of the therapeutic agents integrated into the composition.

In certain embodiment the layer containing collagen and gelatin was cross-linked and surface-modified by zero-length cross-linker N,N-(3-dimethylaminopropyl)-N'-ethyl-carbodiimide hydrochloride (EDC). N-hydroxysuccinimde (NHS) at the ratio of EDC:NHS 5:1 was added to the cross-linking process to increase the efficiency of the cross-linking. Other agents can also be used in cross-linking: genipin, aldehydes (formaldehyde, glutaraldehyde, glycreraldehyde), polyepoxides, dicyclohexylcarbodiimide (DCC) and isocyanates.

Zero-length cross-linking was also used to surface-modify at least one layer of the composition by addition of therapeutic agent containing reactive groups (e.g. carboxyl group) such as retinoic acid, laminin, and collagen. Cross-linking, coupling, conjugation, "click" chemistry such as cycloaddition reactions e.g. Huisgen 1,3-dipolar cycloaddition, Cu(I) catalyzed azide-acetylene cycloaddition, Diels-Alder reaction, nucleophilic substitution to small strained rings (e.g. epoxy and aziridine rings), formation of ureas and amides and addition reactions to double bonds, e.g. epoxidation, dihydroxylation, nucleophilic substitution of a benzyl halide (e.g. chloride or bromide) group and any other activation process known and used in the art are contemplated herein. Any activation process that enhances delivery of one or more agents to the tissue that requires regeneration or repair is contemplated.

EXAMPLES

Example 1

Preparation of a Face Mould

In one aspect of the invention, the process of preparing a customized tissue regeneration composition comprising three-dimensional (3D) nanofiber webbing begins with the preparation of a mould of the body part that requires tissue repair or regeneration.

In one example, the inventor used paper-mache to prepare a mould of a face. The steps were the following.

Face was covered with a thin coat of vaseline

Paper-mache was cut into small pieces roughly 7×15 cm

The mesh was briefly immersed in warm water before placing them on the face

The mesh was gently massaged onto the skin to take the form of the face 3 layers of the mache was applied The mould was allowed to dry for 20 minutes before gently pulling the mould off the face The cast was prepared by preparing a mixture of 2 parts water and 3 parts plaster The plaster was mixed using a stirrer The mixture was then gently poured into the mould The cast was allowed to dry for 24 hours Once the plaster was set it was separated from the mould and placed in an oven at 180° C. for 30 minutes FIG. 1 provides a pictorial representation of the steps in preparing the face mould.

Example 2

Process for Spinning Nanofibers

The next step is to apply the 3D nanofiber webbing to the cast of the face. The nanofibers are spun into a web. Spinning (or electrospinning) is achieved by a needle-less device such as NS Lab 200S (NANO-SPIDER®). To begin the process, the following steps were taken:

The polymer solution must be prepared inside a fume hood

Once appropriate solvent for the polymer is selected, a polymer solution at various concentrations can be prepared (to investigate the effect of the solution concentration at nanofibers' morphology). The solvent can be any inorganic or organic solution, or combination of solvents.

To assist dissolving of the polymer use at least one of the following equipments: a magnetic stirrer, a shaker or a sonicator.

The Vials should be labelled with the polymers' name, concentration in solvent/solvents used and the date.

Once the polymer is completely dissolved, the polymer solution properties should be investigated and recorded.

The solution should be transferred to the spinning chamber in a sealed bottle to avoid inhaling any of the fumes Install the collecting electrode and Earth the collector using a 5.5-8 mm² copper wire Adjust the height of the collector Insert the spinning electrode (wire spinning electrode, cylinder spinning electrode, spiked spinning electrode) into the spinning tub by inserting the shaft end of the spinning electrode into the gear holder Load the spinning tub into the spinning tray Lock the spinning tub by rotating the lock slit into the spinning tray Pour the polymer solution into the spinning tub (mix the solution using a spoon before pouring the solution into the tub)

Place the high voltage shield above the gear holder

Shut and lock the main entrance door to the spinning chamber

Plug in and turn on the NS Lab200S

Turn on the main switch placed underneath the main entrance door. The "Suction Fan" Pilot (green light) lights up, indicating that the exhaust fan is running Press the start button switch (green). The "Supply Voltage" Pilot light up indicating electrical parts are connected.

Press the Safety Lock (blue) button

Turn on the lights by turning the switch (Black two-position selector) into the On position Start the electrode rotation and set the revolution (Must set the speed of the rotation according to the electrospinning parameters)

Set the output voltage to zero using the Voltage Dial Potentiometer

Set the output current to the maximum "10" using the Current Dial Potentiometer

Once all parameters are set, switch on the power supply using the Black Power Rocker Press the Red High Voltage Switch to enable the generation of high voltage After the above steps have been completed, the voltage will need be adjusted as per the following steps.

Once the Red has been pressed the high voltage is generated

Using the Voltage Potentiometer, Gradually increase the applied voltage to a value were nanofibers start to appear Another way to check the formation of the nanofibers is by observing the changes in the current, as the current exceeds 0.001-0.002 mA the mass transfer between the two electrodes initiates.

Applied voltage can be increased if the nanofibers formation seems to be weak

To get the best nanofibers, one needs to electrospin the solution at different voltage and access the fiber morphology and diameter using a Scanning Electron Microscope.

After the above steps have been completed, the procedure will need to be stopped as per the following steps.

Press the Red High Voltage Switch to disable the generation of high voltage

Switch off the power supply using the Black Power Rocker

Set the output voltage to zero using the Voltage Dial Potentiometer

Stop the electrode rotation

Turn off the lights by turning the switch (Black two-position selector) into the off position Press the stop button switch (Red)

To access the spinning chamber, unlock the main entrance door

Use the grounding Rod to eliminate any residual charge within the chamber

Turn off the main switch placed below the main entrance door

Unplug the machine

Example 3

Nanowebbing Process with Face Cast

The impression cast of the face (plaster-of-paris) as described in Example 1 was subjected to the nanofiber processing as described in Example 2. Specifics are described below.

The cast was placed on a wire-grounded collector inside the Nano-Spider machine. The cast was fixed to the collector using double sided tape. Subsequently, 8% gelatin was poured into nanowebbing machine tub. Webbing electrodes, in particular pike electrodes, was used for this procedure but cylinder electrodes, wire electrodes can be used. The operation was started and optimised. The best operating parameters were found to be 80 kV when the distance between the electrodes was set to 21 cm. The spinning electrode was set to 15 Hz. The formation of Taylor Cone (visible in FIG. 2, left panel) indicates the initiation of the process at 35 kV.

The nanowebbing process was stopped after sufficient thickness was achieved and the resulting composition (see FIG. 3A) was removed from the cast by a peeling manner. The composition in the form of membranes has also been produced (see FIGS. 3B and 3C).

Example 4

Biocompatibility Tests of Membranes

Several compositions in the form of membranes were manufactured by nanowebbing individual biopolymers. The biopolymers tested are poly lactic-co-glycolic acid (PLGA), gelatin and Poly-ε-caprolactone (PCL). The manufacturing process was similar with each polymer. As a representative example, the processing of a membrane manufactured by nanowebbing PLGA is described below. Specifically, The PLGA (85/15 L-lactide/Glycolide copolymer (molar ratio) (Purasorb PLG8531, Purac, Netherlands)) polymer solution was prepared inside the fume hood 12 grams of PLGA was weight and poured into a 200 ml glass bottle 188 grams of 2,2,2-Trifluoroethanol (ACR139755000, ThermoFisher, USA) was weight and poured directly onto the 200 ml glass bottle containing the PLGA A 15 mm magnetic rod was placed within the bottle The bottle was closed and sealed using paraffin film The bottle was then labelled and dated The bottle containing the PLGA and the solvent was placed on a magnetic stirrer and the solution was stirred for 4 hours at 500 rpm, till the polymer was fully dissolved 40 ml of 70% v/v Acetic Acid (which was prepared earlier by mixing 70 ml of Glacial Acetic Acid (A9967, Sigma Aldrich, USA) and 30 ml of deionised water) was added to the solution.

The bottle was shut and sealed again and stirred overnight

The solution was transferred to the spinning chamber

The collecting electrode was unscrewed and detached from the spinning chamber.

Using the electrode distance button the collecting electrode was lowered 4 bolts placed on the top of the electrode were loosen The collector (e.g. model or cast) was placed and held on the collector's platform using a copper wire The collector was then earthed using a 5.5-8 mm² copper wire The height of the collector was adjusted using the electrode distance button placed at the rear of the machine The wire spinning electrode was then placed into the spinning tub by inserting the shaft end of the spinning electrode into the gear holder The spinning tub was then loaded into the spinning tray The spinning tub was then locked into the tray by rotating the lock slit into the spinning tray The polymer solution was then mixed using a spoon and then poured into the spinning tub The high voltage shield was placed above the gear holder The main entrance door to the spinning chamber was then shut and lucked by two DIRAK locks.

The NS Lab200S machine was plugged in

The machine was turned by the main switch placed underneath the main entrance door. The "Suction Fan" Pilot (green light) lighted up, indicating that the exhaust fan is running The start button switch (green) was pressed. The "Supply Voltage" Pilot lighted up indicating electrical parts are connected.

The Safety Lock (blue) button was pressed

The chambers' lights were turned on by turning the switch (Black two-position selector) into the On position The electrode rotation was started and the revolution was set to 8 rpm The output voltage was set to zero using the Voltage Dial Potentiometer The output current was set to the maximum "10" using the Current Dial Potentiometer Once all parameters were set, the power supply was turned on using the Black Power Rocker The Red High Voltage Switch was pressed to enable the generation of high voltage The voltage was slowly increased to 50 kV The nanofibers were collected for 5 minutes, and then allowed to air dry for 10 minutes.

The copper wire were loosen and the collector was turned over

The cooper wire were tighten firmly and the earth connection was checked

The spinning was initiated again

The above steps were repeated till a sufficiently thick layer of electrospun nanofibers was covering the entire collector Cover-glass and Biogide (which are commercially available and clinically approved collagen membrane; Geistlich Company, Wolhusen, Switzerland) served as controls.

The membranes and the controls were seeded with human mesenchymal stem cells and proliferation and cell survival was tested with the standard WST assay as known by a person skilled in the art.

Figure 4A:
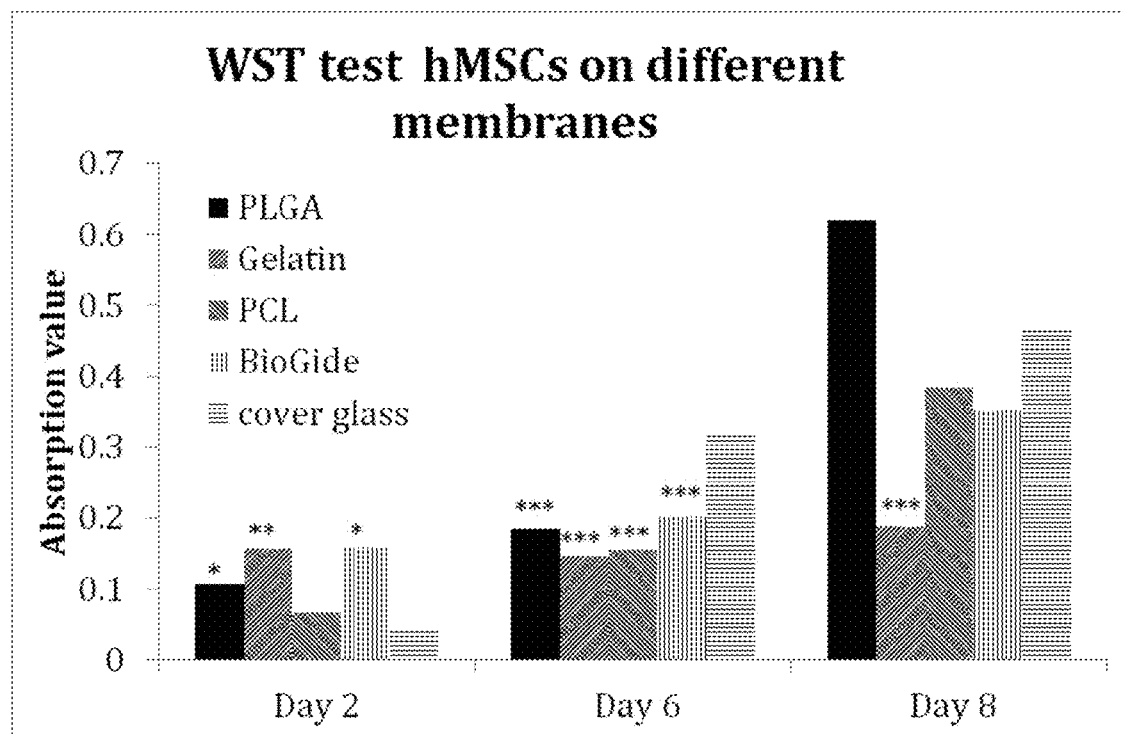
(FIG. 4A) WST-I test: Proliferation of human mesenchymal stem cells (MSC) seeded on PCL, gelatin, PLGA, cover-glass and BioGide Collagen membranes.
Figure 4B:
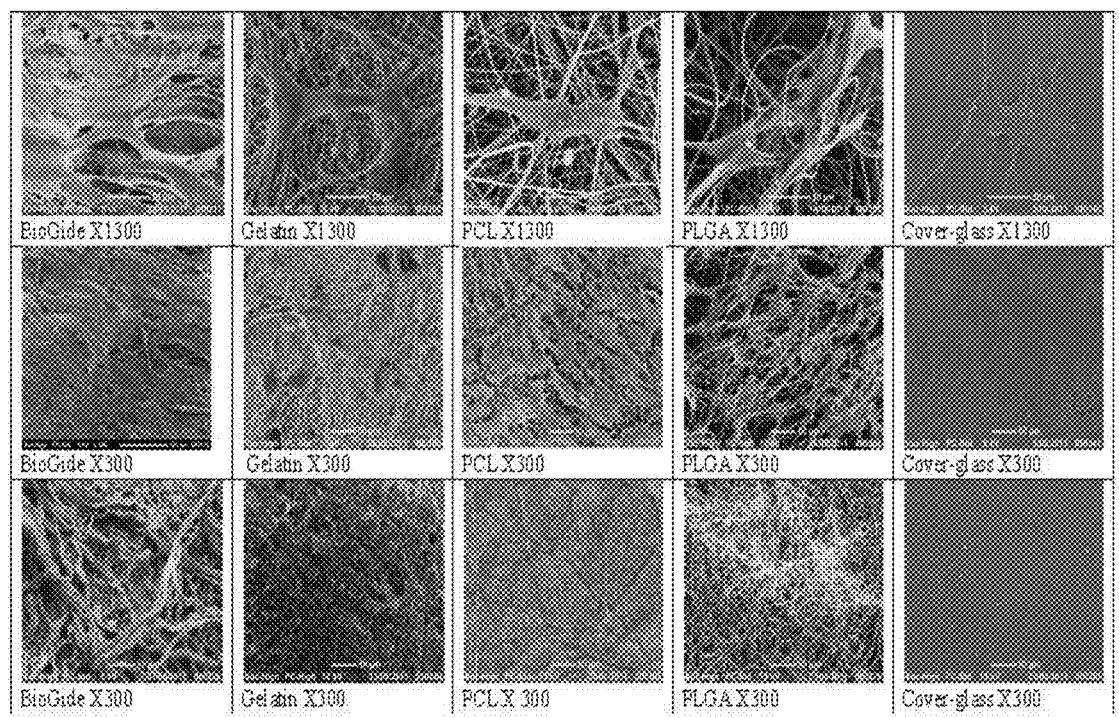
(FIG. 4B) SEM imaging of the cells as an indication of cell proliferation on each of the membranes made and studied.

After 8 days of culture, the PLGA membranes showed significantly better cell proliferation and survival than the controls (see FIG. 4A (histogram) and FIG. 4B (micrographs)). Our PCL membrane was comparable to the controls. The Gelatin membrane showed moderate but acceptable performance as cells were still active after 8 days of culture.

Example 5

Degradation Rate of Nanowoven Gelatin Membranes

The membranes of face replacements should be biodegradable over time, so that natural tissue can replace and grow into the space provided by the degrading fibers.

The samples were immersed in PBS at 37° C. for 21 days. The degradation rate was measured every 7 days by calculating the mass loss percentage. The samples were dehydrated using 30%, 50%, 70%, 90%, and 100% ethanol, and then allowed to air-dry for an hour before weighing. for 21 days. The mass loss percentage was measured using the following formulas [Kim et. al. (2009)].

$$\text{Mass loss}(\%)=[(W0-Wt)/W0]\times 100$$

W0=initial mass (g)
Wt=mass (g) of the samples at time t

Figure 5:
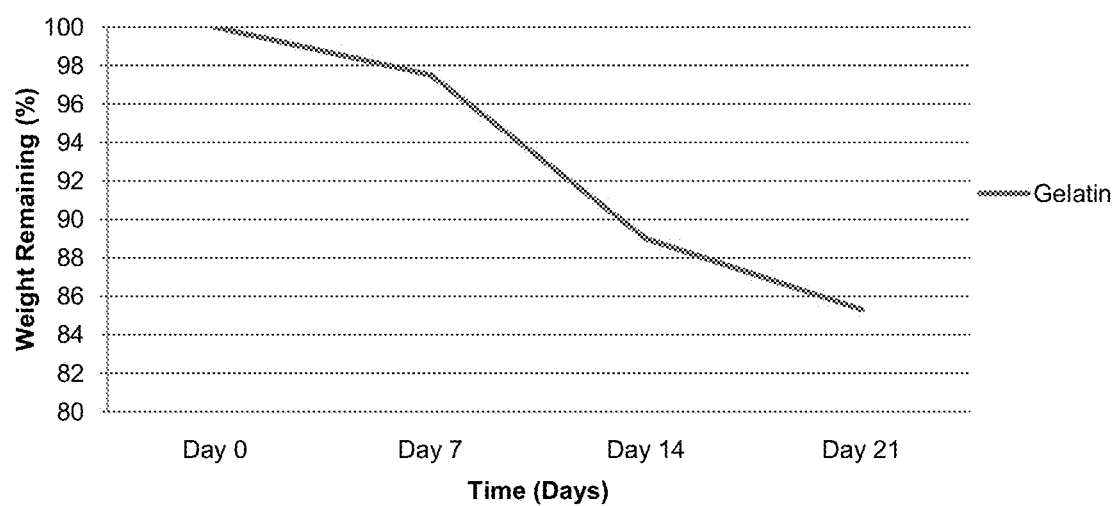
FIG. 5. Biodegradation test with Gelatin membrane.

As shown in FIG. 5, the gelatine gelatin face replacement membrane has a degradation pattern allowing for replacement by natural tissue over the course of a few weeks, specifically 21 days.

Example 6

Surface Modification

Using the equation shown below, a select number of biopolymers with reactive carboxyl group were surface-modified with drugs, cytokines, and growth factor. As a first step, a polymer after fabrication is weighed and immersed with ethanol containing 1-ethyl-3-(3-dimethyl aminopropyl) carbodiimide (EDC) and/or N-hydroxysuccinimide (NHS).

The below formulas are used to calculate the amount of EDC and/or NHS that is required for cross-linking and surface modification.

$$\text{Mass of the polymer} = \text{Mass of the membrane} \times \text{composition of the polymer}$$

$$\text{Number of mol of polymer} = \text{mass of polymer/molecular weight}$$

$$\text{Number of mol of reactive sides}(n(Re)) = \text{number of mol of polymer} \times \text{number of } Re \text{ in the each molecule}$$

$$\text{Required } n(EDC) = n(Re) \times 10$$

$$\text{Required } n(NHS) = 2(Re)$$

$$\text{Required } n(Drug) = n(Re) \times \text{ therapeutic level}$$

$$\text{Mass}(EDC) = n(EDC) \times Mw(EDC)$$

$$\text{Mass}(NHS) = n(NHS) \times Mw(NHS)$$

$$\text{Mass(Therapeutic Drug)} = n(Drug) \times Mw(Drug)$$

The membrane is allowed to cross-link for 24 hours, depending on the degree of the cross-linking required. The above formulas also apply for surface-modification of the nanofibers allowing addition of at least one therapeutic substance, such as laminin, collagen, and calcitonin.

Example 7

Preparation of Layer Containing Collagen and PLGA Composition

6% PLGA solution was prepared using 1,1,1,3,3,3-hexafluoro-2-propanol (HFIP) as the solvent. 6% collagen solution was prepared using the same solvent HFIP. Both solutions were sonicated for 30 minutes before being left on a magnetic stirrer overnight. Once the collagen and the PLGA were completely dissolved they were mixed at different concentration (0% collagen:100% PLGA; 25% collagen:75% PLGA (1:3); 50% collagen:50% PLGA (1:1); 75% collagen: 25% PLGA (3:1); 100% collagen:0% PLGA and other concentrations). The solutions were spun using nanowebbing technique. 5 kV was applied to the pike spinning electrode. The nanoweb was collected on an aluminium foil placed on the collecting electrode located at 15 cm away from the spinning electrode. 25 repeats each time 40 ul of the solutions were spun, to obtain a sufficient thickness of the layer.

The membranes where then sterilized using 70% ethanol and double strength antimycin-antibiotic solution, and washed with PBS before seeded with human mesenchymal stem cells (hMSCs).

The membranes and the controls were seeded with hMSCs and proliferation and cell survival was tested with the standard WST assay as known by a person skilled in the art.

Figure 6:
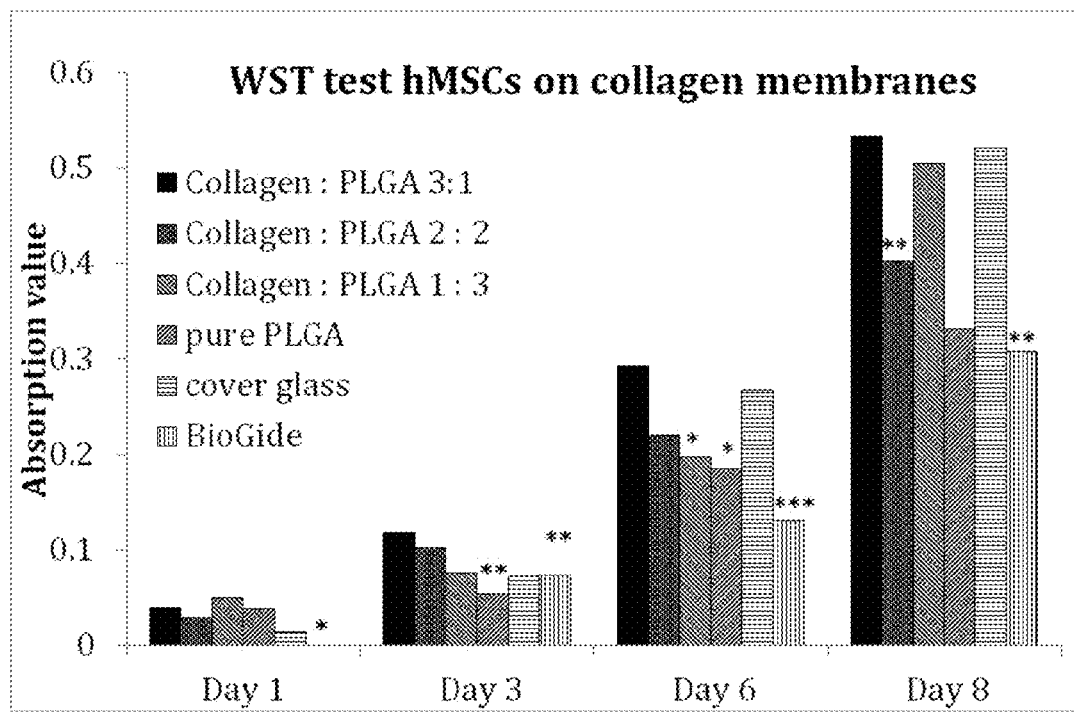
FIG. 6. Preparation of layer containing Collagen and PLGA composition: WST-I test: Proliferation of human mesenchymal stem cells (MSC) seeded on the following membranes (0% collagen:100% PLGA; 25% collagen:75% PLGA (1:3); 50% collagen:50% PLGA (1:1); 75% collagen: 25% PLGA (3:1); BioGide Collagen membrane and cover-glass).

Cell proliferation and survival were tested at days 1, 3, 6 and 8. After 8 days of culture, collagen:PLGA (3:1) membrane showed better cell proliferation and survival than the controls (see FIG. 6).

Example 8

Clinical Grade Electrospinning Methods

These studies relate to the application of clinical grade electrospinning methods to produce the compositions of the invention.

Novel clinical grade electrospinning methods could provide 3-dimensional (3D) nanostructured biomaterials comprising of synthetic or natural biopolymer nanofibers. Such advanced materials could potentially mimic the natural extracellular matrix (ECM) accurately and may provide superior niche-like spaces on the subcellular scale for optimal stem-cell attachment and individual cell homing in regenerative therapies. The goal of these studies was to design several novel nanofibrous extracellular matrices (NF-ECMs) with a natural mesh-like 3D architecture through a unique needle-free multi jet electrospinning method in highly controlled manner to comply with good manufacturing practices (GMP) for the production of advanced healthcare materials for regenerative medicine, and to test cellular behavior of human mesenchymal stem cells (HMSCs) on these.

1. MATERIALS AND METHODS 1.1. Polymer and Copolymer Solution Preparation

Two synthetic biodegradable polymers were chosen for these studies: Firstly, Poly(L-lactide-co-glycolide) (PLGA) with a molar ratio of 85:15 L-lactide:glycolide (purchased from Purac Biochem, Netherlands) and secondly, Poly(caprolactone) (PCL; from Sigma, Mo., USA). In addition, two natural biopolymers bovine collagen type I (Sigma, Mo., USA, Lot #078k7016V, Pcode 1001116870, extracted from calf skin using Bornstein and Traub protocol) and bovine gelatin (Sigma, Mo., USA) were selected. The polymers were dissolved in 1,1,1,3,3,3-hexafluoro-2-propanol (HFIP; ThermoFisher, Victoria, Australia) at a concentration of 10% wt/v. To aid dissociation of collagen, sonication was employed for 30 minutes. To prepare copolymer solutions of synthetic and natural biopolymers; PLGA:collagen, PLGA:gelatin, PCL: collagen or PCL:gelatin, each polymer was dissolved in the HFIP separately and then combined at appropriate ratios (3:1, 1:1 or 1:3). Immediately after their preparation the polymer solutions were either electrospun to create novel 3D structured nanofibrous ECM (NF-ECM) or they were film casted to derive 2D surfaces of the same materials (2D controls).

1.2. Needle Free Multi-Jet Electrospinning of 3D Nanofibrous ECM (NF-ECM)

Figure 13:
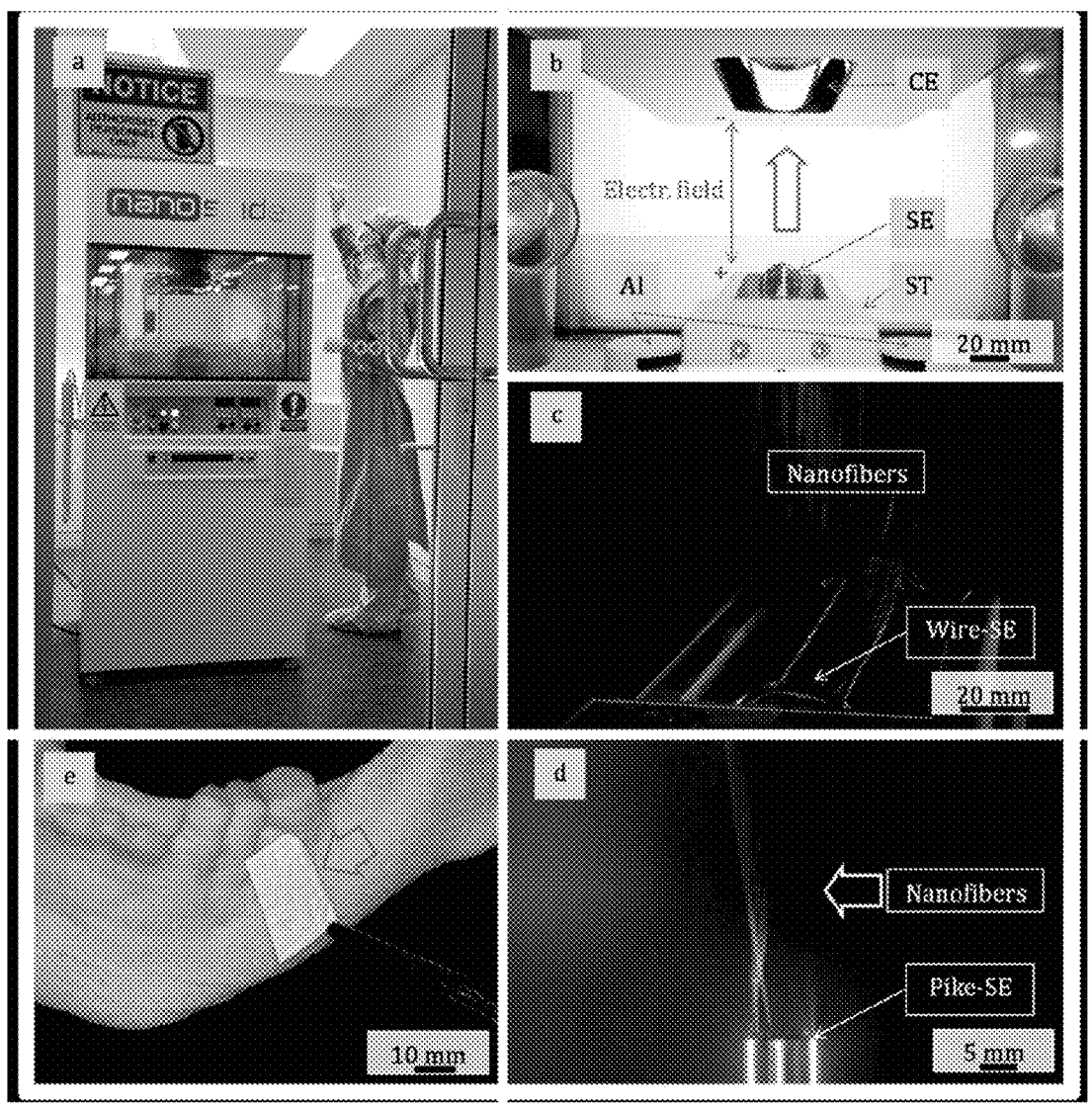
FIG. 13. Photographs showing clinical grade needle-free-electrospinning of nanofibers to prepare compositions of the present invention. a) Exhibits a setting where the NANOSPIDER™ is operating under clean room Good Manufacturing Practices (GMP)-like conditions as required for clinical grade production. b) Shows the needle-free-electrospinning set up, wire spinning electrode (SE) fitted within the solution tab (ST), and collecting electrode (CE) located 21 cm above the SE, the air inlets (AI) is also shown. c) 6-wire spinning electrode with numerous random nanofiber (NF) multi-jets used for large scale production of NF-extra cellular matrix (ECM) membranes. d) Presents the pike electrode, used to test the electrospinning parameters. e) Illustrates the structural morphology of a NF-ECM membrane (arrow) fabricated of PLGA next to a model of a human mandible as it could probably be used for HMSC delivery in periodontal regenerative therapies.

A novel industrial device originally designed for controlled electrospinning of nanoscaled textile meshes, the NanoSpider NS200 (Elmarco, Liberec, Czech Republic) was prepared to fabricate our 3D NF-ECMs from biopolymers. FIG. 13a shows the NANOSPIDER™ placed in a positively pressured, ventilated clean room set to 18 deg C. The clean room conditions would provide a clinical grade and GMP compliant production environment. FIG. 13b shows the set-up of this free surface needle-free-electrospinning device that allows for a multi jet spray of nanofibers (FIG. 13c). The polymer solutions were initially electrospun using the pike spinning electrode (SE) (FIG. 13d). The pike SE was used to test the ability of the solution to be electrospun in a random 3D architecture and to optimize the processing parameters. The tip of the pike electrode consists of a conical opening where 40 µl of the polymer solution was placed. The NANOSPIDER™ chamber was then shut and locked, where the negatively-pressured chamber, allows for a quick evaporation and evacuation of the solvent. Different processing parameters such as applied voltage and the distance between the electrodes as well as the polymer solution concentration was changed and optimized to fabricate nanofibers with similar fiber diameters. The distance between the spinning electrode and the collecting electrode was at 210 mm. The applied voltage was changed from 20-35 kV to obtain nanofibers with similar diameter across all polymers. Electrospinning was carried out long enough to fabricate NF-ECMs that formed macroscopically mesh membranes with thicknesses of 20±4 µm.

The nanofibers were characterized using a scanning electron microscope (SEM). The SEM images taken from the NF-ECM were analyzed using ImageJ (U.S. National Institute of Mental Health, Bethesda, Md., USA) for their morphology, nanofiber diameter and the packing density. The diameter of 30 fibers was measured to calculate the average fiber diameter. To calculate the uniformity (the deviation in fiber diameter) 120 fibers in random were measured and the standard deviation was calculated and divided by their average and was expressed as percentage. Packing density was presented as a percentage and was calculated by counting the number of the fibers across the images multiplied with their average fiber diameter, and then was divided by the length of the image which was 117 µm. See Example 10 below.

1.3. Film Casting for 2D Controls

The same biopolymers used to derive 3D NF-ECMs were additionally casted into flat 2D films without nanofibrous architectures. All films were prepared by directly pouring the polymer solution on a glass surface and placed on a shaker to ensure an even spreading of the solution. A similar condition compared to the clean room environment was provided. The film was allowed to air dry for 24 hours before storage in a desiccator at room temperature. The polymer films acted as controls in providing a 2D surface for HMSC colonization.

1.4. Clinically Approved Collagen Membrane (CCM) as Control

BIOGIDE® membranes (Geistlich Biomaterials, Wolhusen, Switzerland) were further controls (CCM). CCM is a 3D microfibrous type I collagen membrane derived from porcine ECM and manufactured under clinical grade conditions. As these membranes are clinically approved and commercially available for the use in oral implantology or periodontology and due to their 3D and microfibrous structure, CCM was chosen as baseline controls for our 3D NF-ECMs. CCM was purchased as 30×40 mm membranes in sterile clinical packages.

1.5. Nanofiber Cross-Linking

Pure collagen and pure gelatin NF-ECMs and films as well as all copolymer NF-ECMs containing collagen or gelatin were cross-linked immediately after fabrication using 1-Ethyl-3-(3-dimethylaminopropyl)-carbodiimide (EDC) (ThermoFisher, Victoria, Australia) and N-hydroxysulfosuccinimide (Sulfo-NHS) (ThermoFisher, Victoria, Australia) cross-linking reagents. To ensure complete cross-linking of the gelatin and collagen, EDC and NHS were added at NHS/EDC molar ratio of 0.2. Membranes were cross-linked at room temperature with shaking for 24 hours.

1.6. Mechanical Testing

Mechanical testing was carried out to assess the biophysical properties of NF-ECMs, films and CCMs. A single column tabletop universal testing system (Instron, Vic, Australia) equipped with a 50 N loading cell was used to measure the Young's modulus, the maximum tensile stress and strain of NF-ECMs, films and CCMs. NF-ECMs, films and CCMs were cut into 10×40 mm samples. Gauge opening was set to 20 mm. Depending on the maximum tensile stress, the speed of the measurement was set at 2 mm·hr$^{-1}$ or 20 mm·hr$^{-1}$ for samples having <100% maximum strain and <1000% maximum strain respectively. Sample thickness was measured using a micrometer (Mitutoyo, Kanagawa, Japan). Overall, measurements were repeated 5 times and analyzed using the BLUEHILL® software (Instron, Victoria, Australia).

1.7. Water Contact Angle

Water contact angle was determined using a goniometer (Future Digital Scientific Corp, NY, USA) to assess hydrophobicity of NF-ECMs, 2D films and CCMs. The NF-ECMs, films and CCMs were cut into 15×15 mm samples and fixed on glass slides. Overall, 3 repeats were used for each sample.

1.8. Fourier Transform Infrared Spectroscopy (FTIR)

FTIR spectra of the collagen, gelatin and the combination NF-ECMs and their polymer powder, cross-linked and non-cross-linked, and CCM were recorded on a FTIR spectrometer (Bruker Optic, Baden-Wurtemberg, Germany) and analyzed using OPUS 6.5 software (Bruker Optic, Baden-Wurtmberg, Germany). The fingerprint regions of tested polymer was analyzed and used to specifically characterize gelatin and collagen polymers within membranes.

1.9. SDS-PAGE

The following samples were used: pure collagen powder, cross-linked and non-cross-linked collagen NF-ECMs fabricated using needle-free-electrospinning and needle-electrospinning, HFIP-dissolved collagen (dissolved in HFIP for 60 minutes, but not electrospun), pure gelatin powder, HFIP-dissolved gelatin, gelatin NF-ECM and gelatin NF-ECM cross-linked. Samples were dissolved in 0.5 M acetic acid to a final concentration of 1 mg·ml$^{-1}$. A series of the samples were digested for 20 minutes in 0.1 mg·ml$^{-1}$ pepsin in 0.5 M acetic acid. The solutions were centrifuged for 15 minutes at 13330 g at 4 deg C., and the supernatants were loaded into 3-15% 10-well gel (Bio-Rad, CA, USA). 100 V was supplied with POWERPAC™ HC power supply (Bio-Rad, CA, USA) to the gel and was allowed to run for 2 hours. Protein bands were visualized using SIMPLYBLUE™ safestain (Invitrogen, NY, USA) and the images were taken using a D5100 digital camera (Nikon, Thailand). It was not possible to obtain a SDS-PAGE analysis of CCM as it did not dissolve in 0.5 M acetic acid, nor was digested with pepsin.

1.10. Isolation, Cultivation and Characterization of Human Mesenchymal Stem Cells (HMSCs) From Bone Marrow For assessment of biological properties of the tested NF-ECMs, films, cover-glass and CCMs, HMSCs were harvested from human bone marrow of a 21 year-old man. The study was approved by the ethics committees of Bond University (Queensland, Australia, Ethics approval number RO1333) and of the Medical Faculty of Christian-Albrechts-University of Kiel (Kiel, Germany, Ethics approval number AZ402/07). The isolation and culture of the HMSCs were conducted. Multiparameter flow cytometry and in vitro differentiation assays were used to characterize these cells.

1.11. Membrane Preparation and Sterilization

NF-ECMs, control films and CCMs were cut into 15×15 mm samples and mounted on CellCrown24 (Scaffdex Oy, Pirkanama, Finland) and then placed into 24-well plates. The cover-glass controls (ThermoFisher, Victoria, Australia) were also placed into 24-well plates. The mounted samples and the cover-glass controls were sterilized by 25 kGy gamma irradiation.

Briefly, NF-ECMs, films, cover-glass and CCMs were rinsed with 1 ml PBS and then immersed with αMEM overnight at 37° C. A total of 1×10$^4$ (passage 3) HMSCs in 50 μl complete medium (αMEM, 10% FCS, 1% P/S, 2.2 g/l sodium bicarbonate) were pipetted onto each membrane/NF-ECM, film, cover-glass or CCM. The cells were left to adhere for 30 minutes and then supplemented with 1 ml fresh complete medium and incubated (humidified incubator at 5% $CO_2$, 37° C.) until required.

1.12. Biocompatibility of Membranes (WST-1 Assay)

The proliferation of HMSCs seeded on NF-ECMs, films, cover-glass and CCMs was used as a measure for cytobiocompatibility and was assessed by WST-1 reagent (Roche Diagnosis, Mannheim, Germany). WST-1 is a quantitative colorimetric technique for assessment of cell proliferation and cell viability. Cleavage of tetrazolium salt by mitochondrial dehydrogenases in viable cells yield formazan, the absorbance of which can be detected at 460 nm.

Six repeats of each NF-ECM were analyzed on days 2, 5 and 8 post-seeding. On the day of test, the old medium was replaced with 1 ml of fresh HMSCs medium containing 10% WST-1 and incubated for 90 minutes. 100 μl of medium was then transferred to a 96-well plate and absorbance at 460 nm was measured on a spectrophotometer (Turner Biosystems, CA, USA). Respective films and cover-glass were used as controls while the 3D microfibrous occlusive clinically-approved collagen membrane BIO-GIDE® (CCM) was used as a control relevant to clinical medicine.

1.13. Osteogenic Biofunctional Test

To evaluate if HMSCs could be differentiated after full integration into matrices an osteogenic biofunctional differentiation test was performed. HMSCs were cultured overnight at 2×10$^4$ cells on NF-ECMs, films, cover-glass controls or CCM in six repeats. Cells were maintained for 14 days in complete medium (control) or supplemented with osteogenic media (10 mM β-glycerophosphate, 50 mg·l$^{-1}$ ascorbic acid, and 100 nM dexanethasone). Cells were then stained by alizarin red or for alkaline phosphatase.

1.14. Alizarin Red and Alkaline Phosphatase Stains

Samples were briefly rinsed with PBS, fixed with 3.7% paraformaldehyde at room temperature for 10 minutes and then washed with distilled water. Calcium mineralization was assessed using alizarin Red (Sigma, Mo., USA) by staining for 5 minutes at a concentration of 20 μg·ml$^{-1}$. Excess Alizarin red was removed by multiple washes. ALP activity was measured using SIGMA FAST BCIP/NBT tablets (5-Bromo-4-chloro-4-3-indolyl phosphate/Nitro blue tetrazolium) (Sigma, Mo., USA). The BCIP/NBT working solution was prepared by diluting 1 tablet in 10 ml of distilled water. 1 ml of working solution was added to each well and was allowed to stain in dark. Staining was stopped immediately after purple/blue color appeared on a sample. To assess for background staining, acellular membranes were also stained with Alizarin/ALP in non-osteogenic and osteogenic conditions. The samples were then rinsed with distilled water and photographed using a D5100 digital camera (Nikon, Thailand). Using ImageJ (U.S. National Institute of Mental Health, Bethesda, Md., USA), stained wells were cut at the outermost diameter of the wells and loaded mounted side by side in a common file as used in FIG. 18.

1.15. SEM Examination

Cells were seeded as per biocompatibility assays. On days 2 and 8 post-seeding, the HMSCs on NF-ECMs, films, coverglass and CCMs were fixed with 3% glutaraldehyde in PBS solution for 30 minutes, sequentially dehydrated in 30, 50, 70, 90 and 100% ethanol in PBS for 10 minutes, and then rinsed twice with hexamethyldisilazane to complete dehydration. All samples were coated using a sputter gold-coater (Jeol, Tokyo, Japan) and examined using a Neoscope scanning electron microscope (Jeol, Tokyo, Japan).

1.16. Confocal Microscopy

Cells were prepared as per biocompatibility assays. The HMSCs seeded on NF-ECMs, films, cover-glass and CCMs were fixed with 3.7% paraformaldehyde in PBS solution for 10 minutes on days 2 post-seeding. Samples were permeabilized with 0.1% Triton X-100 (Sigma, Mo., USA) in PBS solution, blocked using 3% BSA in PBS solution and incubated for 60 minutes with Hoechst 33342 (Invitrogen, NY, USA) and 1/400 rhodamine phalloidin (Invitrogen, NY, USA). Images were taken with a Nikon C1 Confocal microscope (Nikon, Tokyo, Japan).

1.17. Statistics

The data collected from the WST-1 tests and the mechanical testing were assessed for significant differences by Student's t-test and confirmed by LSD Post Hoc analysis (SPSS statistics version 19, IBM). The statistical significance was presented as, *: $p<0.05$, : $p<0.01$, *: $p<0.001$. Error bars show the standard error of the mean.

2. RESULTS 2.1 Nanofibrous Membrane Characterization

Figure 14:
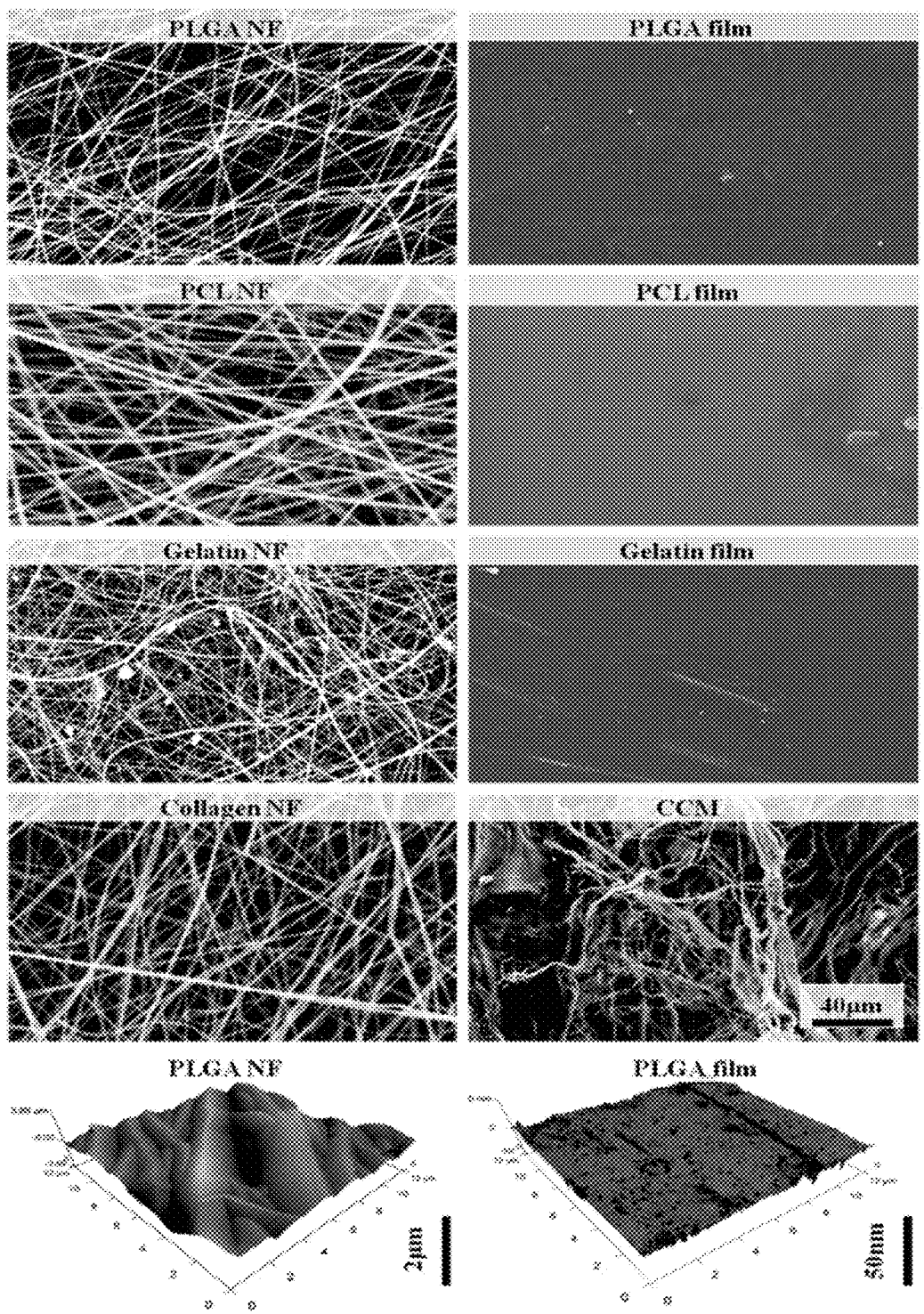
FIG. 14. Morphology of the NF-ECM membranes and film. NF-ECM were produced by clinical grade electrospinning Scanning electron microscope (SEM) images of membranes prepared by free-surface-electrospinning and film casting: PLGA, PCL, gelatin and collagen NF-ECM (NF) and films at ×4000 magnification. SEM images of collagen NF-ECM (preparation of a stable collagen film was not possible) and clinically-approved collagen membrane (CCM) is also shown. The horizontal 40 µm scale bar applied to all SEM images. Atomic force microscope (AFM) images of PLGA NF-ECM and film are shown as examples to demonstrate different surface topographies between the NF-ECMs and films. The AFM images were taken in a 12×12 µm area. The scale bar set at the AFM images present the depth of each membrane, 2 µm and 50 nm for PLGA NF-ECM and PLGA film respectively.

FIG. 14 shows the SEM micrographs of NF-ECM, films and CCM. The needle-free multi jet electrospinning method utilizing the NANOSPIDER® device was capable to produce nanofiber network membranes in a clinical grade GMP-like set-up. All NF-ECM were mesh-like in appearance with several layers of nanofibers in a random 3D architecture forming open structured accessible nanowebs with plentiful niche-like spaces. Several NF-ECM provided niche-like spaces with accurate sizes for full cellular integration or "enclosed" (compare FIGS. 19 and 20).

The average fiber diameter, the deviation in fiber diameter and the packing density were by measured using SEM images (see the table in Example 10). Among the pure NF-ECMs, PLGA NF-ECM had the thickest fibers 448±81 nm, followed by collagen 424±78 nm, gelatin NF-ECM 388±97 and the PCL NF-ECMs had the thinnest fibers with average diameter of 354±56 nm. Copolymer NF-ECMs had various diameters with no specific trend. The deviation in fiber diameter of NF-ECMs was not greater than 30% deviation in fiber diameter for any particular NF-ECM. Amongst pure NF-ECMs, PCL NF-ECM held the highest packing density (51.9±8.1%) followed by gelatin NF-ECM (35.3±15.8%), then PLGA and collagen NF-ECMs (17.3±3.1% and 14.0±10.6% respectively). Copolymer NF-ECMs had mixed packing density.

The films provided 2D surfaces which appeared to be nonporous and fiber-free on SEM unlike niche-like spaces as seen in NF-ECMs (FIG. 14). The CCM appeared microfibrous in its character with a wide range of fiber diameters that regularly exceeded the nanoscale. The fibers were tight and formed a more occlusive pattern (FIG. 14).

AFM images (FIG. 14) of PLGA NF-ECM and PLGA film are shown as examples of differences in surface topography. PLGA NF-ECM was 3D in structure with a depth of 4 µm while PLGA film exhibited no specific surface topography, with less than 50 nm depth.

Figure 15:
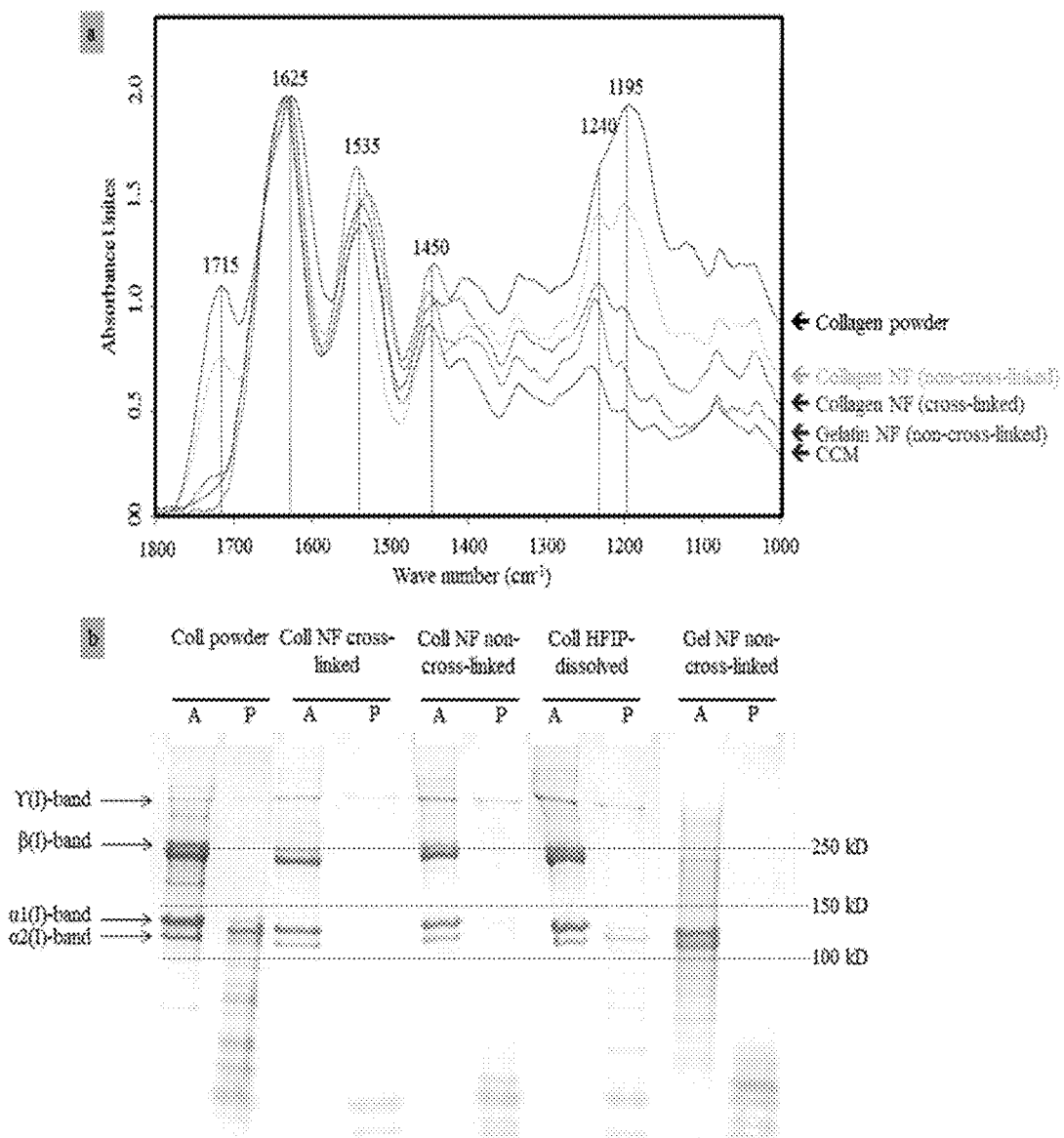
FIG. 15. Stability of collagen during electrospinning a) Fourier Transform Infrared (FTIR) of collagen (coll) powder (unprocessed) exhibiting a spectrum identical to non-cross-linked collagen NF-ECM (NF), showing the characteristics of stable secondary collagen structure (labeled peaks). These also possessed a 1450:1240 $cm^{-1}$ ratio of greater than unity. Cross-linked collagen NF had a lower peak at 1715 and a 1450:1240 $cm^{-1}$ ratio less than unity. Gelatin (gel) NF and CCM had identical spectra lacking the 1715 $cm^{-1}$ and 1450:1240 $cm^{-1}$ ratio also less than unity. b) SDS-PAGE analysis of acid-solubilized "A" and pepsin-digested "P" collagen and gelatin powder or NF-ECMs. Horizontal lines are indicative of molecular weight and arrows highlight specific collagen bands. In all samples, apart from collagen powder (unprocessed), these bands were almost completely digested by pepsin. Note: gelatin NF (non-cross-linked) is also a representative of gelatin NF (cross-linked) and unprocessed gelatin powder as the results obtained across all these samples were identical for FTIR and SDS-PAGE. (SDS-PAGE) of CCM was not possible as it was not soluble in an acidic solution.

FIG. 15a shows FTIR spectra of collagen powder and gelatin in NF-ECMs. Collagen NF-ECMs exhibited a parallel FTIR spectra fingerprint to pure collagen powder, with major peaks at 1715 cm$^{-1}$, 1625 cm$^{-1}$, 1450 cm$^{-1}$, 1240 cm$^{-1}$ and 1195 cm$^{-1}$. Collagen NF-ECM cross-linked, had a significantly lower peak at 1715 cm$^{-1}$, compared to non-cross-linked collagen NF-ECM and collagen powder. Gelatin NF-ECM and CCM lacked the peak at 1715 cm$^{-1}$. Gelatin NF-ECM cross-linked, gelatin NF-ECM non-cross-linked and gelatin powder had identical spectrum to each other. FTIR spectra of pure collagen powder and collagen NF-ECM showed a high ratio of the peak at 1240 cm$^{-1}$ compared to the peak at 1450 cm$^{-1}$, this was not seen in gelatin and CCM nor cross-linked collagen NF-ECM. This high ratio was also seen in collagen:PLGA and collagen:PCL copolymer NF-ECMs.

The results obtained from SDS-PAGE analysis are shown in FIG. 15b. Collagen powder, collagen powder dissolved in HFIP, collagen NF-ECM and collagen NF-ECM cross-linked dissolved in 0.5 M acetic acid, all exhibited γ(I)-, β(I)-, α1(I)- and α2(I)-bands. After pepsin digestion, α1(I)- and α2(I)-bands were completely digested in collagen NF-ECM cross-linked and non-cross-linked. These bands were vaguely visible in HFIP-dissolved collagen. The gelatin did not express any γ(I)-, β(I)-bands in 0.5 M acetic acid solution, and α1(I)- and α2(I)-bands were completely digested once pepsin was added.

Figure 16:
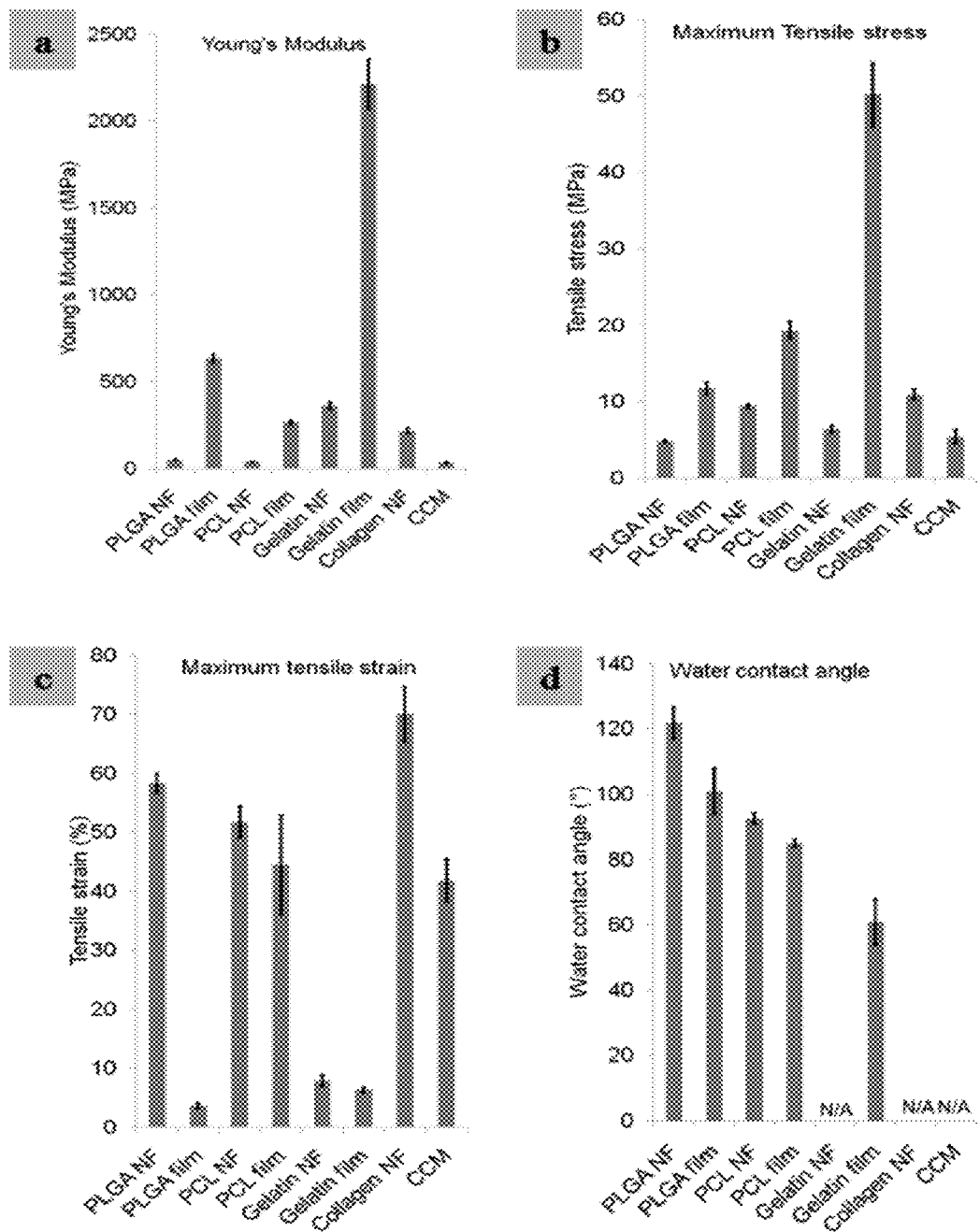
FIG. 16. Mechanical properties and water contact angle of the membranes. Clinical grade-like PLGA, PCL, gelatin and collagen NF-ECM membranes (NF) and films, as well as the clinically approved collagen membrane (CCM) were characterized for their: a) stiffness (Young's modulus), b) maximum tensile stress, c) maximum tensile strain and, d) the water contact angle. Due to the swift dispersion of water droplet within gelatin and collagen NF-ECM and CCM, the measurement of the water contact angle was impossible.

The Young's modulus and the maximum tensile stress was higher in film than NF-ECM ($p<0.001$) (FIG. 16). Gelatin film had the highest tensile stress and Young's modulus, 50.1±4.1 MPa and 2213±143 MPa respectively (FIGS. 16 (a) and (b)). Gelatin and PLGA NF-ECM had similar tensile stress (6.37±0.46 and 4.79±0.28 MPa respectively) to CCM (5.40±0.16 MPa), however collagen and PCL NF-ECMs had significantly higher tensile stress ($p<0.01$), 10.89±0.91 MPa and 9.40±0.27 MPa respectively. In contrast, the Young's modulus of the electrospun gelatin (2212±143 MPa) was almost 50 times greater than CCM (34.8±2.3 MPa) ($p<0.001$), whereas collagen NF-ECM had a slightly higher (217.92±15.30 MPa) Young's modulus. The PLGA and PCL NF-ECMs had a similar Young's modulus (51.4±1.80 and 38.5±3.30 MPa) to CCM. The maximum tensile strain was significantly higher in PLGA NF-ECM (58.3±1.60%) compared to PLGA film (3.65±0.43%), however the same trend was not seen for PCL and gelatin ($p<0.001$). The PLGA, PCL and collagen NF-ECM had a slightly higher tensile strain (58.3±1.60%, 51.7±2.70% and 70.05±4.64%) than CCM (41.8±3.58%), $p<0.001$, $p<0.05$ and $p<0.001$ respectively. However gelatin (7.83±1.01%) had a significantly lower tensile strain compared to CCM ($p<0.001$).

NF-ECMs had significantly lower contact angle (less hydrophobic) than film ($p<0.001$, FIG. 16 (d)). PLGA NF-ECMs had the highest contact angle (121°) followed by PCL NF-ECM (92°). Similar trends were seen for the films where PLGA, PCL and gelatin film had water contact angles of 100°, 85° and 60° respectively. The measurement of the contact angle for the CCM, gelatin NF-ECM and collagen NF-ECM were unattainable. These samples were extremely hydrophilic and the water was instantly dispersed through them before the measurements could be taken.

2.2 Characterization of HMSCs

HMSCs were characterized pre-seeding and were positive for CD105, CD73, CD29 and CD90 and negative for CD45, CD34, CD14, CD19, HLA-DR and 7-AAD.

2.3 Biocompatibility Assays

Figure 17:
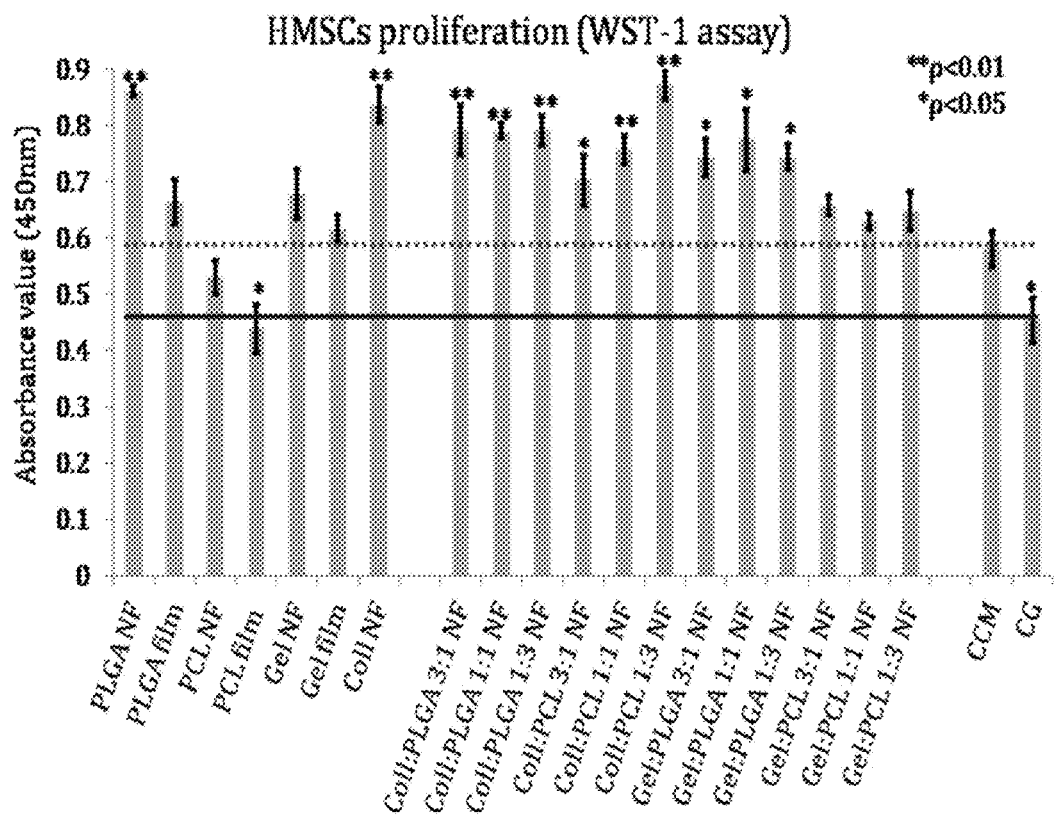
FIG. 17. Biocompatibility of membranes day 8. Proliferation of HMSCs as a measure of biocompatibility was investigated using WST-1. Various NF-ECMs (NFs) and films were tested and compared. Statistical probabilities are as indicated and based on comparing to clinically approved collagen membrane (CCM; horizontal dotted line). Cover-glass (CG) as an additional control (horizontal solid line). Error bars show standard error of the mean.

All NF-ECMS supported HMSC growth over 8 days (FIG. 17). PLGA, and collagen NF-ECMs, and all copolymers of PLGA and collagen (Collagen:PLGA 3:1, 1:1 and 1:3) and 1:3 collagen:PCL all supported higher proliferation rates as measured by absorbance at 460 nm (0.84±0.02, 0.84±0.08, 0.79±0.10, 0.79±0.03, 0.79±0.07 and 0.87±0.70 Au respectively) than CCM (0.58±0.08 Au) ($p<0.01$). In contrast, Gelatin film (0.62±0.2 Au), gelatin NF-ECM (0.67±0.4 Au), PCL NF-ECM (0.53±0.08 Au) and all gelatin:PCL copolymer NF-ECMs showed similar proliferation to CCM ($p>0.05$), while PCL film (0.44±0.10 Au) and cover-glass (0.45±0.4 Au) showed inferior performance compared to CCM ($p<0.05$). Among the pure polymers, the proliferation rate was highest for collagen and PLGA followed by gelatin and PCL respectively. PLGA co-electrospun with either collagen or gelatin showed comparable proliferation to pure PLGA NF-ECM. In contrast, collagen and gelatin NF-ECMs greatly increased the proliferation rate when mixed with PCL. Films showed significantly poorer proliferation compared to NF-ECM of the same polymers (FIG. 17).

2.4 Calcium Mineralization and ALP Activity

Figure 18:
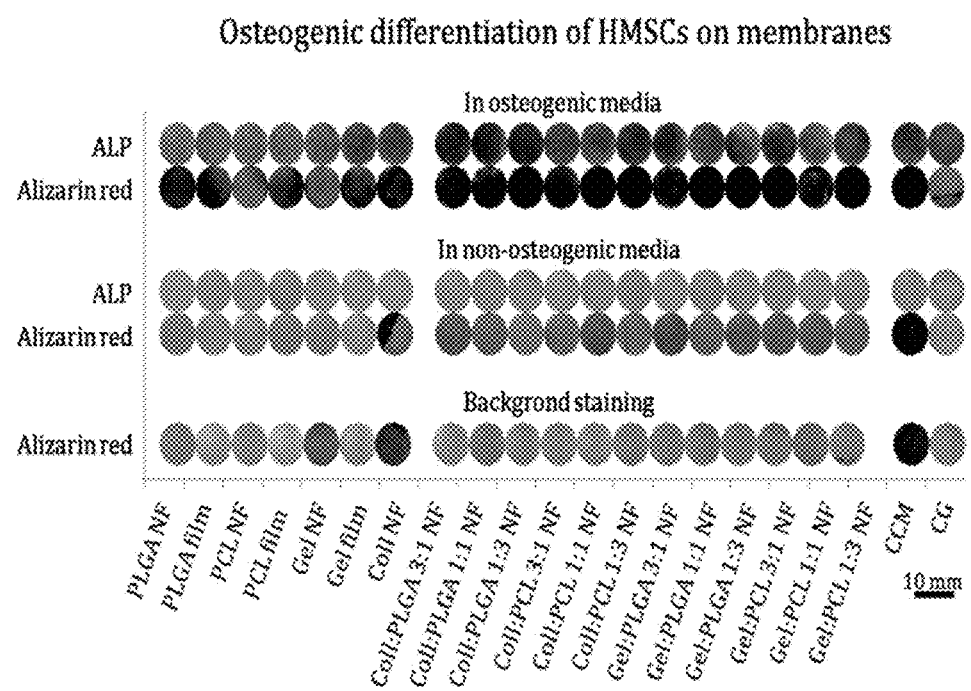
FIG. 18. Osteogenic assay of HMSCs. Assessment of calcium mineralization and ALP activity in a 24-well plate, using alizarin red (stains red for calcium deposition) and BCIP/NBT (stains purple/blue for ALP activity) for HMSCs seeded for 14 days on PLGA, PCL, collagen (coll) or gelatin (gel) NF-ECMs (NF) and copolymer NF-ECMs. The 2D films of pure polymers and the cover-glass and clinically approved collagen membrane (CCM) served as controls. Collagen NF-ECM and CCM auto-stained with Alizarin red (this was also confirmed with background staining, on samples that have not been seeded with HMSCs). However there was no autostaining of ALP for CCM and collagen NF-ECMs cultured in non-osteogenic media with or without HMSCs. The degree of purple/blue and red staining is presented as degrees of gray in the black-and-white figure.

FIG. 18 shows the extent of mineralization induced by HMSCs. NF-ECMs, films, cover-glass and CCM cultured in osteogenic media stained positive for calcium deposition (red stains) and ALP activity (purple/blue stain). All samples were positive for alizarin red and ALP in osteogenic medium. Apart from collagen NF-ECM and CCM which autostained positive form alizarin red (but negative for ALP), all samples were negative for alizarin red and ALP in control medium.

2.5 Effect of Membrane on Cell Attachment, Morphology and Integration

Figure 19:
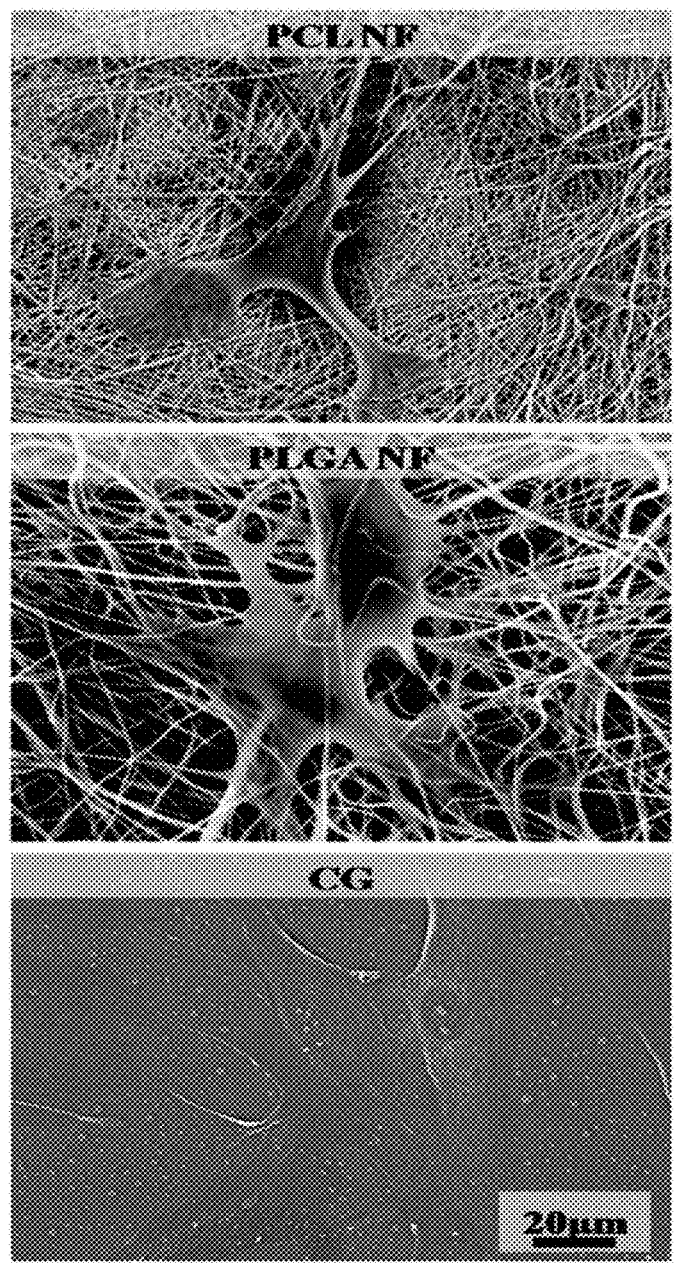
FIG. 19. Cell attachment and integration on clinical grade NF-ECM membranes (NF). SEM images of HMSCs seeded on PCL and PLGA NF-ECM membranes and cover-glass (CG) false-colored (see structures that are generally located centrally on the images). HMSCs seeded on PCL on day 2 of cell cultures, demonstrates the cell attachment and extension of filopodia on the densely packed NF-ECM membranes. HMSCs seeded on PLGA NF-ECM membranes showed the multilayered cell integration into niche-like spaces provided by the subcellularly scaled nanofiber meshes. This integration was so profound that the junction between the integrated cell and the nanofibers was indistinguishable at many points. Cells appeared to be "enclosed" inside the meshwork. HMSCs seeded on cover-glass demonstrate an almost completely flat morphology with little 3D shape as expected on a 2D structure (SEM: Virtual staining of HMSC on materials by PHOTOSHOP SC5.1.×1000 magnification).
Figure 20:
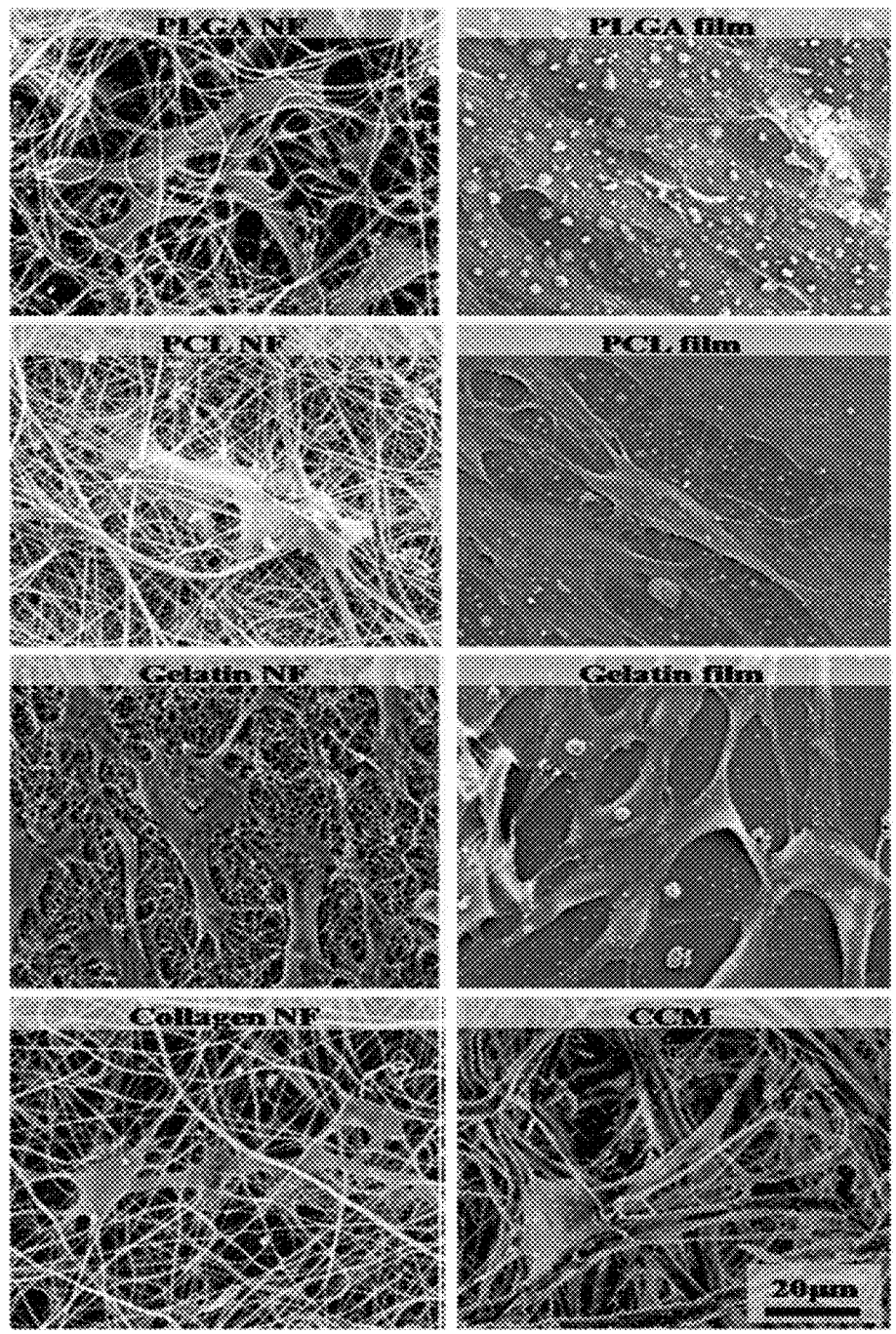
FIG. 20. Morphology of HMSCs seeded on pure membranes. NF-ECM were produced by clinical grade electrospinning SEM images of HMSCs after 2 days of culture on PLGA, PCL, gelatin and collagen nanofibrous 3D ECM (NF) and their 2D film counterparts. The NF-ECM showed a multifaceted enclosed-like integration of cells into the nanofiber mesh niches. Cells on film controls were flat and lacked 3D orientation. Clinically approved collagen membrane (CCM) was used as a 3D control. (×1000 magnification).
Figure 21:
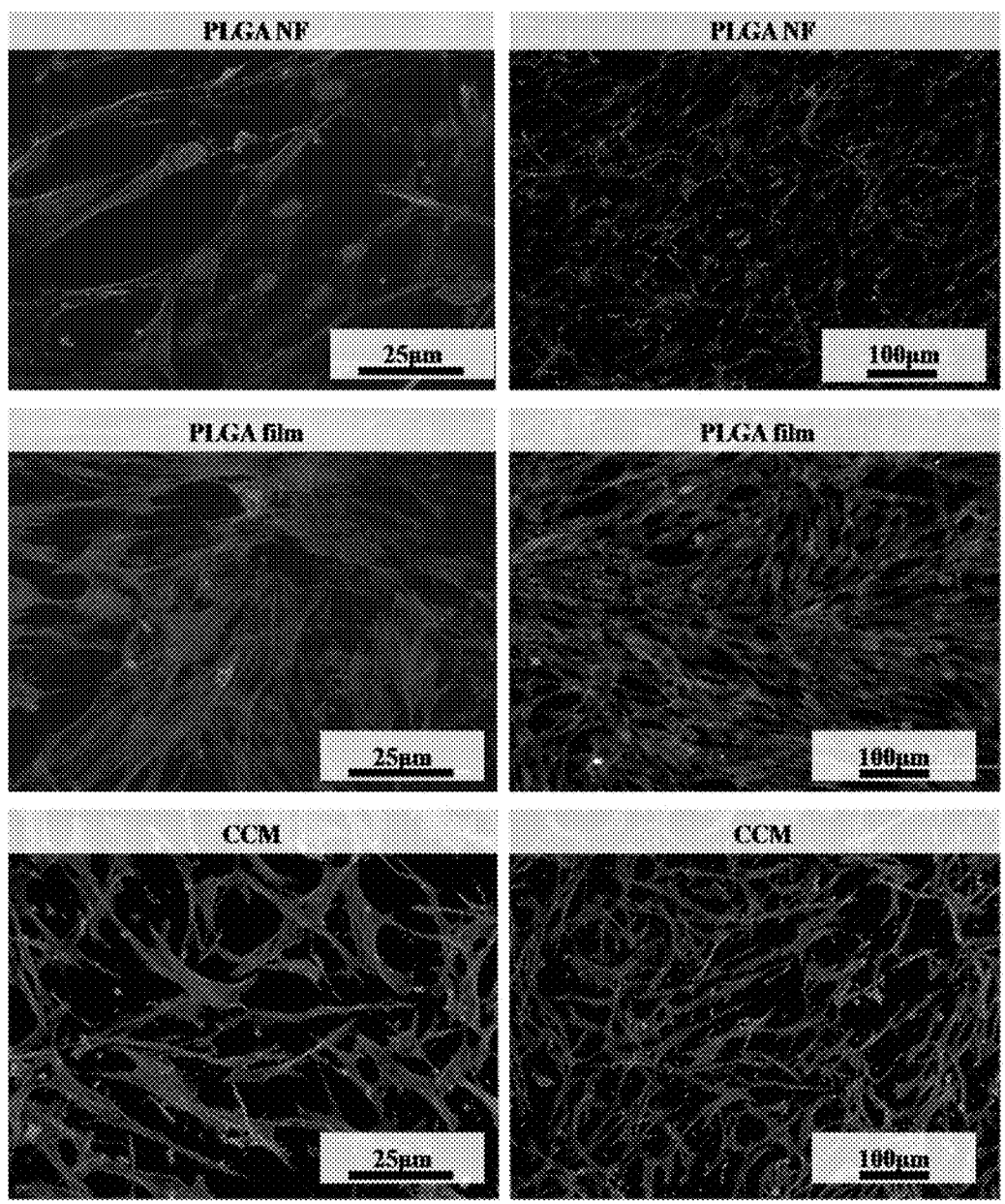
FIG. 21. Orientation and morphology of HMSCs on materials. NF-ECM were produced by clinical grade electrospinning Rhodamine-phalloidin tagged (red—colour image; gray—in black and white image) confocal images of HMSCs cultured for 2 days on PLGA NF-ECM (NF) and film, as well as HMSCs cultured on clinically approved collagen membrane (CCM). PLGA NF and CCM showed a good 3D orientation of cells. In contrast on PLGA film, cells were more spread and flat. HMSC phenotype was similar on gelatin and PCL NF/film. ×100 and ×200 magnifications.
Figure 22:
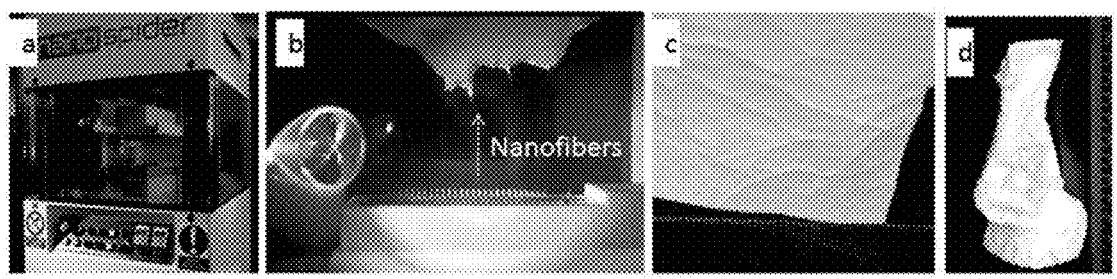
FIG. 22. Images showing a) nanospider device and b) Electrospinning set up for manufacturing face replacement out of nanofibrous matrix. The nanofibers are sprayed in an electrical field onto a 3-dimensional face mould in the individual dimension of the patient's face. c) Large scale mass production of artificial skin replacement made from nanofibrous matrix via electrospinning Large scale production may exceeds 1 square meter of nanofibrous material. d) Individual skin replacement for nose and upper lip made from nanofibrous matrix. This replacement was made in the same process such as the production of the face replacement and then contoured accordingly.
Figure 23:
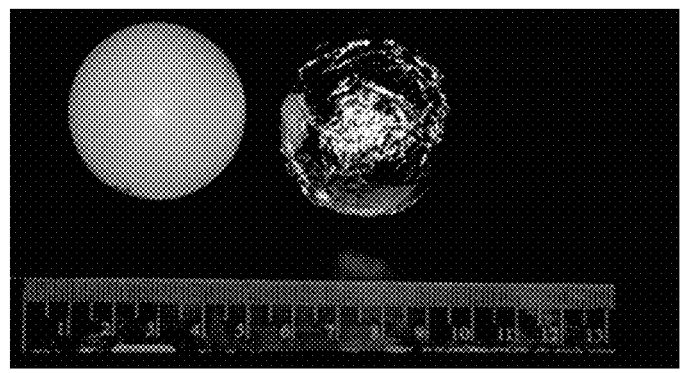
FIG. 23. Images showing an eye replacement in accordance with the electrospinning described in the above figure legend for FIG. 22. a) Eye mould with conducting surface cover. b) Nanofiber spinning process onto eye mould.
Figure 23:
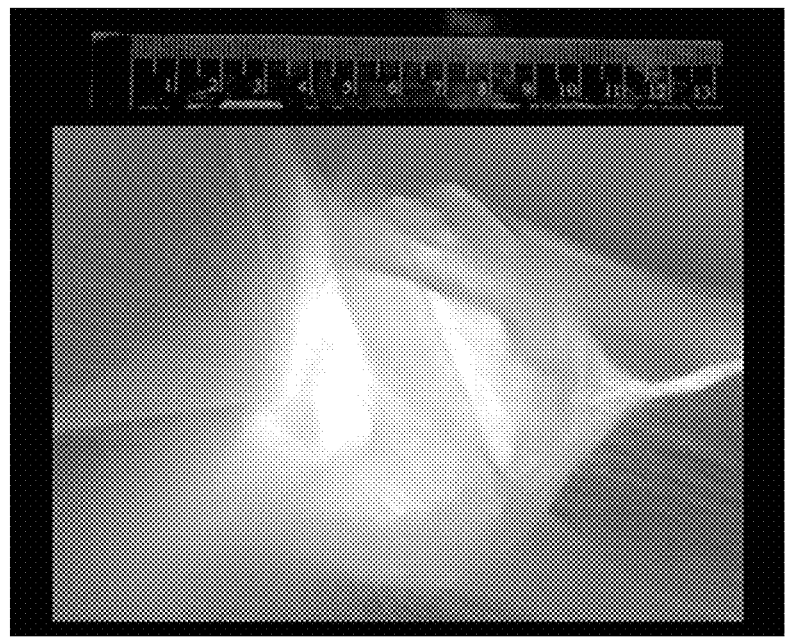
Figure 24:
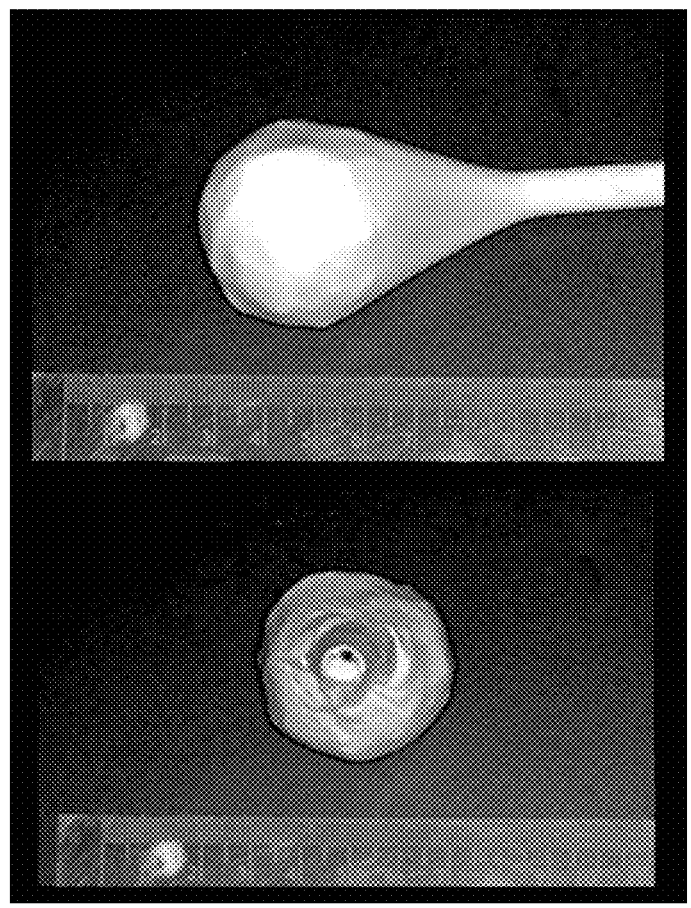
FIG. 24. Images showing three-dimensional nanofibrous eye moulds.

FIGS. 19, 20 and 21 show the morphology of HMSCs on NF-ECMs, films, cover-glass and CMM. HMSCs on cover-glass control lacked 3D depth (were very flat) and the cytoplasm were large and extended widely (very well-spread) as particularly seen on FIG. 19. Although not visible in the images, these flat HMSCs on cover-glass easily broke adherence when mechanically challenged by pipetting of cell culture media in contrast to HMSCs cultured on NF-ECMs which were near-on impossible to dislodge, even if required for RNA/protein assays. Film controls followed much the same trend as HMSCs plated on cover-glass (FIG. 20). In contrast, HMSCs on NF-ECMs visibly occupied 3D space, firmly attached and integrated well within the NF-ECM nanofiber mesh and in doing so lost the widely-spread cytoplasm. While a high-packing density seen in PCL NF-ECM minimized cell integration, for NF-ECMS with lower nanofiber packing density (such as PLGA), HMSCs fully integrated within the 3D confinements of the NF-ECM in a manner that the nanofibers and cell filopodia extensions morphed together as one, that is, the nanofiber-to-cell junction was indistinguishable (FIG. 19, middle panel). With such lack of discrepancy between cell and PLGA NF-ECM, the NF-ECM appeared to be as an "endocytoskeleton" for the HMSCs.

HMSCs cultured on CCM also exhibited integration however the matrix fibers were visibly much larger than that of nanofibrous NF-ECM. 3D confocal microscopy of HMSC cytoskeleton concurred with above results (FIG. 21).

3. CONCLUSION

3D NF-ECMs with synthetic or natural origin or their combinations were fabricated through a novel needle-free multi jet nanofiber electrospinning process in a GMP compliant setting clean room. The 3D NF-ECM fabricated using this technique exhibited uniform fibers of diameters and packing density similar to the natural ECM with outstanding biocompatibility that outperformed 2D films, cover-glass and a clinically-approved benchmark ECM scaffold. Altogether, with such proliferative potential, cell enclosed-like integrative properties, potential to act as a stem cell delivery vehicle and an ability to guide specialized differentiation of stem cells on demand, it appears that NF-ECMs fabricated using needle-free-electrospinning in this setting could be valuable in regenerative medicine.

Example 9

Drug Release Study Comparing the Composition of the Present Invention, which is in the Form of a Three-Dimensional Nanofibrous Membrane, to a Two-Dimensional Film This study shows more stable and slower release of ANTI-VEGF by the composition in the form of a three-dimensional nanofibrous membrane compared to a two-dimensional film. Anti-VEGF is commonly used in macular degeneration treatment and the administration route of choice is via injection.

ANTI-VEGF or Bevacizumab (AVASTIN™) an angiogenesis inhibitor, was integrated into PLGA film and PLGA nanofibers by direct dispersion. An aqueous solution of Bevacizumab with a final concentration of 25 mg/ml was supplemented to 6% wt/v PLGA solution in dichloromethane. The resultant solution was mixed and then sonicated for 30 seconds to ensure even dispersion of the drug throughout the polymer solution. Half of the solution was then casted into film and the other half was electrospun through needle-less-electrospinning To study the kinetic of the release of Bevacizumab the PLGA film and PLGA nanofiber compositions containing Bevacizumab were immersed in phosphate buffered saline and were incubated in 5% $CO_2$ at 37° C. The release of Bevacizumab was measured by UV-spectroscopy at wavelength of 285 nm.

Figure 12:
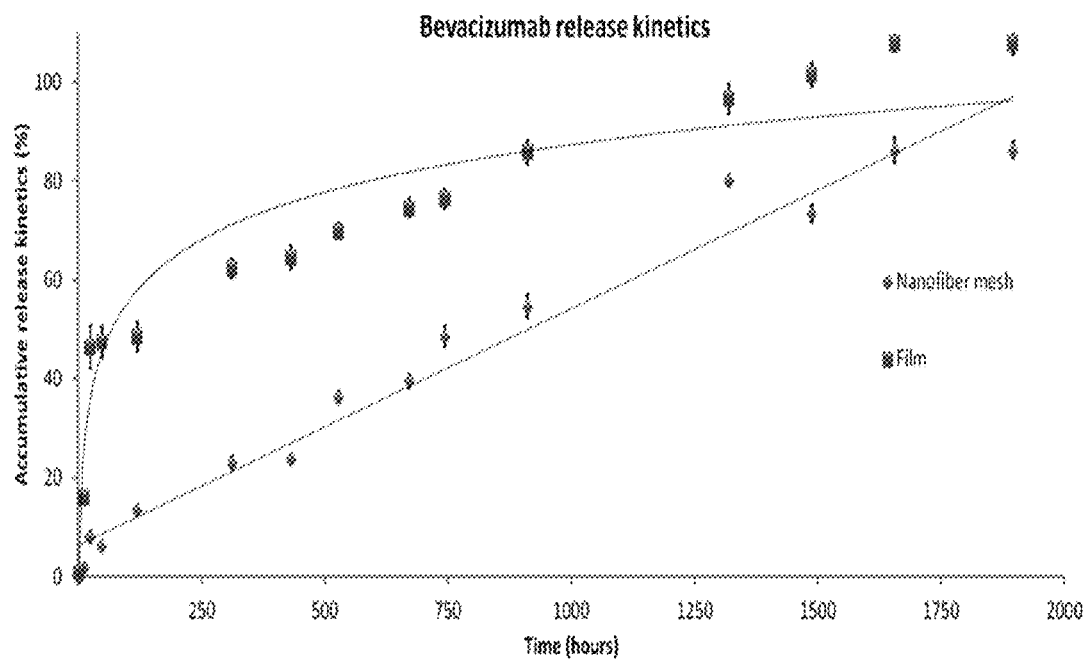
FIG. 12. Graph showing accumulative release of Bevacizumab over 79 days (1896 hours) when comparing nanofibrous mesh/membrane to film.

The results as shown in FIG. 12 show the accumulative release of Bevacizumab over 79 days (1896 hours). The film resulted in an initial burst of the drug, whereas nanofibers allowed for a linear controlled slow release of the drug over the 79 day.

Example 10

Diameter and Packing Density of Nanofibers

The average diameter of nanofibers in each NF-ECM was measured including standard deviation. The uniformity of the nanofibers is presented in the below table as percentage deviation in fiber diameter. The packing density shows the percentage concentration of the fibers across the SEM image of individual NF-ECMs.

| NF-ECM | Diameter [nm] | Deviation [%] | Packing density [%] |
|---|---|---|---|
| *Pure polymer* | | | |
| PLGA | 488 ± 81 | 18 | 17.3 ± 3.1 |
| PCL | 354 ± 56 | 16 | 51.9 ± 8.1 |
| Collagen | 388 ± 97 | 25 | 14.0 ± 10.6 |
| Gelatin | 424 ± 78 | 18 | 35.3 ± 15.8 |
| *Collagen:PLGA* | | | |
| 3:1 | 400 ± 122 | 30 | 68.2 ± 6.1 |
| 1:1 | 504 ± 76 | 15 | 47.8 ± 4.2 |
| 1:3 | 421 ± 70 | 17 | 46.4 ± 3.3 |
| *Gelatin:PLGA* | | | |
| 3:1 | 370 ± 108 | 29 | 31.7 ± 4.5 |
| 1:1 | 564 ± 92 | 16 | 40.9 ± 10.6 |
| 1:3 | 433 ± 68 | 16 | 37.9 ± 4.4 |
| *Collagen:PCL* | | | |
| 3:1 | 465 ± 129 | 28 | 51.3 ± 9.6 |
| 1:1 | 499 ± 119 | 24 | 67.7 ± 11.1 |
| 1:3 | 420 ± 51 | 12 | 62.7 ± 7.8 |
| *Gelatin: PCL* | | | |
| 3:1 | 440 ± 81 | 18 | 65.9 ± 24.2 |
| 1:1 | 396 ± 49 | 12 | 45.6 ± 9.2 |
| 1:3 | 365 ± 49 | 13 | 1.6 ± 14.1 |

Example 11

Influence of Stem Cells Once Settled into Nanofibers Matrix

This study shows that cell stimulation and differentiation factor can be released from the nanofibers and actively influences the stem cells after release. This is tested by having the differentiation factors inside the media, not inside the fibers.

A small molecule; purmorphamine, was directly integrated into poly(lactic-co-glycolic acid) (PLGA) solution and then electrospun the solution into fibers. Purmorphamine, a 2,6,9-trisubstituted purine, has been proved to enhance osteogenic differentiation. Molecular investigations showed that purmorphamine binds to the 7-transmembrane Smoothened receptor and therefore activates the Hedgehog signal pathway, which play an important role during the development of bone and the other tissues and organs.

10 mM purmorphamine stock solution was prepared by dissolving purmorphamine powder in dimethyl sulfoxide (DMSO). PLGA was dissolved through gentle stirring in a solvent mix of 70% chloroform: 30% dimethylformamide to obtain a 10% wt/v solution. Purmorphamine working solutions made in different concentrations by mixing proper purmorphamine stock solution with 10% wt/v of PLGA were utilised to electrospin the nanofibrous membranes. Controls were plain 10% wt/v PLGA with the same amount DMSO in the working solution. The electrospinning procedure was performed under 27-35 kV and the distance between the electrodes was 21 cm.

For osteogenic differentiation, the cells on the membranes were cultured in the osteogenic differentiation medium for three weeks. Osteogenic medium was made of supplemented α-MEM containing 100 nM dexamethasone, 10 mM β-glycerophosphate and 52 mg/L ascorbic acid. The hMSCs seeding procedure was as same as the proliferation assay. After 24 hours incubation to allow cell attachment the proliferation medium was completely replaced with osteogenic medium followed by 30% medium change twice a week. After 2 weeks. The resulting calcium deposits in the matrix were quantified.

Mineralization is one specific maker of bone formation. The calcium deposition in the matrix was measured to quantify the osteogenic differentiation of hMSCs. The graph below showed a significant increase in calcium deposition when 2 μM of purmorphamine was added directly added into the differentiation media on polystyrene culture plate (PS). Similar increase was also seen on pure PLGA membranes. The composites PLGA 80 and PLGA 160 (PLGA membrane integrated with 80 μM and 160 μM of purmorphamine) also showed an improvement in calcium deposition in comparison to pure PLGA. These results showed that purmorphamine can enhance osteogenic differentiation and the integration of purmorphamine with the PLGA membrane resulted in a successful release of this drug resulting in an improved osteogenic differentiation.

Figure 31:
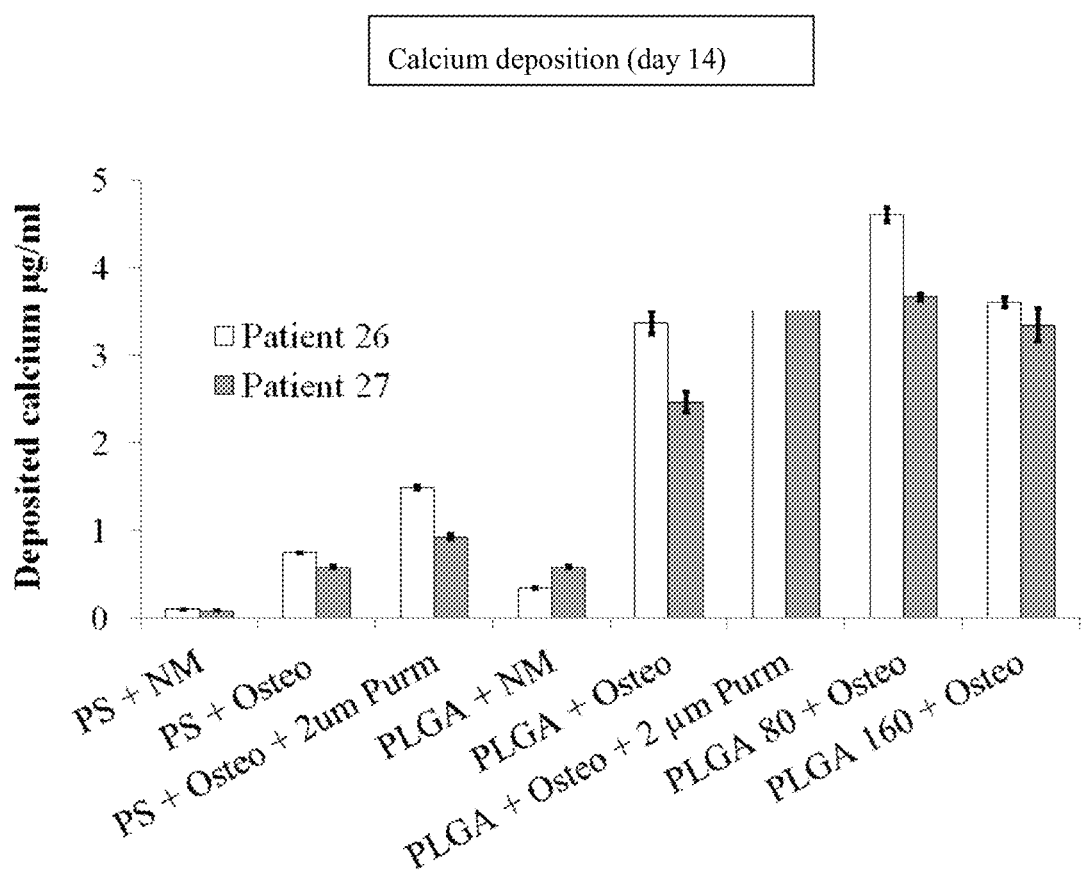
FIG. 31. Graph showing calcium deposition at day 14 for pure PLGA, PLGA with 80 µM of purmorphamine (PLGA80) and PLGA with 160 µM of purmorphamine (PLGA160).
Figure 32:
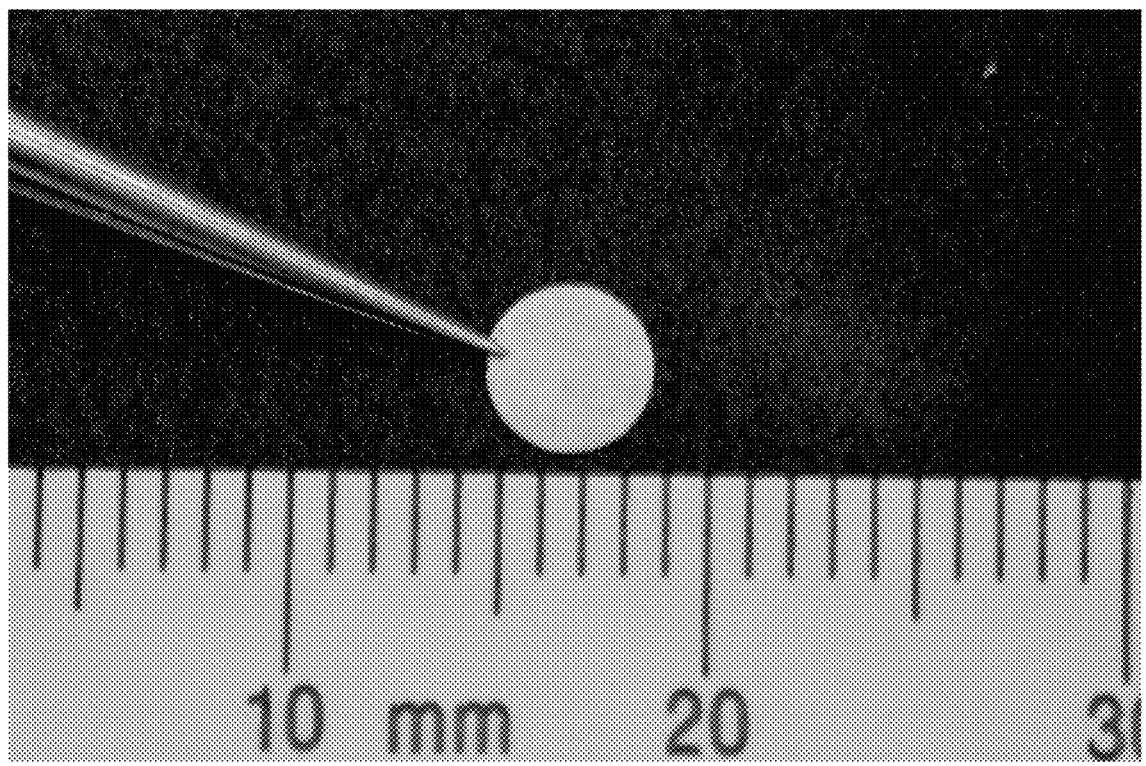
FIG. 32. Image of an ultrathin membrane as produced by the processes described herein for use in the retina, BM or any anatomical part of the back wall of the eye.

In addition, the graph in FIG. 31 demonstrated a significant increase in calcium deposition on nanofibers compared to PS, indicating the nanofibers alone can enhance the cellular differentiation of hMSCs. Furthermore, hMSCs cultured on PLGA nanofibers without being supplemented to osteogenic media also showed signs of calcium deposition within the matrix that might indicate that the surface topography of the nanofibers could also induce osteogenic differentiation.

Example 12

Studies Relating to Manufacturing of an Ultrathin Nanofibrous Membrane by a Novel Nanotechnology Process that would Mimic the Natural Three-Dimension Architecture of a the Human Bruch's Membrane (BM)

Age-related macular degeneration (AMD) is the leading cause of the blindness in the population over 50 years old in the western world [1, 2]. Cumulative age-related alteration to Bruch's membrane (BM) and the death of retinal pigment epithelium (RPE) cells are the major characteristics of AMD. The natural human BM is a 2-4-μm thick extracellular matrix (ECM) compartment connecting the RPE with the choriocapillaris and is composed of five anatomic layers from internal to external: basal lamina layer of the RPE, inner collagen layer, elastin layer, outer collagen layer and basal lamina of the choriocapillaris [see references 3, 4]. BM provides physical support for RPE cell adhesion, migration and differentiation; RPE is a monolayer of hexagonal cells playing multiple roles in visual function: absorption of stray light, isomerization of retinol in the visual cycle, phagocytosis of light damaged photoreceptors' outer segments, secretion of growth factors and formation of the blood-retina barrier together with BM to regulate the reciprocal exchange of biomolecules, nutrients, oxygen and metabolic waste products between the retina and the choroid [see reference 5]. Consequently, loss of, or damage to the RPE causes photoreceptor dysfunction and irreversible blindness.

Currently, treatments for visual restoration of atrophic AMD are severely limited [see reference 6]. Cell therapy for restoration holds promise since the replacement of the damaged RRE could probably restore retinal function. Animal models have demonstrated the curative potential of RPE replacement for AMD [see references 7-12]. Moreover, autologous RPE harvested from the midperiphery and fetal sheet transplants have shown partial vision improvement in AMD patients [see references 13-18]. Autologous transplants however are limited by the genetic predisposition to AMD and may lead to repeated retinal manifestation. Human embryonic stem cells (hESC) and induced pluripotent stem cells have been differentiated to RPE cells in vitro and thus present possible alternative cell sources for AMD therapy in the broader future [19-24]. A Phase I clinical trial to transplant dissociated hESC-derived RPE cells has been approved by Food and Drug Administration (FDA) recently [25, 26]. However, sources of fetal donor tissue will usually be limited in supply and their use may raises ethical concerns.

Although RPE transplants can delay photoreceptor dysfunction, the age-damaged BM may not provide a proper microenvironment to support transplant attachment or survival and may even inhibit RPE function. The limited survival of transplants and the formation of abnormal structures in the retina and other sites in the back wall of the eye are major challenges in AMD cell therapies [27]. Therefore many laboratories have been working on BM prosthesis to enable delivery of a long-term functionally intact RPE patch that is simultaneously protected from the influence of aged BM [13].

The ideal BM substitute should support maintenance of RPE phenotype, restore normal retinal architecture, be tolerated by the host immune and visual system, possess thickness appropriate to the subretinal space, be surgically easy to manipulate and biodegradable over time [13, 28]. As it stands, the ideal artificial scaffold to mimic the natural BM which would allow growth of an appropriate, fully functional RPE monolayer which in turn would allow subsequent implantation, has yet to be found. In most studies, smooth surfaces such as films were investigated as potential BM substitutes [27]. Recently silk membranes have been brought into the focus as a RPE delivery membrane [38]. However, it is not fully clear yet if the degradation process of many of such materials could later trigger an adverse immune response of the host which could probably increase unwanted subretinal neovascularisation, scarring of BM, immune rejection or decrease biofunctionality and longevity of the graft.

By way of contrast, the native BM contains a fine meshwork of natural proteins with nanofibrillar topographies, rather than being a smooth silky film. Thus, novel nanotechnology methods for manufacturing nanofibrillar meshes as described herein represent significant progress in allowing production of exact morphological mimicries of the native human BM. An engineered membrane mimicking the natural architecture as closely as possible could facilitate appropriate RPE monolayer engineering and thereafter delivery to the subretinal space.

In the present study, the inventor aimed to fabricate ultrathin nanofibrous membranes with a novel electrospinning process with nanofibers that could allow for the design of a close mimicry of the natural BM. Commonly used safe biopolymers collagen type I and PLGA, were electrospun into membranes. The feasibility of using such nanomembranes as a BM substitute for culture of primary RPE cells was investigated in the aim of manufacturing a nature-like artificial BM substrate for novel treatment strategies of AMD.

1. MATERIALS AND METHODS 1.1 Preparation of Nanofibrous Membranes

PLGA with a molar ratio of 85:15 L-lactide:glycolide (Purac Biochem, Netherlands) and the natural biopolymer bovine collagen type I (Cat# C3511, Sigma, USA) were dissolved in 1,1,1,3,3,3-hexafluoro-2-propanol (HFIP) (ThermoFisher, Australia) at a concentration of 10% wt/v. Sonication was performed for 30 minutes to enhance dissociation of collagen. An industrial device for textile electrospinning, the NanoSpider NS200 (Elmarco, Czech Republic), was used to fabricate the PLGA and collagen nanofibrous membranes in a clinical grade clean room set-up as described in Example 8. The polymer solutions were initially electrospun using a pike spinning electrode to allow generation of a random 3-dimensional architecture. The distance between the pike electrode and the collecting electrode was 210 mm. The applied voltage was set to 32 kV and 35 kV for PLGA and collagen respectively to obtain nanofibers with similar diameter across all fabricated membranes.

Pure collagen nanofibers were chemically cross-linked immediately after fabrication according to Kuijpers et al [46]. Briefly, N-hydroxysulfosuccinimide (Sulfo-NHS) (ThermoFisher, Australia) and 1-Ethyl-3-(3-dimethylaminopropyl)-carbodiimide (EDC) (ThermoFisher, Australia) were dissolved at a molar ratio of 1:5 in 95% ethanol and added to fabricated collagen membranes. The cross-link procedure performed at room temperature with shaking for 24 hours. For experiments, all the fabricated membranes were cut into small pieces and affixed to CellCrown24 (Scaffdex Oy, Finland) and then sterilized by 25 kG gamma irradiation.

1.2 Characterization of Electrospun Membranes

Nanofibers making up membranes were gold-sputtered and then characterized using a Neoscope JCM-5000 Jeol scanning electron microscope (SEM) (Jeol, Japan). The Marco Zarbin group [47] kindly provided the SEM image of native inner collagenous layer of a human BM to serve as a natural control (FIG. 25D). The SEM images were analyzed using the ImageJ software (National Institute of Mental Health, USA) to determine nanofiber morphology, diameter and packing density. At least 50 fibers were measured to calculate the average of fiber diameter in each membrane. Packing density is presented as a percentage and was calculated by counting the number of the fibers across each image, multiplied by the average of fiber diameter, and then divided by the width of the image (117 µm at 1000× magnification).

Mechanical testing was performed to assess the biophysical properties of fabricated membranes. A single column tabletop universal testing system (Instron, Australia) equipped with a 50 N loading cell was used to measure the Young's modulus, the maximum tensile stress and strain of specimens. Electrospun membranes were cut into 10×40 mm samples. Gauge opening was set to 20 mm. The speed of the both measurements was set at 2 mm per minute. Sample thickness was measured using a micrometer (Mitutoyo, Japan). Measurements were repeated 5 times and analyzed using the BLUEHILL® software (Instron, Australia).

1.3 Proliferation Assay

Human primary RPE cells were purchased from Lonza (Cat#00194987). The cell culture basal medium and all the supplements were purchased from Lonza (Cat#00195409). Cells were seeded on membranes at passage 3. Briefly, the sterile membranes affixed to CellCrown24 were washed with phosphate buffered saline (PBS) for 2 hours and then 10,000 cells were added to each specimen in plating medium consisting Retinal Pigment Epithelial basal medium supplemented with 2% fetal bovine serum (FBS), 0.5% fibroblast growth factor basic (FGF-B), 2% L-glutamine and 0.25% GA-100. Cells on cover glass served as smooth surface controls. The next day the medium was changed to growth media which contained all the supplements except FBS. Thereafter, the medium was changed every second day.

WST-1 reagent (water soluble tetrazolium (4-[3-(4-Iodophenyl)-2-(4-nitrophenyl)-2H-5-tetrazolio]-1,3-benzene disulfonate)] (Roche Diagnostics, Germany) was used per the standard protocol as a proliferation assay. The tetrazolium salt WST-1 is converted into formazan by mitochondrial dehydrogenases in viable cells. The formazan can then be quantitated spectrophotometrically. The WST test was performed on days 1, 3 and 5. On the test day, the old medium was replaced with 900 µl fresh growth medium. Then 100 µl WST-1 reagent was added to each sample and incubated at 37° C., 5% $CO_2$. After 4 hours, 100 μl of medium from each sample was transferred to a 96-well plate and the absorbance was measured at 450 nm by a spectrophotometer (Promega, USA). Six repeats of each specimen were analysed.

1.4 Scanning Electron Microscope (SEM) Examination

SEM examination was used to investigate cell morphology on membranes. The seeding process and medium changes were as described above. SEM samples were prepared at day 3 and 11 for examination. On the day of SEM examination, membranes with human RPE cells were fixed with 3% glutaraldehyde in PBS solution for 24 hours. They were then dehydrated by increasing concentrations of 30, 50, 70, 90 and 100% ethanol in PBS for 10 minutes each and then rinsed twice with hexamethyldisilazane. All specimens were gold-coated by a gold-coater sputter (Jeol, Japan) and images taken with a Neoscope JCM-5000 Jeol bench-top SEM (Jeol, Japan).

1.5 Immunocytochemistry

Cells were seeded on collagen and PLGA membranes affixed to CellCrown24 and on cover glass in 24-well plates at a density of 10,000 cells/cm². After 11 days of culturing, samples were fixed with 4% paraformaldehyde for 10 minutes at room temperature, permeabilized with 0.1% TritonX-100 in PBS for 5 minutes and washed with PBS. Then the samples were incubated with a 1:1000 dilution of mouse anti-RPE65 antibody (Cat#ab13826, Abcam, USA) or with a 1:100 dilution of mouse Alexa Fluor 488-conjugated-anti-ZO-1 antibody (Cat#339188, Invitrogen, Australia) in blocking buffer (3% Bovine serum albumin (Sigma) in PBS) for 90 minutes at room temperature in the dark. Cells were co-stained with a 1:1000 dilution of Hoechst 33342 (Invitrogen, Australia) in blocking buffer in order to label nuclei. Samples stained with RPE65 antibody were washed and incubated for 30 minutes at room temperature in the dark with an Alexa Fluor 488-conjugated goat anti-mouse antibody (Cat#A11001, Invitrogen, Australia). Imaging was carried out using a Nikon C1 confocal microscope (Nikon, Japan).

1.6 Statistical Analysis

Statistical significance of proliferation data was analysed by Student's t-test and set at $p<0.05$ for comparison of electrospun membranes with cover glass at each time point.

2. RESULTS 2.1 Membrane Characterization

The inventor was able to electrospin nanofibers of PLGA and collagen biopolymers with our NANOSPIDER® device. The resulting ultrathin membranes were made of nanofibers that settled in a 3D architecture and morphology similar to the genuine natural BM.

Figure 25:
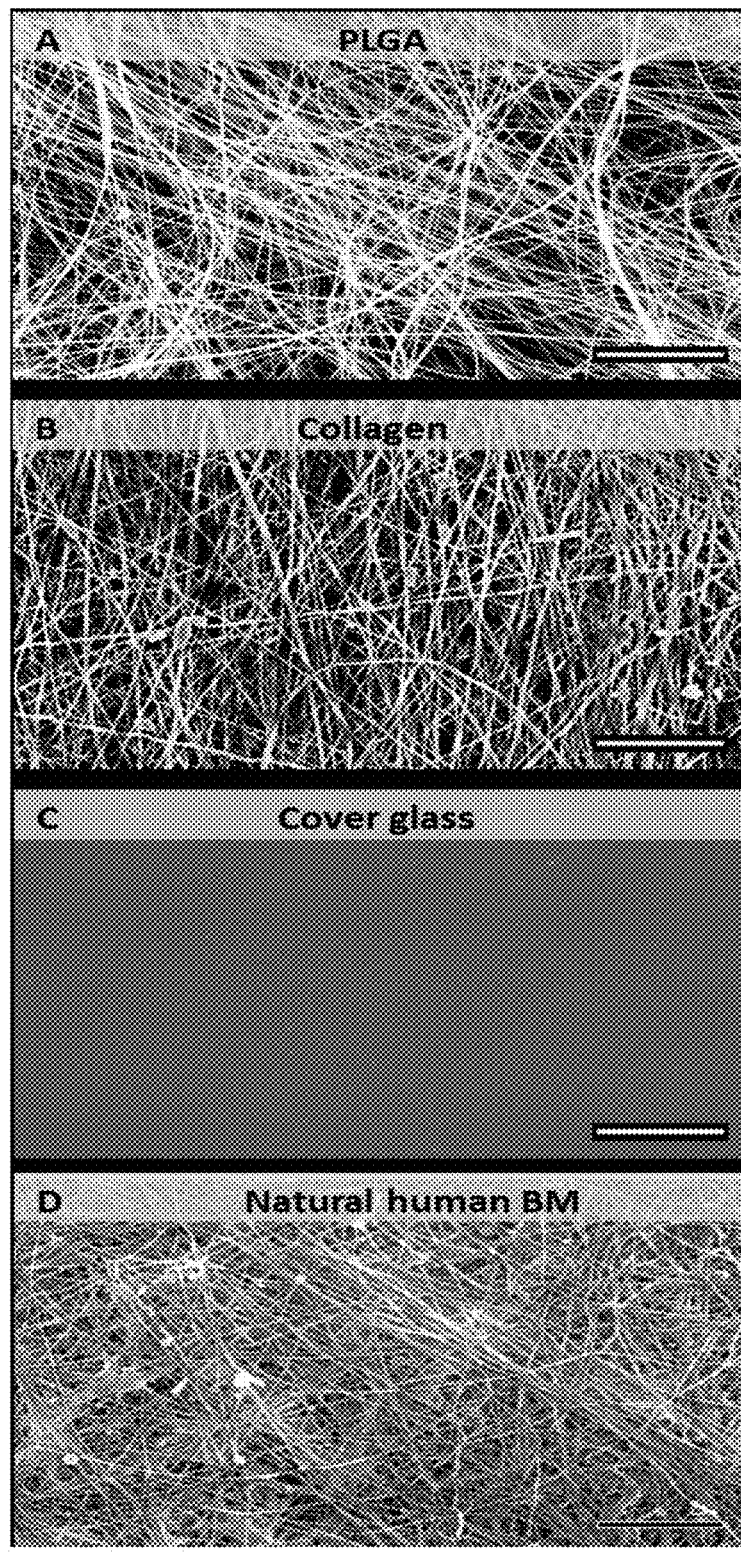
FIG. 25. SEM images of native nanofibrous membranes, cover glass and inner collagenous layer of human BM. A: PLGA nanofibrous membrane; B: Collagen nanofibrous membrane; C: Cover glass. D: Inner collagenous layer of a human BM, reprinted with permission from reference [47]. The fiber morphology and 3D architecture in the fabricated nanofibrous membranes of the invention showed high similarity to that of the inner collagenous layer of a human BM. In contrast, the cover glass showed no 3D morphology. Scale bar=20 µm.

SEM images in FIG. 25 show the topography of fabricated membranes and cover glass and native inner collagenous layer of human BM; Table in Example 10 gives the data of physical features of nanofibrous membranes. The electrospun membranes were composed of a network of randomly organized fibers. The average fiber diameter was 331±78 nm in PLGA membrane and 299±185 nm in collagen membrane, respectively. The PLGA membrane possessed a fiber packing density of 37.1±1.1%, while collagen membrane had 30.3±1.4%. The SEM images analysis showed that the native inner collagenous layer of human BM had the fiber diameter of 366±98.8 nm and packing density of 30.2±8.2%. The structure of fibers in the fabricated membranes showed similarity to that of inner collagenous layer of human BM. In comparison, the surface of cover glass was relatively smooth and homogenous. Both collagen and PLGA fabricated membranes were 14 μm thick. The maximum tensile strength of the PLGA nanofibrous membrane was 1.5±0.4 MPa with the ultimate strain of 28.8±4.9% and a Young's modulus of 131.9±13.3 MPa. The collagen nanofibrous membrane had a higher value of tensile strength, tensile strain and Young's modulus, 10.8±0.7 MPa, 70.0±4.6% and 217.9±15.3 MPa, respectively. In summary, PLGA membrane had a lower strength but possessed greater elasticity than the collagen membrane.

2.2 Proliferation Assay

Figure 26:
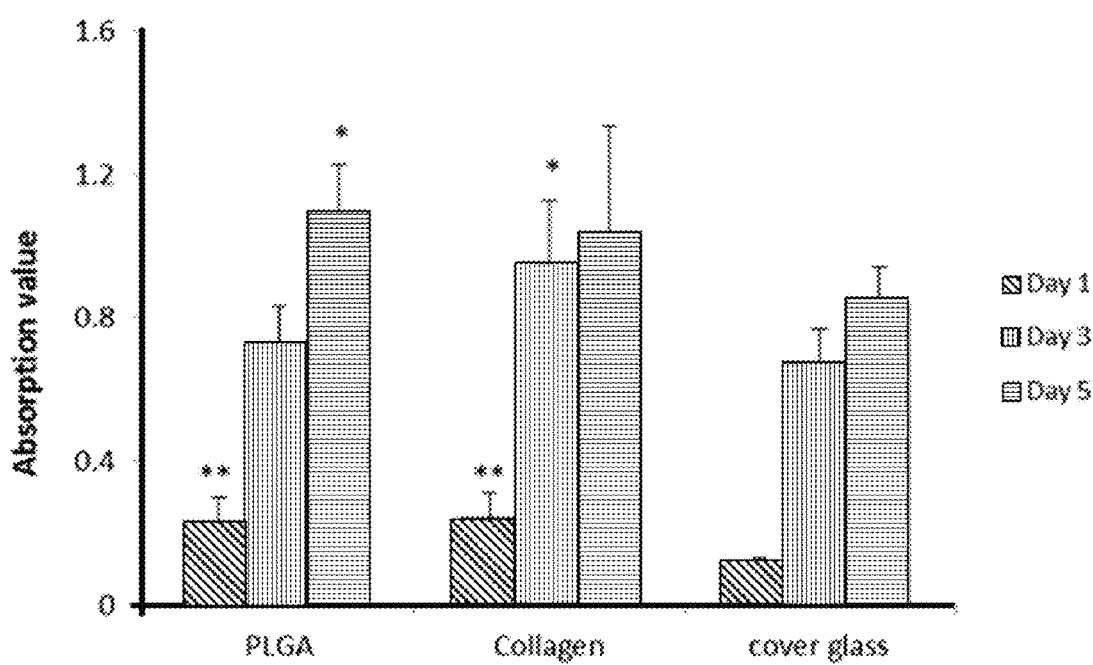
FIG. 26. Proliferation assay of human RPE cells. Human RPE cells were cultured on PLGA and collagen nanofibrous membranes and cover glass (control). At day 1, 3 and 5 the proliferation assay was performed through WST test and the vertical axis shows the absorption value by a spectrophotometer, which indicates the number of viable cells on different substrates. The nanofibrous membranes generally promoted significantly greater proliferation of RPE cells compared to the smooth, cover glass surface. Error bar indicates the standard deviation. *: $p<0.05$: $p<0.01$ for comparison of nanofibrous membranes with cover glass at each time point.

The results of proliferation assay are shown in FIG. 26 and showed that more cells attached on both PLGA and collagen membranes one day after seeding compared to cover glass ($p<0.01$). At day 3, more viable cells were measured on collagen membrane in comparison with PLGA membrane and cover glass, whereas PLGA membrane showed the best support for RPE cell growth at day 5. In general, the proliferation assay demonstrated that the nanofibrous membranes promoted significantly greater proliferation of RPE cells compared to the smooth, cover glass surface after 5 days of culture.

2.3 SEM for Cell Morphology

Figure 27:
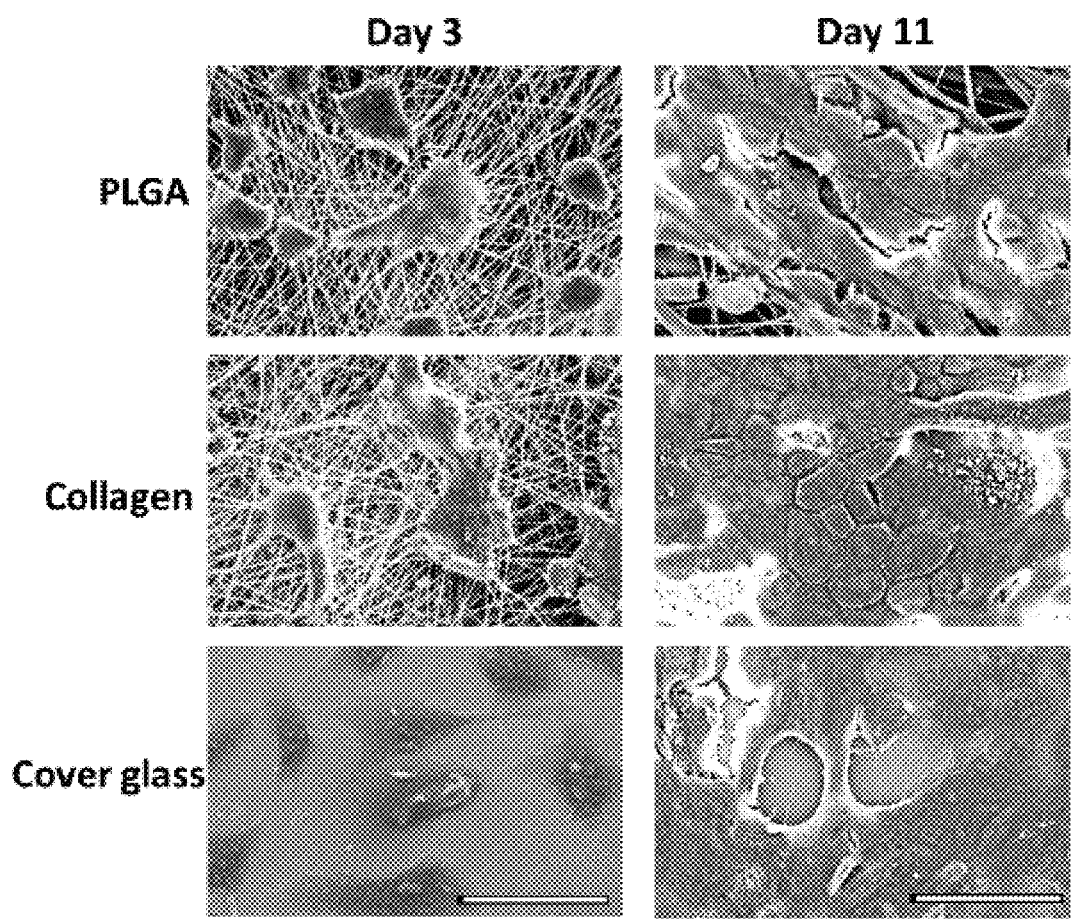
FIG. 27. SEM images of cells on membranes after 3 and 11 days. A: PLGA membrane; B: Collagen membrane; C: Cover glass. Images were taken at magnification of ×600. Scale bar=50 µm. After 3 days, cultured cells presented a polygonal mostly typical hexagonal shape on all substrates. After 11 days, large areas of local confluence were seen and the cells were packed closely.
Figure 28:
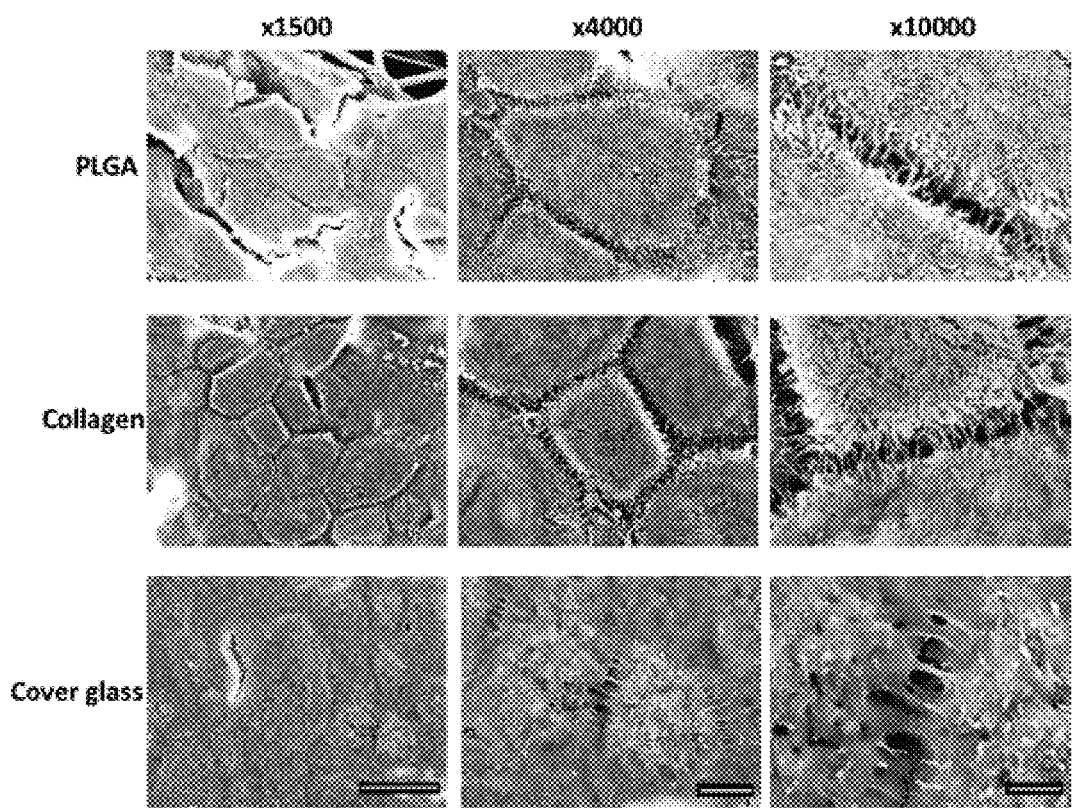
FIG. 28. SEM images of cells on nanofibrillar membranes after 11 days. Images were taken at magnifications of ×1500, ×4000 and ×10000. The scale bars are 20 µm, 5 µm and 2 µm, respectively. Cover glass served as a control. Overall the cells formed a more natural 3-dimensional monolayer on our novel PLGA and collagen nanofibrous membrane compared to flat cover glass. All RPE cells cultured on nanomembranes showed a well orientated monolayer of mostly hexa/polygonal cells with their bases orientated towards the nanomembrane. Abundant, sheet-like microvilli could be observed on the apical surfaces similar to the biological orientation in a human retina where they would envelop the photoreceptor cells. Orientation and microvilli expression in RPE cells on flat cover glass appeared much less organized.

In FIGS. 27 and 28, representative SEM images show human RPE cells on collagen and PLGA membranes and on cover glass. After 3 days, cultured cells presented a polygonal shape on all substrates and showed a well-spread morphology (FIG. 27). After 11 days large areas of local confluence were seen and the cells were packed closely. At higher magnification (FIG. 28), overall the cells formed a more natural 3-dimensional monolayer on PLGA and collagen membrane compared to cover glass. Some cells on cover glass appeared to overlap each other. Well-formed, long, abundant, sheet-like microvilli could be observed covering the surfaces of cells cultured on nanofibrous membranes, while microvilli were less numerous and not as well-formed on the surfaces of cells cultured on cover glass. The cell size in diameter was in the range of 10-14 μm on all tested substrates.

2.4 Immunochemistry

Figure 29:
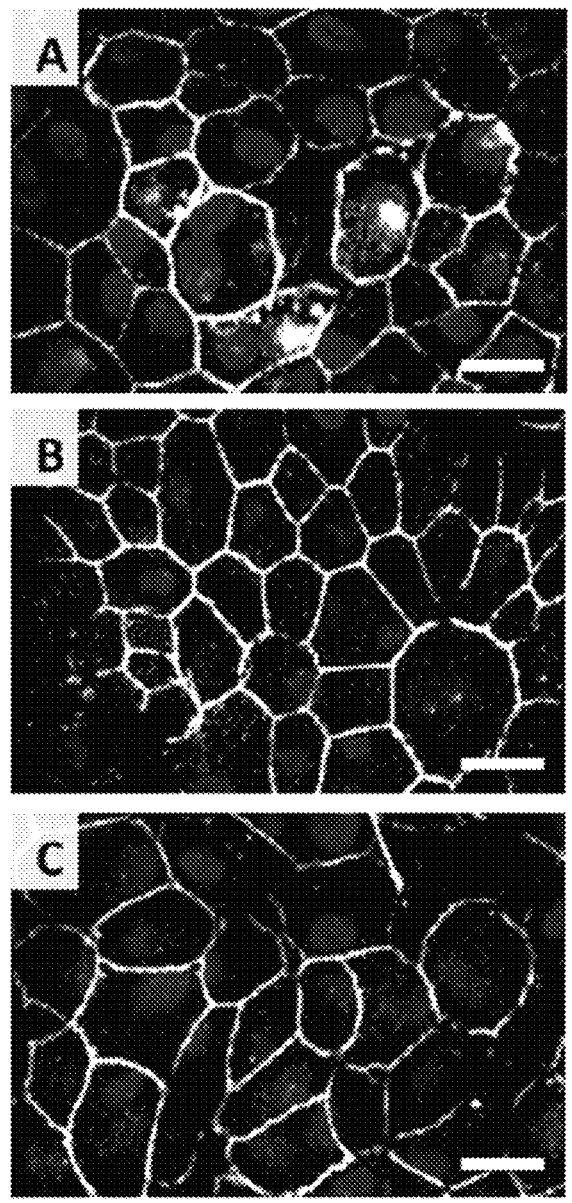
FIG. 29. Expression of ZO-1 by human RPE cells on nanofibrous membranes. Human RPE cells were cultured on PLGA (A), collagen (B) nanofibrillar membranes and on cover glass (C) for 11 days before immunofluorescence staining with ZO-1 antibody (green), a marker of tight junction. Cells cultured on all substrates presented the formation of tight junction and the hexagonal shape as important biofunctional characteristics. Scale bar=20 µm.
Figure 30:
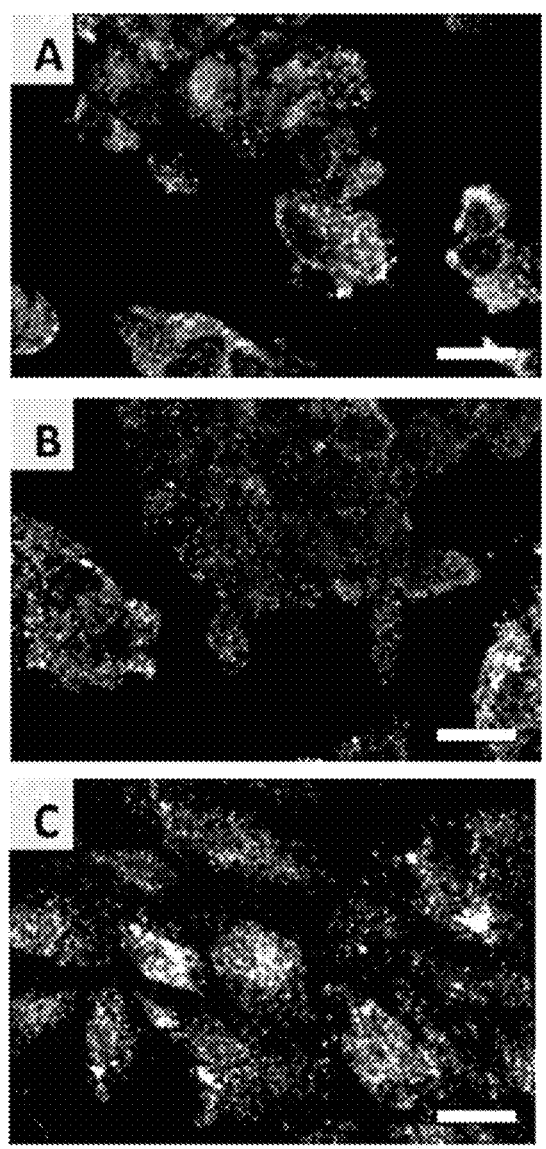
FIG. 30. Expression of RPE65 protein by human RPE cells on nanofibrous membranes. Human RPE cells were cultured on PLGA (A), collagen (B) nanofibrillar membranes and on cover glass (C) for 11 days before immunofluorescence staining with RPE65 antibody. Cells growing on both nanofibrous membranes and on cover glass were positive for the major biofunctional protein RPE65. Scale bar=20 µm.

FIG. 29 shows the confocal microscope images of cells stained against ZO-1, one of the specific markers of tight junction. Cells cultured on all substrates presented the formation of tight junction and the hexagonal shape. Immunofluorescence staining with anti-REP 65 showed that cells growing on both nanofibrous membranes and on cover glass maintained the major functional protein RPE65 (FIG. 30).

3. DISCUSSION

Damage to the RPE monolayer and BM are the major pathologic features of AMD [48]. AMD is a complex disease with lifestyle factors and genetic predisposition contributing to risk. This disease affects the central vision by damaging the macula and thus fine visual acuity, eventually leading to irreversible blindness. The treatments for atrophic AMD are currently severely limited despite the number of laboratory and clinical investigations conducted to find a potential therapy [6]. Cell transplants have partially improved visual function in animal models and AMD patients and hold some promise [7, 10-18, 49]. However, this type of cell therapy is limited by the short survival period and abnormal cell architectures of transplants in vivo [27, 49]. Previous studies showed that the anatomic layers of human BM in the AMD patients are not intact and this alters RPE cell attachment, survival, morphology, and may inhibit RPE growth and maturation [50-53]. Age-related BM alterations include thickening, lipid accumulation, collagen cross-linking and elastin layer calcification. The adverse effects of these changes are likely to be cumulative and progressive [54-56]. To overcome these deficits of the aged BM it is likely that delivering cells on artificial membranes will be necessary for successful implantation in AMD patients.

Potential therapeutic membranes should be compatible with the subretinal space and replicate the features of BM such as supporting RPE cell attachment, growth and maturation as well as regulating nutrient and waste product exchange with the retina [13, 28]. In most studies thin films, 2-dimensional membranes, have been fabricated from naturally derived and synthetic polymers and shown to be biocompatible with RPE cells both in vitro and in vivo [27, 30, 33]. However, the natural BM is a complex, 3-dimensional ECM of interlinked nanoscale protein fibers and the influence of topology on the behaviour of the other cell types has been reported previously [39-41, 59]. The 2-dimensional cell culture environments therefore represent a poor topological approximation of the more complex 3-dimensional architecture of the ECM and could force cells to present non-natural characteristics.

Engineering 3-dimensional cell culture membranes containing nanoscale fibers could allow RPE cells to grow and differentiate under more in vivo-like conditions. Electrospun nanofibrous membranes are good potential candidates having high porosities and surface-area-to-volume ratios which closely represent the nanotopography of the native ECM and thus could encourage cell adhesion, proliferation and organization. In this study, the inventor fabricated two electrospun membranes made of collagen I and PLGA. SEM revealed a random, fibrillar network with fiber diameter ranging from 200 to 500 nm and a fiber packing density of 30.3±1.4% and 37.1±1.1%, respectively (FIG. 25 and the table in Example 10). The SEM of the native, inner collagenous layer of human BM showed a fibrillar network with fiber diameter of 366±98.8 nm and packing density of 30.2±8.2%. In summary, the electrospun membranes of the present invention demonstrated a similar nanofibrillar structure to the native inner collagenous layer of human BM. Further, the engineered membranes should possess proper thickness for transplantation. Both electrospun membranes were thin enough (14 μm) to fit the subretinal space.

Mechanical testing showed the strength and the stiffness of specimens by measuring the maximum tensile stress and Young's modulus respectively. Maximum tensile strength is indicative of the amount of the load that the sample can withstand before failure. Sufficient tensile strength is necessary for the vehicle delivery, as it must withstand manipulation during the surgery and have the physical properties that will make it easy to handle. The Young's modulus indicates the stiffness of specimen. PLGA membrane generally had a lower strength but possessed greater elasticity than the collagen membrane.

RPE cells have rarely been investigated on nanofibrous membranes. In the present study, the inventor demonstrated that RPE cells generally had increased proliferation on nanofibrous membranes than on planar cover glass (FIG. 26). The adhesion of RPE cells one day after seeding was significantly improved by the nanofibrous membranes of the present invention compared to cover glass (p<0.01). During the 5 days' culturing period, cells generally demonstrated a higher proliferation on nanofibrous membranes compared to cover glass.

In order for transplanted RPE nanofibrous membranes to be successful in treating AMD they must also allow or promote RPE maturation and biofunction. After reaching local confluence, RPE cells begin to mature, packing tightly to form a characteristic monolayer of polygonal cells. After 3 days of culturing, cells presented a natural, polygonal shape on each substrate (FIG. 27). After 11 days of culturing RPE cells reached local confluence on all surfaces, however better cell organization was observed on the nanofibrous membranes compared to cover glass (FIGS. 27 and 28). In what may prove to be a crucial observation, well-formed, long, sheet-like microvilli could only be seen clearly on the surfaces of cells cultured on nanofibrous membranes. RPE cells in vivo have the same polarized structure with an apical surface adjacent to the subretinal space and a basolateral surface facing BM. On retinal maturation, very long sheet-like microvilli are developed on the apical surfaces and envelope the tips of the photoreceptors outer segments. Therefore, the apical microvilli of the RPE play critically important roles in retinal attachment and maintenance of the photoreceptor excitability [69, 70]. Since the inventor successfully engineered such RPE monolayers with the same nature-like orientation and microvilli expression on large areas of the invented nanomembrane but not to the same extend on flat cover glass, it is to reason that the nanofibrous substrates/webbing of the invention are superior to non-nanofibrous flat materials with regards to RPE monolayer engineering. Further, RPE cells on nanofibrous membranes exhibited the normal size (10-14 μm) similar to that of the native RPE cells in the macula [13, 71, 72]. Taken together, the inventor considers that the nanofibrous membranes will improve RPE organization and thus would better maintain photoreceptor cells than planar substrates for potential AMD treatment in the future.

The other important biological features of the mature RPE monolayer are tight junction formation and the expression of RPE65 protein. Tight junctions between cells allow the monolayer to act, together with BM, as a blood-retina barrier blocking free passage of water and ions [13, 73]. RPE65 is involved in the visual cycle and its mutation results in severe early-onset blindness [50, 74, 75]. The formation of tight junctions was demonstrated on all the substrates after 11 days of culture by immunofluorescence staining against ZO-1, a specific marker of tight junction (FIG. 29). Likewise RPE cells on all the substrates maintained their expression of the major functional protein RPE65 (FIG. 30).

Taken together, the inventor showed the fabricated nanofibrous membranes performed better than planar cover glass for supporting RPE growth and maturation and expression of biofunctional characteristics and give informative evidence of using electrospun membranes for macular regeneration. Nanofibrous 3-dimensional matrices induce a more in vivo-like organization and morphology than the planar-surface control due to mimicking the nanotopographical architecture of native ECM.

In the present study, the inventor chose collagen I and PLGA polymers as biomaterials to fabricate the nanofibrous membranes. These polymers were selected since they have been well studied and their biocompatibility has been confirmed including with respect to macular degeneration. PLGA is a FDA-approved synthetic polymer for medical implants, degradable by the body into non-toxic breakdown products. Collagen I is a major component of BM and possesses the natural adhesion signal which can enhance cell attachment. The proliferation assay demonstrated better adhesion of RPE cells on collagen I membrane in contrast to cover class (one day after seeding) (FIG. 26). However, no significant difference appeared between PLGA and collagen membrane with respect to the one day attachment. It is considered that the nanofibrillar topography may play a dominant role in this case. The proliferation difference between cells on both membranes was slight at day 3 and 5. Regarding the cell size, organization, formation of tight junction and expression of RPE65, cell behaviour was similar on both nanofibrous membranes suggesting that RPE cell function and maturation was comparable on both substrates. However non-human sources of the polymer collagen I may raise concerns such as transmission of disease and patient allergies to some associated components. In comparison, PLGA, a synthetic chemical polymer, is far cheaper, more stable during preparation and storage. Given the relatively equal in vitro performance the inventor proposes that PLGA is the preferable polymer for membrane-based RPE therapies.

In conclusion, the inventor has demonstrated that the nanofibrous membranes provide a 3-dimensional environment mimicking the structure of inner collagenous layer of human BM, are in vitro biocompatible and promote proliferation and biofunctional maturation of primary human RPE cells. This provides evidence that the composition of the invention is an appropriate carrier for a functional RPE cell monolayer for implantation and treatment of AMD.

REFERENCES

1. Ferris, F. L., 3rd, S. L. Fine, and L. Hyman, Age-related macular degeneration and blindness due to neovascular maculopathy. Arch Ophthalmol, 1984. 102(11): p. 1640-2.
2. Bressler, N. M., S. B. Bressler, and S. L. Fine, Age-related macular degeneration. Surv Ophthalmol, 1988. 32(6): p. 375-413.
3. Okubo, A., et al., The relationships of age changes in retinal pigment epithelium and Bruch's membrane. Invest Ophthalmol V is Sci, 1999. 40(2): p. 443-9.
4. Hogan, M. J., Ultrastructure of the choroid. Its role in the pathogenesis of chorioretinal disease, in Transactions of the Pacific Coast Oto-Ophthalmological Society Annual Meetiing 421961. p. 61-87.
5. Strauss, O., The retinal pigment epithelium in visual function. Physiol Rev, 2005. 85(3): p. 845-81.
6. Liao, J. L., et al., Molecular signature of primary retinal pigment epithelium and stem cellderived RPE cells. Hum Mol Genet, 2010. 19(21): p. 4229-38.
7. Gouras, P., M. T. Flood, and H. Kjeldbye, Transplantation of cultured human retinal cells to monkey retina. An Acad Bras Cienc, 1984. 56(4): p. 431-43.
8. Li, L. X. and J. E. Turner, Inherited retinal dystrophy in the RCS rat: prevention of photoreceptor degeneration by pigment epithelial cell transplantation. Exp Eye Res, 1988. 47(6): p. 911-7.
9. Lopez, R., et al., Transplanted retinal pigment epithelium modifies the retinal degeneration in the RCS rat. Invest Ophthalmol V is Sci, 1989. 30(3): p. 586-8.
10. Lund, R. D., et al., Cell transplantation as a treatment for retinal disease. Prog Retin Eye Res, 2001. 20(4): p. 415-49.
11. Whiteley, S. J., et al., Improvement of the pupillary light reflex of Royal College of Surgeons rats following RPE cell grafts. Exp Neurol, 1996. 140(1): p. 100-4.
12. Peyman, G. A., et al., A technique for retinal pigment epithelium transplantation for agerelated macular degeneration secondary to extensive subfoveal scarring. Ophthalmic Surg, 1991. 22(2): p. 102-8.
13. Binder, S., et al., Transplantation of the RPE in AMD. Prog Retin Eye Res, 2007. 26(5): p. 516-54.
14. Binder, S., et al., Outcome of transplantation of autologous retinal pigment epithelium in age-related macular degeneration: a prospective trial. Invest Ophthalmol V is Sci, 2004. 45(11): p. 4151-60.
15. Phillips, S. J., et al., Autologous transplantation of retinal pigment epithelium after mechanical debridement of Bruch's membrane. Curr Eye Res, 2003. 26(2): p. 81-8.
16. Verma, L., et al., New approaches in the management of choroidal neovascular membrane in age-related macular degeneration. Indian J Ophthalmol, 2000. 48(4): p. 263-78.
17. Radtke, N. D., et al., Vision improvement in retinal degeneration patients by implantation of retina together with retinal pigment epithelium. Am J Ophthalmol, 2008. 146 (2): p. 172-182.
18. Radtke, N. D., et al., Transplantation of intact sheets of fetal neural retina with its retinal pigment epithelium in retinitis pigmentosa patients. Am J Ophthalmol, 2002. 133 (4): p. 544-50.
19. Klimanskaya, I., et al., Derivation and comparative assessment of retinal pigment epithelium from human embryonic stem cells using transcriptomics. Cloning Stem Cells, 2004. 6(3): p. 217-45.
20. Lund, R. D., et al., Human embryonic stem cell-derived cells rescue visual function in dystrophic RCS rats. Cloning Stem Cells, 2006. 8(3): p. 189-99.
21. Can, A. J., et al., Molecular characterization and functional analysis of phagocytosis by human embryonic stem cell-derived RPE cells using a novel human retinal assay. Mol V is, 2009. 15: p. 283-95.
22. Vugler, A., et al., Elucidating the phenomenon of HESC-derived RPE: anatomy of cell genesis, expansion and retinal transplantation. Exp Neurol, 2008. 214(2): p. 347-61.
23. Vugler, A., et al., Embryonic stem cells and retinal repair. Mech Dev, 2007. 124(1112): p. 807-29.
24. Gong, J., et al., Effects of extracellular matrix and neighboring cells on induction of human embryonic stem cells into retinal or retinal pigment epithelial progenitors. Exp Eye Res, 2008. 86(6): p. 957-65.
25. Lu, B., et al., Long-term safety and function of RPE from human embryonic stem cells in preclinical models of macular degeneration. Stem Cells, 2009. 27(9): p. 2126-35.
26. Lu, B., et al., Mesh-supported submicron parylene-C membranes for culturing retinal pigment epithelial cells. Biomed Microdevices, 2012.
27. Hynes, S. R. and E. B. Lavik, A tissue-engineered approach towards retinal repair: scaffolds for cell transplantation to the subretinal space. Graefes Arch Clin Exp Ophthalmol, 2010. 248(6): p. 763-78.
28. da Cruz, L., et al., RPE transplantation and its role in retinal disease. Prog Retin Eye Res, 2007. 26(6): p. 598-635.
29. Lim, J. M., et al., Retinal pigment epithelial cell behavior is modulated by alterations in focal cell-substrate contacts. Invest Ophthalmol V is Sci, 2004. 45(11): p. 4210-6.
30. Srivastava, G. K., et al., Elastin-like recombinamers as substrates for retinal pigment epithelial cell growth. J Biomed Mater Res A, 2011. 97(3): p. 243-50.
31. Bhatt, N. S., et al., Experimental transplantation of human retinal pigment epithelial cells on collagen substrates. Am J Ophthalmol, 1994. 117(2): p. 214-21.
32. Thumann, G., et al., Characteristics of iris and retinal pigment epithelial cells cultured on collagen type I membranes. Curr Eye Res, 2006. 31(3): p. 241-9.
33. Lu, J. T., et al., Thin collagen film scaffolds for retinal epithelial cell culture. Biomaterials, 2007. 28(8): p. 1486-94.
34. Imai, H., et al., The upregulation of angiogenic gene expression in cultured retinal pigment epithelial cells grown on type I collagen. Curr Eye Res, 2007. 32(10): p. 903-10.

35. Thomson, R. C., et al., Manufacture and characterization of poly(alpha-hydroxy ester) thin films as temporary substrates for retinal pigment epithelium cells. Biomaterials, 1996. 17(3): p. 321-7.
36. Giordano, G. G., et al., Retinal pigment epithelium cells cultured on synthetic biodegradable polymers. J Biomed Mater Res, 1997. 34(1): p. 87-93.
37. Lu, L., M. J. Yaszemski, and A. G. Mikos, Retinal pigment epithelium engineering using synthetic biodegradable polymers. Biomaterials, 2001. 22(24): p. 3345-55.
38. Shadforth, A. M. A., et al., The cultivation of human retinal pigment epithelial cells on *Bombyx mori* silk fibroin. Biomaterials, 2012. 33(16): p. 4110-4117.
39. Curtis, A. and C. Wilkinson, Topographical control of cells. Biomaterials, 1997. 18(24): p. 1573-83.
40. Berthiaume, F., et al., Effect of extracellular matrix topology on cell structure, function, and physiological responsiveness: hepatocytes cultured in a sandwich configuration. FASEB J, 1996. 10(13): p. 1471-84.
41. Bettinger, C. J., R. Langer, and J. T. Borenstein, Engineering substrate topography at the micro- and nanoscale to control cell function. Angew Chem Int Ed Engl, 2009. 48(30): p. 5406-15.
42. Nisbet, D. R., et al., Review paper: a review of the cellular response on electrospun nanofibers for tissue engineering. J Biomater Appl, 2009. 24(1): p. 7-29.
43. Chew, S. Y., et al., The role of electrospinning in the emerging field of nanomedicine. Curr Pharm Des, 2006. 12(36): p. 4751-70.
44. Kumbar, S. G., et al., Electrospun nanofiber scaffolds: engineering soft tissues. Biomed Mater, 2008. 3(3): p. 034002.
45. Sill, T. J. and H. A. von Recum, Electrospinning: applications in drug delivery and tissue engineering. Biomaterials, 2008. 29(13): p. 1989-2006.
46. Kuijpers, A. J., et al., Cross-linking and characterisation of gelatin matrices for biomedical applications. J Biomater Sci Polym Ed, 2000. 11(3): p. 225-43.
47. Wang, H., et al., Retinal pigment epithelium wound healing in human Bruch's membrane explants. Invest Ophthalmol V is Sci, 2003. 44(5): p. 2199-210.
48. Leibowitz, H. M., et al., The Framingham Eye Study monograph: An ophthalmological and epidemiological study of cataract, glaucoma, diabetic retinopathy, macular degeneration, and visual acuity in a general population of 2631 adults, 1973-1975. Surv Ophthalmol, 1980. 24(Suppl): p. 335-610.
49. Seiler, M. J. and R. B. Aramant, Cell replacement and visual restoration by retinal sheet transplants. Prog Retin Eye Res, 2012.
50. Gullapalli, V. K., et al., Retinal pigment epithelium resurfacing of aged submacular human Bruch's membrane. Trans Am Ophthalmol Soc, 2004. 102: p. 123-37; discussion 137-8.
51. Sun, K., et al., Bruch's membrane aging decreases phagocytosis of outer segments by retinal pigment epithelium. Mol Vis, 2007. 13: p. 2310-9.
52. Paik, D. C., et al., The nitrite/collagen reaction: non-enzymatic nitration as a model system for age-related damage. Connect Tissue Res, 2001. 42(2): p. 111-22.
53. Deberg, M., et al., New serum biochemical markers (Coll 2-1 and Coll 2-1 NO2) for studying oxidative-related type II collagen network degradation in patients with osteoarthritis and rheumatoid arthritis. Osteoarthritis Cartilage, 2005. 13(3): p. 258-65.
54. Booij, J. C., et al., The dynamic nature of Bruch's membrane. Prog Retin Eye Res, 2010. 29(1): p. 1-18.
55. Ramrattan, R. S., et al., Morphometric analysis of Bruch's membrane, the choriocapillaris, and the choroid in aging. Invest Ophthalmol V is Sci, 1994. 35(6): p. 2857-64.
56. Beatty, S., et al., The role of oxidative stress in the pathogenesis of age-related macular degeneration. Surv Ophthalmol, 2000. 45(2): p. 115-34.
57. Lavik, E. B., et al., Fabrication of degradable polymer scaffolds to direct the integration and differentiation of retinal progenitors. Biomaterials, 2005. 26(16): p. 3187-3196.
58. Tomita, M., et al., Biodegradable polymer composite grafts promote the survival and differentiation of retinal progenitor cells. Stem Cells, 2005. 23(10): p. 1579-88.
59. Schindler, M., et al., A synthetic nanofibrillar matrix promotes in vivo-like organization and morphogenesis for cells in culture. Biomaterials, 2005. 26(28): p. 5624-31.
60. Dong, Y., et al., Degradation behaviors of electrospun resorbable polyester nanofibers. Tissue Eng Part B Rev, 2009. 15(3): p. 333-51.
61. Han, D. and P. I. Gouma, Electrospun bioscaffolds that mimic the topology of extracellular matrix. Nanomedicine, 2006. 2(1): p. 37-41.
62. Mano, J. F., et al., Natural origin biodegradable systems in tissue engineering and regenerative medicine: present status and some moving trends. J R Soc Interface, 2007. 4(17): p. 999-1030.
63. Engel, E., et al., Nanotechnology in regenerative medicine: the materials side. Trends Biotechnol, 2008. 26(1): p. 39-47.
64. Nur, E. K. A., et al., Three-dimensional nanofibrillar surfaces promote self-renewal in mouse embryonic stem cells. Stem Cells, 2006. 24(2): p. 426-33.
65. Guaccio, A., et al., Influence of electrospun fiber mesh size on hMSC oxygen metabolism in 3D collagen matrices: experimental and theoretical evidences. Biotechnol Bioeng, 2011. 108(8): p. 1965-76.
66. Prabhakaran, M. P., J. Venugopal, and S. Ramakrishna, Electrospun nanostructured scaffolds for bone tissue engineering. Acta Biomater, 2009. 5(8): p. 2884-93.
67. Yang, F., et al., Electrospinning of nano/micro scale poly (L-lactic acid) aligned fibers and their potential in neural tissue engineering. Biomaterials, 2005. 26(15): p. 2603-10.
68. Thieltges, F., et al., A nanofibrillar surface promotes superior growth characteristics in cultured human retinal pigment epithelium. Ophthalmic Res, 2011. 46(3): p. 133-40.
69. Marmor, M. F., Mechanisms of fluid accumulation in retinal edema. Doc Ophthalmol, 1999. 97(3-4): p. 239-49.
70. Bonilha, V. L., et al., The retinal pigment epithelium apical microvilli and retinal function. Adv Exp Med Biol, 2006. 572: p. 519-24.
71. Harman, A. M., et al., Development and aging of cell topography in the human retinal pigment epithelium. Invest Ophthalmol V is Sci, 1997. 38(10): p. 2016-26.
72. Panda-Jonas, S., J. B. Jonas, and M. Jakobczyk-Zmija, Retinal pigment epithelial cell count, distribution, and correlations in normal human eyes. Am J Ophthalmol, 1996. 121(2): p. 181-9.
73. Rizzolo, L. J., et al., Integration of tight junctions and claudins with the barrier functions of the retinal pigment epithelium. Prog Retin Eye Res, 2011. 30(5): p. 296-323.
74. Wenzel, A., et al., RPE65 is essential for the function of cone photoreceptors in NRL deficient mice. Invest Ophthalmol V is Sci, 2007. 48(2): p. 534-42.
75. Redmond, T. M., et al., Rpe65 is necessary for production of 11-cis-vitamin A in the retinal visual cycle. Nat Genet, 1998. 20(4): p. 344-51.

76. Barnes, C. P., et al., Nanofiber technology: designing the next generation of tissue engineering scaffolds. Adv Drug Deliv Rev, 2007. 59(14): p. 1413-33.

What is claimed is:

1. A composition to treat age-related macular degeneration or other retinal diseases or disorders, wherein the composition comprises a three-dimensional (3D) membrane comprising electrospun nanofibers made by at least one polymer, the at least one polymer comprising PLGA, PCL, elastin, collagen or combinations thereof, wherein the membrane is ultrathin and comprises a packing density and fiber diameter sufficient to load stem cell derived retinal cells onto the membrane, the membrane further comprising a protein coat between the nanofibers and the stem cell derived retinal cells, wherein the thickness of the membrane is between about 2 microns to about 20 microns and the packing density is between about 15% to about 70% and the fiber diameter is between about 250 nm to about 670 nm.

2. The composition of claim 1, wherein the packing density and fiber diameter of the membrane allow the loaded stem cell derived retinal cells to proliferate into a functional monolayer of retinal pigment epithelium.

3. The composition of claim 2, wherein the retinal pigment epithelium treats age-related macular degeneration or other retinal diseases or disorders.

4. The composition of claim 1, wherein the topography and modulus of the membrane resembles the topography and modulus of native human Bruch's membrane.

5. The composition of claim 1, further comprising photoreceptor cells.

6. The composition of claim 5, wherein the photoreceptor cells and retinal pigment epithelial cells make up a bilayer, said retinal pigment epithelial cells facing the membrane.

7. The composition of claim 1, wherein the composition is flexible and is therefore contoured to the shape of the implant site by surrounding tissue.

8. The composition of claim 1, wherein the two or more polymers are natural and/or synthetic and biodegradable.

9. A composition comprising a protein-coated nanofiber membrane supporting a functional monolayer of stem cell derived retinal pigment epithelial cells, wherein the composition is obtainable by a process comprising the following steps:
(a) placing a collector in an electric field of a nanofiber electrospinning machine;
(b) dispersing one or more polymers through an electric field to contact the collector for a time and under conditions sufficient to produce packing density and nanofiber diameter of the membrane to resemble the topography of native human Bruch's membrane, and a thickness of the membrane to support cell growth and mimic the mechanical properties of native human Bruch's membrane;
(c) removing the membrane from the collector;
(d) washing and sterilizing the membrane;
(e) coating the membrane with a protein coat;
(f) loading the membrane with stem cell derived retinal cells; and
(g) culturing the cells in vitro to functional maturity.

10. The composition of claim 9, wherein photoreceptor cells are loaded onto the retinal pigment epithelial cell-loaded membrane.

11. The composition of claim 1 or 6, wherein the composition is implanted subretinally into a patient's eye.

* * * * *